(12) United States Patent
Kuriger et al.

(10) Patent No.: US 10,864,335 B2
(45) Date of Patent: *Dec. 15, 2020

(54) SYSTEM, APPARATUS AND METHODS FOR SUPPLYING GASES

(71) Applicants: FISHER & PAYKEL HEALTHCARE LIMITED, Auckland (NZ); NEW YORK UNIVERSITY, New York, NY (US)

(72) Inventors: Donald Roy Kuriger, Auckland (NZ); David Cumin, Auckland (NZ); David M. Rapoport, New York, NY (US); Christopher Earl Nightingale, Auckland (NZ); Sujeewa Wannigama, Auckland (NZ); Mark John Arrowsmith, Auckland (NZ); Vitaly Kapelevich, Auckland (NZ)

(73) Assignees: Fisher & Paykel Healthcare Limited, Auckland (NZ); New York University, New York, NY (US)

( * ) Notice: Subject to any disclaimer, the term of this patent is extended or adjusted under 35 U.S.C. 154(b) by 500 days.

This patent is subject to a terminal disclaimer.

(21) Appl. No.: 15/684,327

(22) Filed: Aug. 23, 2017

(65) Prior Publication Data

US 2018/0036499 A1    Feb. 8, 2018

Related U.S. Application Data

(63) Continuation of application No. 14/378,924, filed as application No. PCT/NZ2013/000014 on Feb. 15, 2013, now Pat. No. 9,750,908.

(Continued)

(51) Int. Cl.
*A61M 16/00*    (2006.01)
*A61M 16/20*    (2006.01)
(Continued)

(52) U.S. Cl.
CPC ....... *A61M 16/0069* (2014.02); *A61B 5/4818* (2013.01); *A61M 16/0051* (2013.01);
(Continued)

(58) Field of Classification Search
CPC ..... A61B 5/0476; A61B 5/087; A61B 5/4812; A61B 5/4818; A61B 5/4836;
(Continued)

(56) References Cited

U.S. PATENT DOCUMENTS 4,991,623 A    2/1991  Ericson
5,503,146 A *  4/1996  Froehlich ............ A61M 16/024
                                                          128/202.22
(Continued)

FOREIGN PATENT DOCUMENTS

CN    1835775 A    9/2006
CN    1901962 A    1/2007
(Continued)

OTHER PUBLICATIONS

Communication pursuant to Article 94(3) EPC for European App. No. 13812496.1, dated Jan. 29, 2019, in 4 pages.
(Continued)

*Primary Examiner* — Annette Dixon
(74) *Attorney, Agent, or Firm* — Fay Kaplun & Marcin, LLP

(57) ABSTRACT

A system, apparatus and methods are provided for supplying gases to a user. The supply includes a sub-therapeutic mode and a pressure support mode for delivering therapy to a user. A flow diversion device or valve switches from a first mode corresponding with the sub-therapeutic mode of the system to a second mode corresponding with the pressure support mode of the system. In the first mode, the valve opens a larger flow path between the interior of the user interface and ambient air than in the second mode.

15 Claims, 32 Drawing Sheets

Related U.S. Application Data

(60) Provisional application No. 61/599,273, filed on Feb. 15, 2012.

(51) Int. Cl.

| | | |
|---|---|---|
| *A61M 16/10* | (2006.01) | |
| *A61M 16/16* | (2006.01) | |
| *A61B 5/00* | (2006.01) | |
| *A61M 16/06* | (2006.01) | |
| *A61M 16/22* | (2006.01) | |

(52) U.S. Cl.
CPC .......... *A61M 16/06* (2013.01); *A61M 16/109* (2014.02); *A61M 16/1075* (2013.01); *A61M 16/16* (2013.01); *A61M 16/20* (2013.01); *A61M 16/202* (2014.02); *A61M 16/204* (2014.02); *A61M 16/205* (2014.02); *A61M 16/208* (2013.01); *A61M 16/22* (2013.01); A61M 2016/003 (2013.01); A61M 2016/0027 (2013.01); A61M 2016/0039 (2013.01); A61M 2205/14 (2013.01); A61M 2205/3303 (2013.01); A61M 2205/3334 (2013.01); A61M 2205/42 (2013.01); A61M 2205/50 (2013.01); A61M 2205/6054 (2013.01); A61M 2230/42 (2013.01)

(58) Field of Classification Search
CPC .......... A61M 16/0003; A61M 16/0051; A61M 16/0057; A61M 16/0066; A61M 16/0069; A61M 16/024; A61M 16/06; A61M 16/0605; A61M 16/0666; A61M 16/0683; A61M 16/0816; A61M 16/0875; A61M 16/1075; A61M 16/109; A61M 16/16; A61M 16/20; A61M 16/202; A61M 16/204; A61M 16/205; A61M 16/208; A61M 16/22; A61M 2016/0021; A61M 2016/0027; A61M 2016/003; A61M 2016/0036; A61M 2016/0039; A61M 2205/13; A61M 2205/14; A61M 2205/15; A61M 2205/3303; A61M 2205/3334; A61M 2205/3365; A61M 2205/3553; A61M 2205/3584; A61M 2205/3592; A61M 2205/3653; A61M 2205/42; A61M 2205/50; A61M 2205/502; A61M 2205/52; A61M 2205/583; A61M 2205/6054; A61M 2205/80; A61M 2230/40; A61M 2230/42

See application file for complete search history.

(56) References Cited

U.S. PATENT DOCUMENTS

| | | | |
|---|---|---|---|
| 5,551,419 A * | 9/1996 | Froehlich | A61M 16/024 128/204.23 |
| 5,839,436 A | 11/1998 | Fangrow, Jr. et al. | |
| 5,937,855 A | 8/1999 | Zdrojkowski et al. | |
| 6,062,248 A | 5/2000 | Boelkins | |
| 6,186,477 B1 | 2/2001 | McCombs et al. | |
| 6,988,994 B2 | 1/2006 | Rapoport et al. | |
| 7,798,143 B1 | 9/2010 | Kirby | |
| 9,314,579 B2 | 4/2016 | McDaniel et al. | |
| 9,750,908 B2 * | 9/2017 | Kuriger | A61M 16/0051 |
| 10,099,026 B2 * | 10/2018 | Rapoport | A61M 16/0066 |
| 10,258,754 B2 * | 4/2019 | Nightingale | A61M 16/06 |
| 2003/0005931 A1 | 1/2003 | D. Jaffre et al. | |
| 2004/0129270 A1 | 7/2004 | Fishman | |
| 2007/0113849 A1 | 5/2007 | Matthews et al. | |
| 2008/0047426 A1 | 2/2008 | Dolensky | |
| 2008/0092894 A1 | 4/2008 | Nicolazzi et al. | |
| 2008/0097234 A1 | 4/2008 | Nicolazzi et al. | |
| 2009/0038616 A1 * | 2/2009 | Mulcahy | A61M 16/0051 128/204.23 |
| 2009/0205662 A1 * | 8/2009 | Kwok | A61M 16/0051 128/204.23 |
| 2010/0108064 A1 * | 5/2010 | Blackwell | A61M 16/024 128/204.21 |
| 2010/0126506 A1 | 5/2010 | Kepler et al. | |
| 2010/0180895 A1 * | 7/2010 | Kwok | A61M 16/0051 128/204.23 |
| 2011/0259334 A1 | 10/2011 | Alfieri et al. | |
| 2012/0065533 A1 | 3/2012 | Carrillo, Jr. et al. | |
| 2014/0000610 A1 | 1/2014 | Rapoport | |
| 2014/0096774 A1 | 4/2014 | Olsen et al. | |
| 2014/0283842 A1 | 9/2014 | Bearne et al. | |
| 2016/0015918 A1 | 1/2016 | Kuriger et al. | |

FOREIGN PATENT DOCUMENTS

| | | |
|---|---|---|
| EP | 0788805 A2 | 8/1997 |
| WO | WO 1992/011054 A1 | 7/1992 |
| WO | WO 2000/038772 A1 | 7/2000 |
| WO | WO 2002/051486 A1 | 7/2002 |
| WO | WO 2005/063326 A1 | 7/2005 |
| WO | WO 2007/045008 A1 | 4/2007 |
| WO | WO 2008/039979 A2 | 4/2008 |
| WO | WO 2010/044036 A1 | 4/2010 |
| WO | WO 2010/140072 A1 | 9/2010 |
| WO | WO 2012/006339 A2 | 1/2012 |
| WO | WO 2012/020314 | 2/2012 |
| WO | WO 2012/075433 A3 | 6/2012 |
| WO | WO 2012/140514 | 10/2012 |
| WO | WO 2013/066195 | 10/2013 |
| WO | WO 2014/007659 A1 | 1/2014 |

OTHER PUBLICATIONS

International Search Report for PCT/NZ2013/000014 dated Sep. 24, 2013 in 7 pages.
Supplementary Search Report for PCT/NZ2013/000014 dated Jul. 23, 2015 in 7 pages.
International Preliminary Report on Patentability in PCT Application No. PCT/US2011/063137, dated Jun. 13, 2013 in 7 pages.
International Search Report; PCT/US2011/063137; dated Jun. 22, 2012 in 3 pages.
Office Action in Chinese Patent Application No. 201180064696.9, dated Feb. 2, 2015 in 2 pages.
Patent Examination Report in Application No. GB 1310564.8 dated Feb. 18, 2016 in 5 pages.
Patent Examination Report in Australian Application No. 2011336371, dated Jun. 29, 2015 in 3 pages.
Written Opinion; PCT/US2011/063137; dated Jun. 22, 2012 in 6 pages.
Patent Examination Report in Canadian Application No. 2819647, dated Oct. 18, 2017 in 4 pages.

* cited by examiner

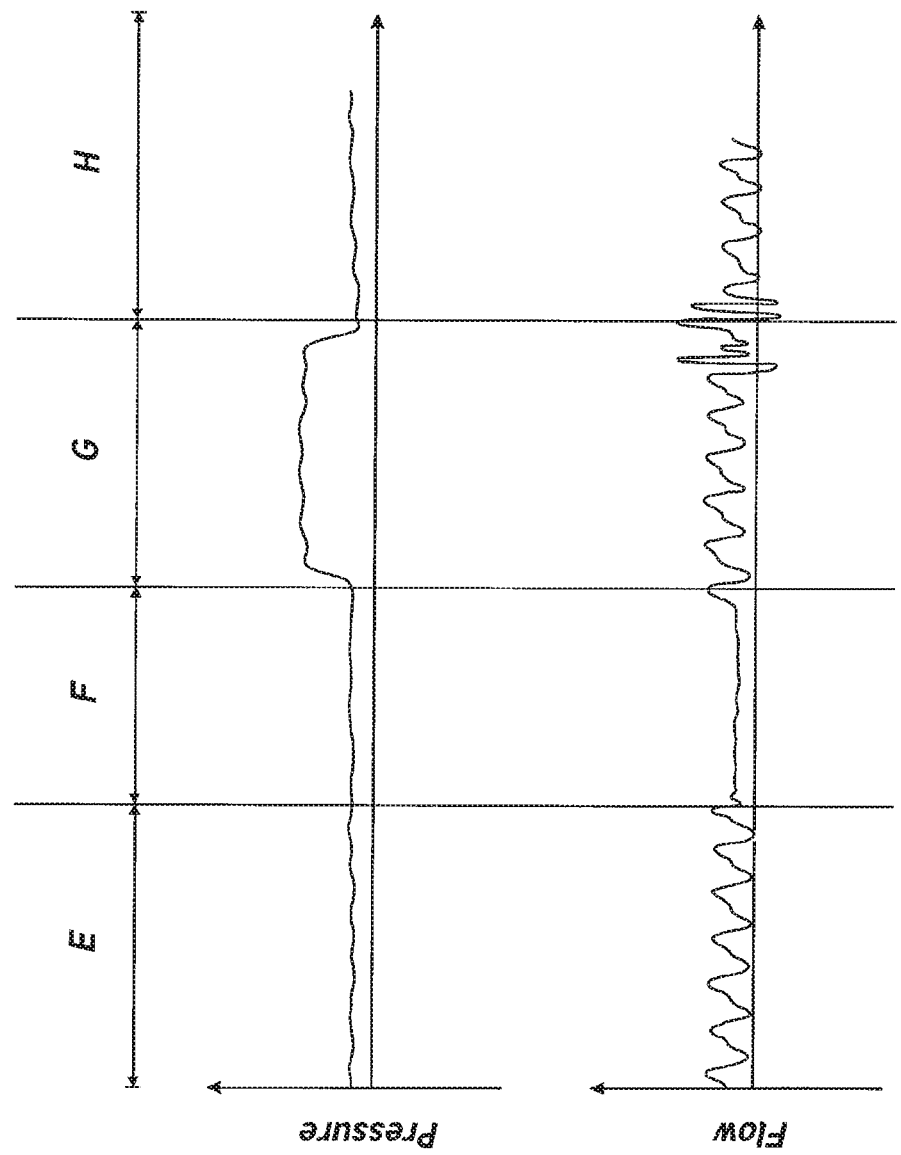

SYSTEM, APPARATUS AND METHODS FOR SUPPLYING GASES

CROSS-REFERENCE TO RELATED APPLICATIONS

The present application is a Continuation of U.S. patent application Ser. No. 14/378,924 filed on Aug. 14, 2014, now U.S. Pat. No. 9,750,908; which is a 371 application of PCT Application Serial No. PCT/NZ2013/000014 filed on Feb. 15, 2013; which claims the benefit of U.S. Provisional Application Serial No. 61/599,273 filed on Feb. 15, 2012. The entire disclosures of the above patent(s)/application(s) are expressly incorporated herein by reference.

BACKGROUND

Field

The present invention generally relates to apparatus and methods for supplying respiratory gas under positive pressure to a sleeping user, such as in the treatment of obstructive sleep apnea (OSA). More particularly, the present invention relates to such apparatus and methods in which a condition of a user's body is sensed. Even more particularly, the present invention relates to such apparatus and methods featuring a gas supply that is responsive to breathing and that includes a valve in the control mechanism.

Description of Related Art

A common method of treating obstructive sleep apnea (OSA) involves a pressure device that provides breathing gases, typically air, to a user (often referred to as the patient) while the user is asleep. These machines fall into the broad classification of PAP (positive airway pressure) devices or CPAP (continuous PAP) devices.

Within this broad classification, there are wide variations. For example, some machines provide different pressure during user inspiration than during user expiration (Bi PAP), some machines provide an auto-setting or autotitrating mode, wherein the supplied pressure varies through the period of use in response to detected events. In this context, detected events may include snoring, hypopneas and obstructive breathing. Some machines respond to user awakening and mask removal, for example, by reducing the delivered pressure. Some machines deliver a predetermined set pressure, which may be delivered at the same pressure night after night or which may be varied night by night by physical adjustment or by automatic adjustment by the unit. Some machines include a ramp function that begins automatically or that begins by user selection. The ramp function causes the machine to commence operation at a low pressure, which is sometimes settable, and to gradually increase to a higher pressure, which may be a predetermined treatment pressure or which may be an intermediate pressure.

The machines typically provide controlled pressure delivery. For example, the machines typically include a flow generator, a pressure sensor that senses the pressure being delivered to the user, and a feedback control that controls the output of the flow generator based upon a sensor signal so that the sensed pressure is maintained close to a demand pressure. Alternatively, the flow generator may include a fan that generates a known pressure and flow response. The output of the flow generator can be controlled to deliver a desired pressure using feedback from a flow sensor in a circuit that is connected to the flow generator. Alternatively, the flow generator may include a fan that provides a substantially uniform pressure at a given rotation speed across a useful range of flow. Pressure then can be controlled by setting a constant motor speed.

Even for the lower pressure at the start of a ramp cycle, most of the machines supply a minimum pressure of 3 cmH2O or more. The minimum pressure is more comfortable for the user than the full treatment pressure and results in a sufficient flow of breathing gases through a supply line to the user so that breathing gases exit through a bias flow or a controlled leak port provided at or near a user interface that is connected to the supply line.

SUMMARY

An object of the present invention is to provide apparatus or methods for providing breathing gases to a user, which at least go some way toward improving on prior systems, or which will at least provide users with a useful choice.

In some configurations, an apparatus comprises a flow generator and a controller connected to control the output of the flow generator. A conduit extends from the flow generator to connect with a user interface with the inside of the conduit and the inside of the user interface defining a gases space. A valve positioned at or adjacent the user interface. The valve being switchable between a first mode in which the gases space is significantly open to ambient through the valve and a second mode in which the gases space is significantly closed to ambient through the valve. The controller including one or more positive airway pressure support modes in which the controller may cause the flow generator to deliver pressure support to the airway of a user with the valve in the second mode and the controller including one or more sub-therapeutic modes in which the controller may cause the flow generator to deliver flow of gases to the user with the valve in the first mode.

The valve can include an aperture that communicates the gases space with ambient and a valve member that, in a second position, closes the aperture and is substantially out of the flow path of gases through the conduit or interface and, in a first position, leaves the aperture open for substantially unimpeded flow from the interface to the ambient.

In the first position, the valve member may partially, but not fully, occlude flow from the flow generator to the interface. In some configurations, the first position of the valve comprises the valve being bent towards the user when the user is inhaling. In some configurations, the first position of the valve comprises the valve being bent toward the flow generator when the user is exhaling.

The valve member when in the first position preferably occludes between about 50% and about 80% of a cross-sectional area of a flow path from the flow generator to the user interface.

The positive airway pressure support modes can include a supply of gases to a user such that, with the valve in the first mode, the flow generator provides enough flow to the user interface such that with the interface worn by a user a pressure greater than about 3 cm H2O is produced.

A sensor can be included to derive a measure of pressure in the gases space such that in a positive airway pressure mode the controller controls output of the flow generator according to a command pressure and feedback from the sensor for deriving the measure of pressure in the gases space.

In some configurations, in the sub-therapeutic mode, the controller provides a flow to the interface that is not sufficient to force the valve into the closed position.

In the sub-therapeutic mode, the controller can cause the flow generator to provide a flow greater than about 5 litres per minute (most preferably greater than about 10 litres per minute).

In some configurations, in the sub-therapeutic mode, the controller causes the flow generator to provide a flow less than about 20 litres per minute (most preferably less than 15 litres per minute).

The valve can move from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve can remain stable for flows up to at least about 20 litres per minute, with delivered pressures below about 2 cm H2O.

With the valve in the second mode, and the controller operating in the pressure support mode, the valve can remain stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 litres per minute.

In some configurations, in the sub-therapeutic mode, the controller controls the flow generator to deliver an average flow at a level that assures flushing of the user interface but which does not trigger the valve to switch from the first mode to the second mode.

In some configurations, the controller controls the flow generator to provide an average flow over multiple breaths that is substantially constant.

In some configurations, an apparatus comprises a flow generator and a controller connected to control the output of the flow generator. A conduit extends from the flow generator to connect with a user interface. The inside of the user interface defines a gases space. A valve at or adjacent the user interface is switchable between a first mode, in which the gases space is open to ambient through the valve, and a second mode, in which the gases space generally is not open to ambient through the valve. Control of the flow generator and the construction and arrangement of the valve can be such that in a period of transition (in either direction) between a pressure support delivery to the user and a sub-therapeutic supply to the user, user breathing does not trigger repeated cycling between the first mode and the second mode.

The controller can include one or more positive airway pressure support modes in which the controller may cause the flow generator to deliver pressure support to the airway of a user with the valve in the second mode and one or more sub-therapeutic modes in which the controller may cause the flow generator to deliver flow of gases to the user with the valve in the first mode.

In some configurations, the one or more positive airway pressure modes include supply of gases to the user such that, with the valve in the closed position, the flow generator provides enough flow to the user interface such that, with the interface worn by a user, a pressure greater than about 3 cm H2O is produced.

A sensor can be provided to derive a measure of pressure in the gases space wherein, in a positive airway pressure mode, the controller controls the output of the flow generator according to a command pressure and feedback of the measure of pressure in the gases space from the sensor.

In some configurations, in the sub-therapeutic mode, the controller provides a flow to the interface that is not sufficient to force the valve into the first mode.

In some configurations, in the sub-therapeutic mode, the controller causes the flow generator to provide a flow greater than about 5 litres per minute (most preferably greater than about 10 litres per minute).

In some configurations, in the sub-therapeutic mode, the controller causes the flow generator to provide a flow less than about 20 litres per minute (most preferably less than about 15 litres per minute).

In some configurations, in the sub-therapeutic mode, the controller controls the flow generator to deliver an average flow at a level that assures flushing of the user interface, but which does not trigger the valve to switch from the first mode to the second mode.

The controller can control the flow generator to provide an average flow over multiple breaths that is substantially constant.

The valve can include an aperture communicating the gases space with ambient and a valve member that in a first position closes the aperture and is out of the flow path of gases through the conduit or interface and in a second position leaves the aperture open for substantially unimpeded flow from the interface to the ambient.

In some configurations, in the second position, the valve member partially, but not fully, occludes flow from the flow generator to the interface.

In some configurations, in the second position, the area valve member occludes between about 50% and about 80% of a cross sectional area of a flow path from the flow generator to the user interface.

In some configurations, the valve moves from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve remains stable for flows up to at least about 20 litres per minute with delivered pressures below about 2 cm H2O.

In some configurations, with the valve in the second mode and the controller operating in the pressure support mode, the valve remains stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 litres per minute.

In some configurations, an apparatus comprises a flow generator, a controller connected to control the output of the flow generator, and a conduit extending from the flow generator to connect with a user interface with the inside of the conduit and the inside of the user interface defining a gases space. A valve can be positioned at or adjacent the user interface and can include an aperture communicating the gases space with ambient and a valve member wherein, in a first position, the valve member leaves the aperture substantially open for flow from the interface to the ambient and, in a second position, the valve member closes the aperture, and wherein the valve member moves from the first position to the second position upon rising through a first threshold of flow/pressure, and from the second position to the first position on falling through a second threshold of flow/pressure, wherein the first threshold of flow/pressure is higher than the second threshold of flow/pressure.

The controller can include one or more positive airway pressure support modes in which the controller causes the flow generator to deliver pressure support to the airway of a user with the valve in the second mode and one or more sub-therapeutic modes in which the controller causes the flow generator to deliver flow of gases to the user with the valve in the first mode.

The positive airway pressure modes can include supply of gases to the user such that, with the valve in the closed position, the flow generator provides enough flow to the user interface such that, with the interface worn by a user, a pressure greater than about 3 cm H2O is produced.

A sensor can be provided to obtain a measure of pressure in the gases space such that, in a positive airway pressure mode, the controller controls the output of the flow generator according to a command pressure and feedback of the measure of pressure in the gases space from the sensor.

In some configurations, in the sub-therapeutic mode, the controller provides a flow to the interface that is not sufficient to force the valve into the closed position.

In some configurations, in the sub-therapeutic mode, the controller causes the flow generator to provide a flow greater than about 5 litres per minute (most preferably greater than about 10 litres per minute).

In some configurations, in the sub-therapeutic mode, the controller causes the flow generator to provide a flow less than about 20 litres per minute (most preferably less than about 15 litres per minute).

In some configurations, in the sub-therapeutic mode, the controller controls the flow generator to deliver an average flow at a level that assures flushing of the user interface but which does not trigger the valve to switch from the first position to the second position.

In some configurations, the controller controls the flow generator to provide an average flow over multiple breaths that is substantially constant.

In some configurations, with the valve in the first position and the controller operating in the sub-therapeutic mode, the valve remains stable for flows up to at least about 20 litres per minute with delivered pressures below about 2 cm H2O.

In some configurations, with the valve in the second position and the controller operating in the pressure support mode, the valve remains stable at pressures down to about 3 cm H2O or lower.

In some configurations, the lowest pressure for which the valve is stable in the second position when the controller is in the pressure support mode is less than about 1 cm H2O above the average delivered pressure when the valve is in the first position and the controller is in the sub-therapeutic mode supplying about 15 litres per minute.

In some configurations, in the second position, the valve member partially, but not fully, occludes flow from the flow generator to the interface.

In some configurations, in the second position, the valve member occludes between about 50% and about 80% of a cross sectional area of a flow path from the flow generator to the user interface.

In some configurations, an apparatus comprises a flow generator, a controller connected to control the output of the flow generator, and a nasal mask for covering nasal passages of a wearer but leaving a mouth uncovered. A conduit extends from the flow generator to connect with the nasal mask with the inside of the conduit and the inside of the nasal mask defining a gases space. A valve is positioned at or adjacent the nasal mask which is switchable between a first mode, where the gases space is open to ambient through the valve, and a second mode, where the gases space is not open to ambient through the valve. The controller controls the flow generator to deliver gases through the conduit with the valve in the first mode and with the valve in the second mode.

The controller can include one or more positive airway pressure support modes in which the controller may cause the flow generator to deliver pressure support to the airway of a user with the valve in the second mode, and one or more sub-therapeutic modes in which the controller may cause the flow generator to deliver flow of gases to the user with the valve in the first mode.

The positive airway pressure modes can include supply of gases to the user such that, with the valve in the first mode, the flow generator provides enough flow to the user interface such that, with the interface worn by a user, a pressure greater than 3 cm H2O is produced.

A sensor can be provided for deriving a measure of pressure in the gases space where, in a positive airway pressure mode, the controller controls the output of the flow generator according to a command pressure and feedback of the measure of pressure in the gases space.

In some configurations, in the sub-therapeutic mode, the controller provides a flow to the interface that is not sufficient to force the valve into the second mode.

In some configurations, in the sub-therapeutic mode, the controller causes the flow generator to provide a flow greater than about 5 litres per minute (most preferably greater than about 10 litres per minute).

In some configurations, in the sub-therapeutic mode, the controller causes the flow generator to provide a flow less than about 20 litres per minute (most preferably less than about 15 litres per minute).

In some configurations, in the sub-therapeutic mode, the controller controls the flow generator to deliver an average flow at a level that assures flushing of the user interface but that does not trigger the valve to switch from the first mode to the second mode.

In some configurations, the controller controls the flow generator to provide an average flow over multiple breaths that is substantially constant.

In some configurations, the valve includes an aperture communicating the gases space with ambient and a valve member that is moveable between a first position corresponding to the second mode and a second position corresponding to the first mode, the valve member in the first position closing the aperture and being positioned out of the flow path of gases between the valve inlet and the valve outlet, and the valve member in a second position leaving the aperture open for substantially unimpeded flow from the valve inlet to ambient.

In some configurations, in the second position, the valve member partially, but not fully, occludes flow from the valve inlet to the valve outlet.

In some configurations, in the second position, the valve member occludes between about 50% and about 80% of a cross sectional area of a flow path from the valve inlet to the valve outlet.

In some configurations, the valve moves from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve remains stable for flows up to at least about 20 litres per minute with delivered pressures below 2 cm H2O.

In some configurations, with the valve in the second mode and the controller operating in the pressure support mode, the valve remains stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 litres per minute.

A valve can be provided for use at or adjacent a user interface. The valve comprises a flow passage defined by at least one wall. The flow passage extends between a valve inlet and a valve outlet configured to open toward the user interface. An aperture through the at least one wall defines the flow passage. The aperture is positioned between the valve inlet and the valve outlet with a valve member being positioned between the valve inlet and the aperture. The valve member is movable between a first position and a second position. The valve member in the first position leaving the aperture open for flow from the interface to ambient and the valve member in the second position closing the aperture. The valve member is adapted to move from the first position to the second position upon rising through a first threshold of flow/pressure in the flow passage, and the valve member is adapted to move from the second position to the first position on falling through a second threshold of flow/pressure in the flow passage, wherein the first threshold of flow/pressure is higher than the second threshold of flow/pressure.

In some configurations, in the second position, the valve member partially, but not fully, occludes flow from the valve inlet to the valve outlet.

In some configurations, in the second position, the valve member occludes between 50% and 80% of a cross sectional area of a flow path from the valve inlet to the valve outlet.

A valve can be provided for use at or adjacent a user interface. The valve comprises a flow passage at least partially defined by a wall. The flow passage extends between a valve inlet and a valve outlet that is adapted to be fluidly connected to the user interface. An aperture is defined through the wall. The aperture is positioned between the valve inlet and the valve outlet with a valve member being positioned between the valve inlet and the aperture. The valve member is movable between a first position and a second position. When the valve member is in the first position, the aperture is left open for flow from the interface to ambient. When the valve member is in the first position, flow is partially but not fully occluded through the flow passage. When the valve member is in the second position, the aperture is substantially closed. The valve member in the first position occludes between about 50% and about 80% of a cross section area of a flow passage between the inlet and the outlet at the valve member.

In some configurations, a cross-sectional area of the flow passage through the valve at the valve member is between about 40 mm2 and about 250 mm2.

In some configurations, the area of the aperture is between about 10% and about 50% of the cross sectional area of the flow passage through the valve.

In some configurations, the area of the aperture is between about 15% and about 25% of the cross sectional area of the flow passage through the valve.

In some configurations, in the second position, the valve member partially, but not fully, occludes flow from the flow generator to the interface.

In some configurations, in the second position, the area valve member occludes between about 50% and about 80% of the area of the flow path from the flow generator to the user interface.

A valve can be provided for use at or adjacent a user interface. The valve comprises a flow passage defined by a wall. The flow passage extends between a valve inlet and a valve outlet. An aperture is defined through the wall. The aperture is positioned between the valve inlet and the valve outlet. A valve member is positioned between the valve inlet and the aperture. The valve member is movable between a first position and a second position, wherein the valve member in the first position leaving the aperture open for flow from the user interface to ambient, the valve member in the second position at least partially closing the aperture, and the valve member being stable in the first position under user breathing for average flows over multiple breaths of up to 30 litres per minute, delivering a pressure below about 1.5 cm H2O, and being stable in the second position under user breathing for controlled pressures above about 1.7 cm H2O.

In some configurations, a cross-sectional area of the flow passage through the valve from the inlet to the outlet is between about 350 mm2 and about 600 mm2.

In some configurations, the area of the aperture is between 10% and 50% of a cross-sectional area of the flow passage through the valve.

In some configurations, the area of the aperture is between 15% and 25% of the cross sectional area of the flow passage through the valve.

In some configurations, in the second position, the valve member partially, but not fully, occludes flow from the flow generator to the interface.

In some configurations, in the second position, the valve member occludes between about 50% and about 80% of a cross sectional area of the flow path from the flow generator to the user interface.

In some configurations, a system is provided for supplying respiratory gases to a user wearing a user interface. The system comprises a flow generator and a controller adapted to control operation of the flow generator. The flow generator has a flow control mode and a pressure control mode. The flow control mode comprises generation of a sub-therapeutic flow of gases and the pressure control mode comprises generation of a therapeutic flow of gases. A flow diversion valve is positioned between the flow generator and the user interface. The flow diversion valve comprises a flow channel and an aperture. The aperture places the flow channel in fluid communication with ambient. The flow diversion valve further comprises a valve member that is cantilevered from a wall and that extends toward the flow channel in a first position. The valve member is moveable between the first position and a second position. The valve member overlies at least a portion of the aperture in the second position and the valve member occludes only a portion of the flow channel in the first position. The valve member is movable from the first position to the second position when the flow generator transitions from the flow control mode to the pressure control mode and movable from the second position toward the first position when the flow generator transitions from the pressure control mode to the flow control mode.

In some configurations, the valve member does not abut a valve seat in the first position.

In some configurations, the valve member is in the first position when there is no flow through the flow channel and the valve member does not abut a valve seat in the first position. In some configurations, the first position of the valve comprises the valve being bent towards the user when the user is inhaling. In some configurations, the first position of the valve comprises the valve being bent toward the flow generator when the user is exhaling.

In some configurations, the valve member when in the first position occludes between about 50% and about 80% of a cross-sectional area of the flow channel.

In some configurations, the flow control mode comprises delivering an average flow rate of between about 15 litres per minute and about 17 litres per minute.

In some configurations, the flow control mode comprises delivering a pressure of less than about 4 centimeters water.

In some configurations, the valve member abuts a land in the second position.

In some configurations, the land is offset inwardly toward the flow channel from a portion of the valve member that is secured to a body of the valve.

In some configurations, the aperture defines an opening with a cross-sectional area of about 90 mm2.

In some applications, a system is configured for supplying respiratory gases to a user wearing a user interface. The system comprises a flow generator and a controller controlling operation of the flow generator. The controller operates the flow generator in a first mode to create a first pressure that is below a therapeutic pressure range and the controller operates the flow generator in a second mode to create a second pressure that is within the therapeutic pressure range. The system transitions between the first mode and the second mode in synchrony with a breathing state of the user.

In some configurations, the system transitions from the first mode to the second mode in synchrony with an inhalation of the user.

In some configurations, the system transitions from the second mode to the first mode in synchrony with an exhalation of the user.

In some configurations, the system monitors a flow rate while operating in the first mode and the system transitions to the second mode if the flow rate decreases below a lower threshold for a preset period of time.

In some configurations, the second mode comprises a pressure mode.

In some configurations, the system transitions from the first mode to the second mode when the user is determined to be sleeping.

In some configurations, the system determines the user to be sleeping based upon detection of sleep disordered breathing events.

In some configurations, the system transitions from the second mode to the first mode is a minimum therapeutic pressure is reached in the second mode.

In some configurations, the system increases pressure in synchrony with inhalation of the user in the second mode.

In some configurations, the system decreases pressure in synchrony with exhalation of the user in the second mode.

In some configurations, the system further comprises a port to ambient and a valve assuming a first position and a second position. In the second position, the valve substantially closes the port. The port is positioned between the user and the flow generator.

In some configurations, the valve transitions from the first position to the second position are a result of the system transitioning from the first mode to the second mode.

In some configurations, the system transitions from the first mode to the second mode during inhalation of the user.

In some configurations, the system transitions from the first mode to the second mode when the system detects the start of inhalation of the user.

In some applications, a system is configured for supplying respiratory gases to a user wearing a user interface. The system comprises a flow generator and a controller controlling operation of the flow generator. The controller operates the flow generator in a first mode creating a first pressure that is below a therapeutic pressure range and the controller operates the flow generator in a second mode creating a second pressure that is within the therapeutic pressure range. The controller is configured to detect a sleep state of the user and to transition the system between the first mode and the second mode in response to a change in the sleep state.

In some configurations, the system further comprises a port to ambient, the port being positioned between the user and the flow generator. The system is configured to transition from the first mode to the second mode by decreasing a venting area of the port.

In some configurations, the system comprises a valve configured to increase or decrease the venting area of the port. The valve is configured to assume a first position and a second position wherein, in the second position, the valve substantially closes the port by occluding a portion of the venting area.

In some configurations, the valve transitions from the first position to the second position as a result of the system transitioning from the first mode to the second mode.

In some configurations, the system transitions between the first mode and the second mode in synchrony with a breathing state of the user.

In some configurations, the system transitions from the first mode to the second mode in synchrony with an inhalation of the user.

In some configurations, the system transitions from the second mode to the first mode in synchrony with an exhalation of the user.

In some configurations, the second mode comprises a pressure mode.

In some configurations, the system transitions from the first mode to the second mode when the user is determined to be sleeping.

In some configurations, the system determines the user to be sleeping based upon detection of sleep disordered breathing events.

In some configurations, the system increases pressure in synchrony with inhalation of the user in the second mode.

In some configurations, the system decreases pressure in synchrony with exhalation of the user in the second mode.

In some configurations, the system transitions from the first mode to the second mode during inhalation of the user.

In some configurations, the system transitions from the first mode to the second mode when the system detects the start of inhalation of the user.

In some configurations, the controller operates the flow generator in the first mode to provide an average flow rate of gases. In some configurations, the average flow rate is less than or equal to about 20 litres per minute.

In some configurations, the controller operates the flow generator in the first mode to provide an average low pressure. In some configurations, the average low pressure is less than or equal to about 3 cm H2O.

In some configurations, the controller operates the flow generator in the first mode to provide an average flow rate or an average low pressure and the controller is configured to switch the operation of the flow generator in the first mode between providing the average flow rate and the average low pressure.

In some configurations, the controller determines the sleep state of the user to be sleeping when the user experiences two or more apneas within a time window, four or more flow-limited breaths in a row, a hypopnea, an obstructive hypopnea, and/or some combination of apnea, hypopnea and flow-limited breaths.

In some configurations, the controller determines the sleep state of the user to be awakening when a breath waveform changes in frequency or amplitude, or when a breath waveform evidences an irregularity indicating awakening.

In some configurations, the venting area of the port is configured to be greater than or equal to about 60 mm2 when the controller determines the sleep state of the user to be awake.

In some configurations, in the first mode, the venting area of the port is configured to be greater than or equal to about 60 mm2 and the controller operates the flow generator to provide an average low pressure that is less than or equal to about 0.5 cm H2O.

A flow diversion device having a pressure-dependent valve can be provided for use near, adjacent, or at a user interface. The flow diversion device comprises a flow passage defined by at least one wall. The flow passage extends between an inlet portion and an outlet portion configured to open toward the user interface. The flow diversion device comprises a flow port extending through the at least one wall, the flow port connecting the flow passage and ambient. The flow port is positioned between the inlet portion and the outlet portion. The flow diversion device comprises a pressure-dependent valve being positioned in the flow port wherein the pressure-dependent valve is movable between a first position and a second position. The pressure-dependent valve is adapted to assume the first position in response to a first range of pressures in the flow passage and assume the second position in response to a second range of pressures in the flow passage, the first range of pressures being lower than the second range of pressures. The pressure-dependent valve in the first position leaves the flow port substantially open for flow from the user interface to ambient, and the pressure-dependent valve in the second position substantially occludes the flow port.

In some configurations, the pressure-dependent valve comprises a base having an opening and a resilient valve member coupled to the base, the resilient valve member extending from the base and forming a valve aperture. The valve aperture formed by the resilient valve member is configured to reduce in size in response to an increase in pressure through the flow passage.

In some configurations, the pressure-dependent valve is configured to remain in the first position when, in the flow passage, a pressure is within the first range of pressures and a flow rate varies.

In some configurations, the pressure-dependent valve is configured to remain in the second position when, in the flow passage, a pressure is within the second range of pressures and a flow rate varies.

In some configurations, the pressure-dependent valve maintains the valve member in the first position when a pressure in the flow passage is within the first range of pressures and the second position when the pressure is within the second range of pressures. The pressure-dependent valve transitions the valve member between the first position and the second position in response to a change in pressure between the first range and the second range and not to a change in flow.

In some configurations, the resilient valve member comprises a plurality of cuspids, wherein adjacent cuspids are joined by a cuspid wing having a cuspid lip. The cuspid lips are configured to contact one another to substantially close the valve aperture in response to the second range of pressures through the flow passage.

In some configurations, the flow diversion device comprises an elbow connector that is coupled to the user interface.

A flow diversion device having a constant-flow valve can be provided for use near, adjacent, or at a user interface. The flow diversion device comprises a flow passage defined by at least one wall. The flow passage extends between an inlet portion and an outlet portion configured to open toward the user interface. The flow diversion device comprises a flow port extending through the at least one wall, the flow port connecting the flow passage and ambient. The flow port is positioned between the inlet portion and the outlet portion. The flow diversion device comprises a constant-flow valve positioned within the flow diversion device. The constant-flow valve is adapted to provide a constant flow rate through the flow passage when a pressure through the flow passage exceeds a constant-flow pressure threshold. The constant-flow valve is adapted to be movable between a first position and a second position wherein, in the first position, the flow passage is substantially occluded leaving the flow port substantially open for flow from the user interface to ambient, and, in the second position, the flow port is substantially occluded leaving the flow passage substantially open for flow from the inlet portion to the outlet portion.

In some configurations, the constant-flow valve comprises a curved valve member coupled to the at least one wall near the flow port, the curved valve member configured to substantially occlude the flow passage in the first position and to substantially occlude the flow port in the second position, wherein the curved valve member is configured to move between the first position and the second position.

In some configurations, the curved valve member has a substantially parabolic cross-section.

In some configurations, the constant-flow valve maintains the curved valve member in the first position when a pressure through the flow passage is within a first pressure range and the second position when the pressure through the flow passage is within a second pressure range.

In some configurations, the constant-flow valve maintains the curved valve member in the first position when a flow rate through the flow passage is within a first flow range and the second position when the flow rate through the flow passage is within a second flow range.

In some configurations, the flow diversion device comprises an elbow connector that is coupled to the user interface.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The term "comprising" is used in the specification and claims, means "consisting at least in part of" When interpreting a statement in this specification and claims that includes "comprising," features other than that or those prefaced by the term may also be present. Related terms such as "comprise" and "comprises" are to be interpreted in the same manner.

BRIEF DESCRIPTION OF THE DRAWINGS

These and other features, aspects and advantages of the present invention will now be described with reference to the drawings of preferred embodiments, which embodiments are intended to illustrate and not to limit the invention, and in which figures:

FIG. 3a and FIG. 3b are two non-limiting examples of plots of pressure and flow against time for portions of a session using an apparatus that is arranged and configured in accordance with certain features, aspects and advantages of the present invention.

DETAILED DESCRIPTION

Figure 1:
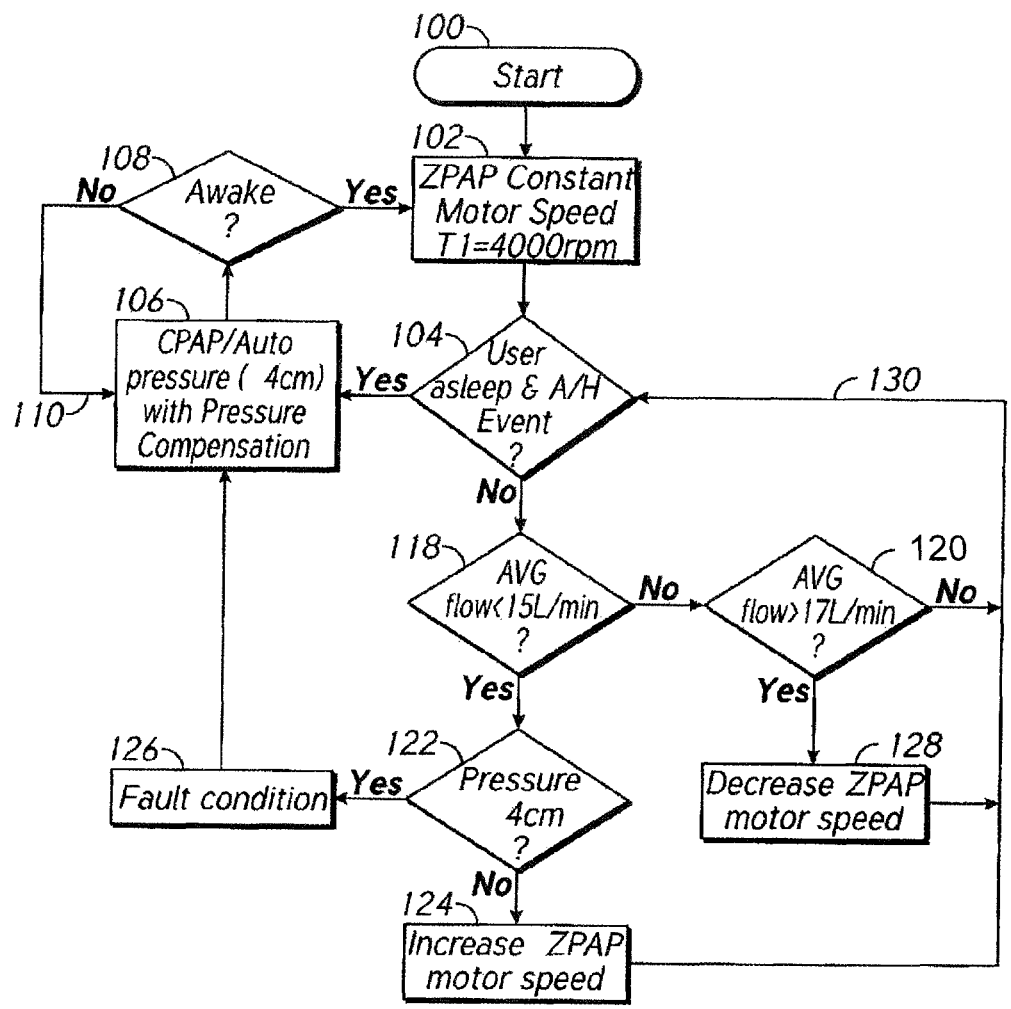
FIG. 1 is a flow diagram illustrating a control method that is arranged and configured in accordance with certain features, aspects and advantages of the present invention and that can be implemented by a controller of a gas supply apparatus.

The following description presents a system and elements of that system, that can provide an alternative to a defined pressure ramp at the commencement of a treatment session. The system, and the elements of that system, also can provide an alternative to low therapeutic pressures (i.e., awake pressures) at other times when a user is thought to be awake.

Certain features, aspects and advantages of the present invention relate to a sub-therapeutic control mode in which the user receives mask pressures that approach ambient or atmospheric pressure, which is referred to herein as "zero pressure." The use of zero pressure contrasts with traditional therapeutic CPAP, which maintains a therapeutic level of pressure at all times when therapy for obstructive sleep apnea is needed. The terms therapeutic pressure or therapeutic pressure ranges can mean any pressure or pressure range that is suitable for treating a patient, or treatment pressures, where the treatment can include treating the patient for obstructive sleep apnea. For example, a therapeutic pressure can be a pressure that is between about 3 cmH2O and about 30 cmH2O, or between about 3 cmH2O and about 20 cmH2O. The terms sub-therapeutic pressure or sub-therapeutic pressure ranges can include pressures that are non-treatment pressures. For example, sub-therapeutic pressures can be less than or equal to about 4 cmH2O.

A sub-therapeutic control mode allows very low mask pressures at times when therapy is not needed, desired or intended. The very low mask pressures make using the system more pleasant for the user by removing unnecessary or undesired pressure wherever possible while reducing the likelihood of compromising other functions of the system (e.g., external venting to reduce the likelihood of $CO_2$ rebreathing). Because of increased comfort produced by reduced perceived pressure when therapeutic airway support is not needed or not desired, the sub-therapeutic control mode is believed to encourage increased compliance, which will extend the time the user wears the system and receives therapeutic CPAP treatment.

A limiting factor in the implementation of sub-therapeutic gas delivery with existing CPAP machines is that substantially all systems currently used with CPAP machines rely on non-zero mask and circuit pressure to force air through a "leak port" throughout the respiratory cycle. The air forced out through the leak port provides venting of exhaled carbon dioxide, particularly during exhalation, and reduces the likelihood of rebreathing of exhaled gas during the next inspiration. When the mask and circuit pressure falls below a certain low level (e.g., generally around 2 cm H2O to 5 cm H2O depending upon the size of the leak port), venting through a fixed size leak port becomes generally ineffective.

Two types of valves that can be used in the system that is arranged and configured in accordance with certain features, aspects and advantages of the present invention are "non-rebreathing" valves and "exhalation valves." Each of the two types of valves creates a second port through which exhaled gas can be directed to reduce the likelihood of rebreathing. Non-rebreathing valves generally are passively opened when the relevant pressure is substantially zero or zero (e.g., when a gas supply apparatus has stopped functioning) or when flow reverses within a circuit. Exhalation valves also can be used in non-CPAP circuits and typically trigger from shut to open with rises in pressure during exhalation. Exhalation valves are often driven by an external triggering mechanism that detects expiration; however, when used during CPAP, the exhalation valves cannot be dependent on pressure at the valve alone because the pressure is high in both therapeutic CPAP and during exhalation. In addition, the valve must be actively triggered or driven by an outside controller. In some embodiments, the system can be implemented with specifically adapted valves having characteristics described later in this specification.

Some implementations of the sub-therapeutic mode utilize an external decision about which mode of the valve is active. At a predetermined point, which could be predicated on the desired CPAP pressure or on the state of arousal of a user, the controller adjusts the characteristics of the flow and pressure in the circuit to trigger an increase in the leak out of the circuit, such as, for example but without limitation, opening an additional port or otherwise creating an increase in leakage flow. In the therapeutic CPAP mode, the controller delivers gases at a flow and pressure such that the valve minimizes the size of the leak (e.g., by closing the additional port). Preferably, the change in valve behaviour occurs generally as a passive response of the valve but in response to some signal generated by an algorithm controlling CPAP delivery.

Preferably, the transition from the sub-therapeutic mode to the conventional therapy mode of operation (i.e., CPAP) happens in a substantially "smooth" fashion and does not significantly oscillate with respiratory swings. Thus, the mode change may be largely undetected or minimally intrusive to the user. One aspect of making the transition generally transparent to the user is minimizing the change in system conditions (e.g., pressure and flow) that activates the change in mode of operation of the valve while preserving the stability of the valve mode.

Certain features, aspects and advantages of the present invention relate to a valve with two modes. Certain features, aspects and advantages of the present invention relate to activating control of the valve mode through changes in the behaviour of the CPAP gas supply without other external control signals to the valve. Preferably, despite minimal change in pressure but at a desired time, the valve switches between an "open" state, a state with minimal pressure in the circuit and low but significant flow to the user, and a "closed" state, a state with pressure that can be raised to therapeutic levels, and the transition occurs with little or no change in the system conditions perceived by the user. In other words, the "open" state refers to the interior of the circuit being open to ambient surroundings through the valve while the "closed" state refers to a state where the valve does not allow the same substantial flow between inside the circuit and ambient through the valve. However, some flow between inside the circuit and ambient may be provided for in the closed state. For example, the valve may incorporate a bias flow vent to provide suitable leak during therapy.

Figure 2:
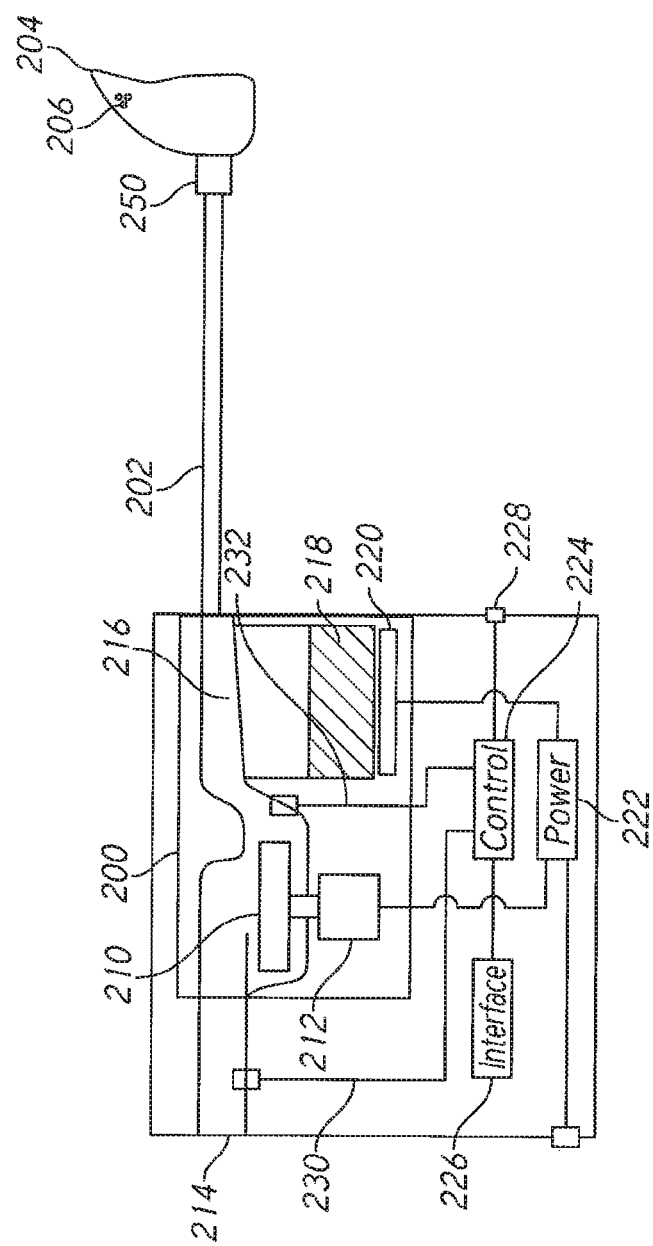
FIG. 2 is a block diagram illustrating a gases supply system that is arranged and configured in accordance with certain features, aspects and advantages of the present invention.

With reference to FIG. 2, the system generally comprises a gas supply device 200, a user interface 204, a supply conduit or tube 202 for connecting between the supply device 200 and the user interface 204 and a flow diversion device 250. The flow diversion device preferably is located at or generally adjacent to the user interface 204.

The flow diversion device 250 can operate in at least two modes. In some configurations, the flow diversion device 250 operates in only two modes. In a first mode, the gases space inside the user interface 204 is substantially open or open to ambient surroundings through the flow diversion device 250. In a second mode, the flow diversion device 250 allows the user to receive a gases flow at a therapeutic treatment pressure from the gases supply device 200.

Preferably, the flow diversion device 250 comprises a type of valve in which the valve 250 is in the first mode or condition at low pressure or flow conditions (i.e., sub-therapeutic supply conditions). In this condition, the interior of the user interface 204 is substantially open to ambient surroundings through the valve 250. In the second mode or condition, the valve 250 is closed and the gases space inside the user interface 204 is significantly less open to ambient surroundings through the valve 250.

Typically, the gases space inside the user interface 204 may be connected at all times with the ambient environment through a vent 206, such as a bias flow vent or other controlled leak port. For example, the vent 206 is illustrated in FIG. 2 on the user interface 204. In some configurations, the vent 206 may be part of the flow diversion device 250 itself.

Preferably, the flow path to ambient surroundings through the flow diversion device 250, with the valve in the first mode, is a path of much lower resistance than the flow path through the controlled leak provided through the vent 206. Thus, with the flow diversion device 250 in the first mode, the flow path between the gases supply device 200 and the gases space inside the user interface 204 is somewhat restricted but is not closed while a comparatively open flow path is provided between the gases space inside the user interface 204 and the surrounding ambient conditions through the flow diversion device 250. In the second mode, there is comparatively little or no flow between the gases space inside the user interface 204 and the surrounding ambient conditions through the flow diversion device 250 while the flow diversion device 250 presents a comparatively low flow restriction between the gases space inside the user interface 204 and the gases supply device 200.

Preferably, the control of the gases supply device 200 and the arrangement of the flow diversion device 250 (e.g., the valve) are adapted so that, in a period of transition in either direction between delivery of pressure support to the user and delivery of a sub-therapeutic supply to the user, user breathing does not trigger repeated cycling between the first mode and the second mode of the flow diversion device 250. Accordingly, the valve 250 does not flutter to any significant degree at this transition.

Preferably, the flow diversion device 250 switches from the first mode to the second mode and from the second mode to the first mode according to the prevailing flow and pressure conditions. Typically, these flow and pressure conditions are generated by the gases supply device 200 and user breathing. Thus, the gases supply device 200 provides a base condition (e.g., flow and/or pressure) and the user breathing superimposes a transient variation in flow and/or pressure as the user inhalation and exhalation flow is superimposed on the flow from the gas supply device 200.

The flow diversion device 250 preferably has no means of control other than the prevailing flow and/or pressure conditions acting on the valve 250 and an associated valve member. The valve 250 is not actively controlled except by the flow generator 200 varying the prevailing pressure and/or flow conditions.

When the system gradually moves between a sub-therapeutic pressure and a therapeutic support pressure in the gases supply, the flow diversion device 250 closes to be in the second mode. Similarly, in moving from a therapeutic support pressure to a sub-therapeutic level, the flow diversion device 250 opens to be in the first mode.

The transition can be unstable for regular pressure or speed control flow generators. In particular, as the conditions reach a level at which the valve 250 will move from the first mode to the second mode, the fluctuation in conditions caused by user breathing can lead to the valve 250 opening and closing with each user breath. A similar effect can be noted where the pressure support is decreasing toward the sub-therapeutic level and approaches the transition conditions for the flow diversion device 250.

Accordingly, the flow diversion device 250 in the illustrated system switches from the first mode (i.e., the open mode) to the second mode (i.e., the closed mode) at a first set of conditions, and from the second mode (i.e., the closed mode) to the first mode (i.e., the open mode) under a second set of conditions. The first set of conditions is relatively higher than the second set of conditions. Accordingly, with the average pressure and/or flow increasing, when the flow diversion device 250 switches from the first mode to the second mode, the minimum pressure and/or flow is already above the pressure and/or flow at which it would switch from the second mode to the first mode. Similarly, when the average pressure and/or flow is decreasing, once the flow diversion device 250 switches from the second mode to the first mode, the minimum pressure and/or flow is already below the pressure and/or flow at which it would switch from the first mode to the second mode.

Preferably, the difference in the level of the conditions is greater than the fluctuation in the conditions resulting merely from user breathing. The fluctuation depends on system conditions. For example, pressure fluctuation in the region of the valve 250 depends on resistance to flow exiting the system. With the flow diversion device 250 open, the interior of the user interface 204 and flow diversion device 250 are more openly connected to the surrounding ambient conditions and the fluctuating pressure creates a smaller pressure swing than with the flow diversion device 250 closed. Furthermore, with a large bias vent 206, the pressure swing caused by breathing is reduced.

Certain characteristics of the gas supply apparatus 200 can exacerbate the pressure swing from user breathing. For example, a pressure feedback control operating to control the output of the flow generator can exaggerate the fluctuation in flow.

The valve 250 is biased toward the open condition. In the sub-therapeutic mode, the delivered supply is intended to allow the valve 250 to remain in the open condition. The pressure feedback control can have an adverse impact as the delivered supply approaches the condition that, in a steady state, would trigger the valve 250 to switch to the closed condition. In particular, within each breath cycle, the pressure control increases the output of the flow generator during inhalation relative to exhalation. This brings the flow passing the valve 250 to a critical point, thereby priming the valve 250 for closure. During the next expiration by the user, pressure rapidly increases in the circuit 202 and the "primed" or partially closed valve 250 now fully closes.

In some embodiments, the gas supply device 200 operates with a control method that reduces the occurrence of valve instability (i.e., valve flutter) caused by the fluctuation of the flow from user breathing. In particular, the control method for the gas supply device 200, at least as the supply condition approaches the transition conditions between the first mode and the second mode, is adapted to not significantly exacerbate, and preferably to alleviate, fluctuation in the particular system conditions that cause switching of the valve 250. For example, the valve 250, which will be described later, is sensitive to flow. In particular, the valve 250 is sensitive to flow from the gas supply device 200 to the user interface 204, to flow to ambient through the valve 250, or both. As the supply conditions approach levels where the valve 250 might be unstable, the control method controls the output of the gas supply device 200 according to an assessed average supply flow and a desired average flow. For example, the control of the gas supply 200 can implement a feedback control based upon average gases flow. Preferably, during this period, the method does not include a feedback control based upon pressure. This stabilises the flow, or at least removes a destabilising influence on the flow delivered by the flow generator or gas supply device 200. The flow still fluctuates with user breathing, but the controller does not take steps that exaggerate this fluctuation.

Accordingly, in some embodiments, the control results in a substantially constant low flow generator speed and/or a substantially constant low pressure generator speed and does not respond to user breathing by changing the speed of the flow generator during the breathing cycle. Because the flow is low and does not increase as much when the user inspires as it would for a pressure feedback control, the valve 250 is not "primed" for closure, and thus does not close during expiration.

In some embodiments, the pressure supplied to the patient in the sub-therapeutic mode can be varied over a substantially continuous spectrum of pressure values or among a discrete number of pressure values. The delivered pressure values can be based at least in part on feedback related to the patient and can change in response to a patient's respiration, a patient's sleep state, a breathing event experienced by the patient, and the like. In some embodiments, the control can be configured to operate in a sub-therapeutic mode to provide a delivered gas supply that can vary in pressure. For example, the pressure can vary within a sub-therapeutic pressure range in response to a patient's breathing, providing gases at an inhalation pressure during an inhalation and providing an exhalation pressure during an exhalation, the inhalation pressure being higher than the exhalation pressure and the inhalation pressure being within the sub-therapeutic pressure range. As another example, the pressure can vary within a sub-therapeutic pressure range based at least in part on feedback related to the patient's breathing such that a delivered supply can have a varying pressure within the sub-therapeutic pressure range.

In therapeutic CPAP mode (e.g., at circuit pressures above a low threshold of about 2-3 cm H2O), the controller provides feedback to the flow generator to maintain a "pressure control." During inspiration, this causes an increase in the delivered flow in order to maintain pressure, which brings the flow passing the valve 250 to a level that primes the valve 250 for closure. During the next expiration by the user, pressure rapidly increases in the circuit 202 and the "primed" or partially closed valve 250 now fully closes. Furthermore, the valve 250 is subsequently kept closed by the now continuous positive pressure (e.g., CPAP).

In some embodiments, the pressure supplied to the patient in the therapeutic mode can be varied over a substantially continuous spectrum of pressure values or among a discrete number of pressure values. The delivered pressure values can be based at least in part on feedback related to the patient and can change in response to a patient's respiration, a patient's sleep state, a breathing event experienced by the patient, and the like. In some embodiments, the control can be configured to operate in a therapeutic mode to provide a delivered gas supply that can vary in pressure. For example, the pressure can vary within a therapeutic pressure range in response to a patient's breathing, providing gases at an inhalation pressure during an inhalation and providing an exhalation pressure during an exhalation, the inhalation pressure being higher than the exhalation pressure and at least the inhalation pressure being within the therapeutic pressure range. As another example, the pressure can vary within a therapeutic pressure range based at least in part on feedback related to the patient's breathing such that a delivered supply can have a varying pressure within the therapeutic pressure range.

In effect, the above described two modes result from tuning the CPAP flow generator response to the oscillatory nature of a user's breathing and from using the resulting interaction of the pressure and flow to switch the valve mode without actually actively interacting with the valve 250 with a separate controller.

A benefit of this tuning between pressure control and flow control of the gases supply device 200 and user breathing is that, when the flow generator is switched between modes, the valve state can be controlled with minimal change in either pressure or flow alone to the user at the time of the switch.

When arranged and configured in accordance with certain features, aspects and advantages of the present invention, the system provides a sub-therapeutic pressure at the beginning of the session or at times when the apparatus considers the user to be awake. As used herein, sub-therapeutic pressures include pressures below about 4 cm H2O, preferably below about 3 cm H2O and more preferably pressures below about 1.5 cm H2O and most preferably pressures about 1 cm H2O. The sub-therapeutic mode may be selectable by a user, may be selectable by an overall control algorithm of the apparatus, or may be an automatic function at the beginning of every session of use of the apparatus. Once the user is asleep, or after an initial time-set period of sub-therapeutic delivery, the apparatus transitions and delivers a therapeutic pressure.

Preferably, sub-therapeutic pressure is provided to the user in conjunction with monitoring the flow delivered to the user. The controller of the apparatus monitors the flow delivered to the user and adjusts control of the flow generator to reduce the likelihood of or eliminate flow rates that may be insufficient to provide proper flushing of the user interface. For example, the control may reduce the likelihood of the average flow rate falling below about 10 litres per minute, preferably reduces the likelihood of the average flow rate falling below about 12 litres per minute, most preferably reduces the likelihood of the average flow rate falling below about 15 litres per minute.

For a given user interface, a particular flow rate may be considered sufficient to provide appropriate flushing. Across most user interfaces presently available, an average flow rate of about 15 litres per minute is thought to be sufficient. Whatever the chosen flow rate, while in the sub-therapeutic mode, the apparatus preferably adjusts operation of the flow generator to maintain an average flow rate close to the chosen flow rate. For example, the controller may maintain the average flow within about 5 litres per minute of this amount, or most preferably within about 2 litres per minute of this amount.

By way of example, the controller of the apparatus may control the flow generator by controlling the power input to the flow generator. In this case, in the sub-therapeutic mode, the controller may decrease power input to the flow generator when the measured average flow exceeds the desired flow range and may increase flow generator power when the average flow is below the desired range.

Alternatively or in addition, the controller may control some other parameter of the flow generator, such as, for example but without limitation, motor speed. In such a case, the controller may command an increase in motor speed if the flow is below the desired range and command a decrease in motor speed if the flow is above the desired range.

Alternatively or in addition, the flow generator may include a pressure source and a pressure regulator. In such a case, the controller may reduce the set pressure of the pressure regulator when the measured flow is above the desired range and may increase the set pressure of the pressure regulator when the flow is below the desired range. Similarly, the controller may reduce the set pressure of the pressure regulator when the measured pressure is above a desired, selected, or default range and may increase the set pressure of the pressure regulator when the measured pressure is below a desired, selected, or default range. Furthermore, the controller may change the set pressure of the pressure regulator based at least in part on feedback related to the patient, such as a patient's respiration, a patient's sleep state, a breathing disordered event, or the like. The change in the set pressure of the pressure regulator can be substantially continuous in nature (e.g., capable of assuming a range of pressure values) or it can be substantially discrete in nature (e.g., capable of assuming a pressure value among a set of pressure values). The set pressure of the pressure regulator can have a first value corresponding to a first set of criteria and a second value corresponding to a second set of criteria, such as a first pressure value when the patient is inhaling and a second pressure when the patient is exhaling. The controller can operate to vary the pressure depending at least in part on the CPAP device, the mode of operation, feedback related to the patient, or any combination of these.

In some embodiments, the controller may operate the flow generator to provide an average flow or it may be operated to provide an average low pressure. For example, the controller may control the flow generator to provide an average flow that is less than or equal to about 20 litres per minute, less than or equal to about 15 litres per minute, less than or equal to about 12 litres per minute, or less than or equal to about 10 litres per minute. The controller may control the flow generator to provide an average low pressure that is less than or equal to about 3 cm H2O, less than or equal to about 2 cm H2O, less than or equal to about 1.5 cm H2O, less than or equal to about 1 cm H2O, or less than or equal to about 0.5 cm H2O. In some embodiments, the controller can be configured to operate the flow generator based at least in part on an average flow or an average pressure. In certain embodiments, the controller can change between operating based at least in part on an average flow or an average pressure.

Advantageously, the apparatus may operate in the sub-therapeutic delivery mode during periods where the user is awake but in a therapeutic delivery mode when the user is asleep.

Accordingly, the controller may provide an initial period of operation in the sub-therapeutic mode during each session of use. This feature may also be used in an apparatus that includes functions for determining that a user is awake during periods within the session. For example, the Fisher & Paykel Healthcare HC250 device with "Sensawake" function determines instances of user arousal and reduces the delivered pressure to a pre-set awake pressure once it determines that the user may be awake. By implementing the above-described controls in such a device, the device could, after reaching the awake pressure, enter the sub-therapeutic mode.

In the sub-therapeutic mode, in some embodiments, the control aims to maintain a substantially steady flow at a flow level that is selected to be sufficient to maintain appropriate flushing of the user interface 204. As used herein, substantially steady flow means that the average flow over a period of multiple breaths (e.g., about 20 breaths) remains substantially constant or within a limited range (e.g., a range of up to about 5 litres per minute) despite changing system conditions. Changing system conditions includes, for example but without limitation, changing leak conditions due to changes in the efficiency of sealing of the user interface. By way of clarification and comparison, changes in system conditions that would see an increase in flow under a constant pressure controlled system of greater than about 5 litres per minute are responded to with a substantially steady flow in the sub-therapeutic mode.

In the sub-therapeutic mode, in some embodiments, the control aims to maintain a substantially steady low pressure at a pressure that is selected to be comfortable for a user. The system may include a pressure feedback control, or the system can include a flow generator that outputs a steady pressure at a given operating speed. For example, the control can be configured to maintain an average low pressure of less than or equal to about 3 cm H2O, less than or equal to about 2 cm H2O, less than or equal to about 1.5 cm H2O, less than or equal to about 1 cm H2O, or less than or equal to about 0.5 cm H2O. Like substantially steady flow, substantially steady low pressure refers to the average low pressure over multiple breaths. The control can be configured to provide a substantially steady low pressure while maintaining a sufficient flow to maintain appropriate flushing of the user interface 204.

In the therapeutic mode, the controller delivers a substantially steady pressure. This may include a pressure feedback control, or be the result of a flow generator with a steady pressure output for a given operating speed. Like substantially steady flow, substantially steady pressure refers to the average pressure over multiple breaths. In some embodiments, in the therapeutic mode, the controller delivers a pressure within the therapeutic pressure range that can vary rather than delivering a substantially steady pressure. In some embodiments, in the therapeutic mode, the controller delivers an inhalation pressure within the therapeutic pressure range when the patient is inhaling and an exhalation pressure when the patient is exhaling.

One non-limiting example control method that is arranged and configured in accordance with certain features, aspects and advantages of the present invention is illustrated in FIG. 1. The illustrated control method may be incorporated into an apparatus that is arranged and configured in accordance with certain features, aspects and advantages of the present invention. Other methods of control are possible; including the methods described in PCT Publication Number WO 2012/020314, filed Aug. 12, 2011 and entitled "APPARATUS AND METHOD FOR PROVIDING GASES TO A USER," which is incorporated by reference herein in its entirety. The method illustrated in FIG. 1 generally detects a sleep state of a user, enters a control mode, and varies operating parameters based at least in part on the entered control mode. For example, if the user is determined to be awake, the method enters a sub-therapeutic mode where the flow generator provides a defined, selected, or desired flow or pressure to a user. If the user is determined to be asleep, the method enters a therapeutic mode where the flow generator provides a defined, selected, or desired pressure to a user. Transitioning between control modes can include changing a size of a venting area where the venting area provides a path to ambient for gases in the system. In some embodiments, the venting area increases when the method transitions to the sub-therapeutic mode and decreases when the method transitions to the therapeutic mode. In some embodiments, the size of the venting area is determined at least in part by a position of a valve in the system. The venting area can be provided by a venting port that is preferably located as close as possible to the source of the carbon dioxide (e.g., the patient) as possible. For example, the venting port can be positioned on the mask or user interface, on a connector between a supply tube and the user interface, or in the supply tube. Transitioning between control modes can include changing a state of $CO_2$ removal from the system to maintain a level of $CO_2$ removal that is above a certain threshold level sufficient to minimize or eliminate $CO_2$ rebreathing. $CO_2$ removal can include the use of a $CO_2$ absorption arrangement and/or a sucking arrangement that is configured to flush the $CO_2$ from the system. In some embodiments, the state of $CO_2$ removal may change depending on control mode. For example the $CO_2$ removal state for a sucking arrangement may be high in the sub-therapeutic mode and/or when the patient is awake, and low when operating in the therapeutic mode and/or when the patient is asleep. Similarly, the $CO_2$ source may be more exposed to a $CO_2$ absorber when the device is operating in the sub-therapeutic mode and/or the patient is awake, less or not exposed to the absorber when operating in the therapeutic mode and/or patient is asleep. The $CO_2$ removal can be provided by a $CO_2$ removal arrangement that is preferably located as close as possible to the source of the carbon dioxide (e.g., the patient) as possible. For example, the $CO_2$ removal arrangement can be positioned on the mask or user interface, on a connector between a supply tube and the user interface, or in the supply tube. The illustrated method for implementing the sub-therapeutic mode commences at 100 and may be triggered by a conscious user choice, such as, for example but without limitation, by selecting a control mode using the electrical user control interface. In some embodiments, the mode may be an initial starting mode for the apparatus or may be commenced by the apparatus according to a wider control strategy.

After starting, a control command issues to the flow generator to cause the flow generator to operate at an initial level. See 102. For example but without limitation, the controller can supply a command motor speed as an input to the flow generator and a motor of the flow generator can be speed-controlled to the command motor speed. In some applications, the apparatus may provide one or more of one or more command pressure values, one or more command flow values or one or more motor power inputs as input parameters. Preferably, the initial command input parameter for the flow generator is at a level that would usually provide a sub-therapeutic pressure between about 0.2 cm H2O and 2 cm H2O with a user interface correctly fitted. In the illustrated example, the motor speed is set to about 4000 rpm.

An evaluation then is made regarding whether the user is asleep. See 104. Preferably, the controller maintains a value representing the controller's belief that the user is asleep or awake. This value may be a probability assessed by the controller of whether the user is asleep or awake. The value can be assessed against criteria to decide whether to proceed on the basis that the user is asleep or to proceed on the basis that the user is awake. The value may be maintained by, for example but without limitation, assessing recent breathing patterns of the user, assessing recent history of apneaic events and/or obstructed breathing of the user. This may be examined over a time period, such as, for example but without limitation, the preceding few minutes, ten minutes or other similar time period. Any suitable methods of making a determination that the user is asleep or is awake can be used. Some suitable methods are described in other patent publications, for example, U.S. Pat. No. 6,988,994 and U.S. 2008/0092894, which are hereby incorporated by reference in their entirety.

The "asleep" assessments, and the maintenance of a sleeping value, may be made according to a separate control program running in parallel with the control program described with reference to FIG. 1. The separate control programs may be generally separate subroutine routines that may be executed sequentially in a given execution cycle but also may operate in parallel. If a separate control program is used, the control program of FIG. 1 will determine whether the user is asleep or awake based on an input parameter maintained or output by the other control program.

If the program determines that the user is asleep, then a therapeutic pressure is applied. See 106. The application of therapeutic pressure application may begin, for example, by immediately proceeding to a predetermined starting point pressure (e.g., about 3 or 4 cm H2O or greater) for therapy. This pressure may be a preset of the device or may be a variable pressure set by a physician. In some configurations, the method may proceed directly to a full treatment pressure, for example, a treatment pressure prescribed by a physician and preconfigured in the device. In some configurations, the control method may proceed to an automatic titrating mode that commences at a starting therapeutic pressure and that adjusts the supply pressure according to breathing events, such as apneas, hypopneas, flow obstructions, and periods of normal breathing.

In the therapeutic mode, the control method preferably seeks to maintain a substantially steady pressure. For example, the controller may control the flow generator based on input from a pressure sensor that senses pressure in the user interface 204 using feedback from the pressure sensor to control the speed of, or power input to, the flow generator, or to control the input parameter of a pressure regulator. The pressure in the patient interface 204 can be sensed in any suitable manner. For example, the pressure can be sensed either by a sensor that is positioned directly in the user interface 204 or by a sensor that interfaces with a part of the flow path to the user interface 204 that is downstream of the flow generator.

In some embodiments, the substantially steady pressure can be generated using a fan having a substantially constant pressure output for a given fan speed across a wide range of flow or from a pressure regulator, such as a self-regulating pressure regulator for example but without limitation, that may, for example but without limitation, use a mechanically operative feedback control to adjust the pressure output according to a particular input parameter.

In some embodiments, the substantially steady pressure can affect a size of a venting area of the system. For example, an increase in pressure can decrease the size of the venting area, a constant pressure can maintain the size of the venting area, and a decrease in pressure can increase the size of the venting area. In some embodiments, the system includes an adaptable venting arrangement that moves between two positions corresponding to a therapeutic mode and a sub-therapeutic mode, where the two positions affect the size of the venting area. For example, when transitioning to the therapeutic mode, the adaptable venting arrangement can decrease the size of the venting area (compared to an initial state or sub-therapeutic mode) due at least in part to an increase in pressure and/or flow.

The therapeutic mode (e.g., positive pressure, CPAP or autotitrating) may proceed according to any suitable treatment program and/or method. Control of the particular applied pressure in these methods may be by a separate control program or routine running in parallel or otherwise in conjunction with the control program described with reference to FIG. 1.

With reference again to FIG. 1, the illustrated control method begins looping to determine when a user awakens so that the machine can respond to the awakening of the user. See 108. For example, the control loop depends upon the output of the separate control loop that determines on a continuous basis an awakened state of the user.

As shown at 110, if the user is still asleep, the method continues to apply the therapeutic treatment pressure. See 106. The control loop 106, 108, 110 continues until it is determined that the user is awake. If it is determined that the user is awake, the method commences the sub-therapeutic mode. For example but without limitation, the sub-therapeutic mode can be commenced by changing the input parameter to the flow generator so that the flow generator provides gases at a sub-therapeutic pressure. See 102. In some embodiments, when transitioning to the sub-therapeutic mode from the therapeutic mode, the venting area of the system increases in size. For example, the adaptable venting arrangement can increase the size of the venting area (compared to a therapeutic mode) due at least in part to a decrease in pressure and/or flow.

Once again, the method determines whether the user is awake. See 104. If the user is awake, the method proceeds to measure the flow. See 118. At 118, 120, 124, the measure of the flow is compared against a preferred flow range and, at 124, 128, the input parameter sent to the flow generator is adjusted accordingly. Preferably, the method checks (see 118) an assessed flow against a lower flow value. For example, the method checks whether the recent average flow (e.g., the average flow over the preceding 5 breaths, 10 breaths, 10 seconds, 30 seconds or a similar period) is less than a lower threshold (e.g., about 15 L/min).

The lower threshold may be a fixed predetermined value. For example, the value may be chosen to be suitable for all suitable user interfaces. In some embodiments, the lower threshold value may be a settable value, for example, so that it can be set according to a particular user interface used by the user. In some embodiments, the lower threshold value may be taken from a table of values based on a determined identity of the user interface or might be assessed for a particular interface in a test mode performed by the apparatus. In the simplest case, a fixed preset flow value, such as a lower limit flow value of about 15 litres per minute, is thought sufficient to provide a significant improvement in comfort over prior art apparatus without compromising safety.

If the assessed average flow is less than the lower threshold level, the control method adjusts the input parameter to the flow generator to increase the output of the flow generator. For example, the controller may increase a demand motor speed. See 124.

An additional check may be provided after determining that the average flow is below the lower control limit. See 122. The additional check determines whether the pressure has reached a therapeutic pressure level. While shown occurring after the lower control limit check (see 118), the pressure level check can occur at any suitable time. For example, in the illustrated method, the additional check may be conducted between the lower threshold level check and the output increase. See 122, 118, 124. Preferably, the method checks an assessed pressure in the user supply against a pressure threshold, for example but without limitation, 4 cm H2O. See 122. Where the flow is assessed below the lower limit at 118 and the pressure is assessed above the threshold at 122, the method preferably proceeds to leave the sub-therapeutic mode and switch control to the therapeutic mode, as discussed above with reference to 106.

In some embodiments, in the sub-therapeutic mode, the control method measures the pressure and controls the flow generator to provide gases at a sub-therapeutic pressure. The flow generator can be operated to provide gases at an average low pressure that is within a pressure range or below a pressure upper threshold. Similar to the method for controlling the flow generator using an assessed flow described above, the control method can receive an assessed pressure and adjust an input parameter sent to the flow generator to achieve a targeted pressure that is within the pressure range or below the pressure upper threshold.

The control method may also set a fault condition, for example at 126. The controller may provide an indication of the fault condition as an alert on the electrical user control interface of the device or record the fault condition in a session data log maintained by the device for later review by the user, physician or other interested party.

Where the control method increases the flow generator output at 124, this is, for example, by increasing the demand parameter for the flow generator. The increase may be a fixed predetermined incremental increase, an incremental increase that varies according to the present value of the parameter, or an incremental increase that varies according to the difference between the present value of the average flow and the desired flow range or the difference between the present value of the average pressure and the desired pressure range. For example but without limitation, the new input parameter (e.g., the new motor speed in a control motor speed embodiment) may be a function of the present motor speed, the present average flow value, a desired average flow value, the present average pressure, and a desired average low pressure.

Alternatively, if the average flow value is above the minimum range value (see 118), the control method checks the average flow value against an upper flow value threshold for the range. See 120. Preferably, to maintain a low sub-therapeutic pressure, the flow range between the minimum value and maximum value is kept to a minimum. For example, the flow range may be about 5 litres per minute or less, preferably about 3 litres per minute or less, and most preferably about 2 litres per minute or less.

Alternatively, both upward and downward adjustment of the control parameter for the flow generator can be made based on a single desired average flow value or based on a single desired average low pressure value. This is particularly suitable if an adjustment increment for the control parameter is a function of the difference between the present average flow or pressure value and the desired average flow or pressure value. In this method, for example, the check against the upper flow value threshold (see 120) can be removed with the method proceeding directly from 118 to 128 in the case where the average flow value is not less than the desired flow value. This arrangement will lead to frequent adjustment of the motor input parameter, but if the frequent adjustments are small, they may not be significant. Similarly, a configuration can be used that does not have a lower flow threshold.

If the average flow or pressure is determined to be above the preferred range at 120 (or at 118 according to the modified method discussed above), then at 128 the control method decreases the input parameter to the flow generator. For example, the decrease may be a predetermined decrement, or a decrement variable according to the present average flow or pressure, the present value of the input parameter or the difference between the present average flow or pressure and the desired average flow or pressure range. The method then returns to 104. The method set forth at 104, 118, 124, 120 and 128 broadly constitute a feedback control controlling the output of the flow generator according to a desired flow rate or pressure (or desired flow rate or pressure range) and based on an assessed average flow rate value or an assessed average pressure value.

In some embodiments, transitions between operating modes can be made in synchrony with a breath of a user. The control of the flow generator can increase or decrease pressure and/or flow corresponding to a change in operating mode and the control can make the changes in synchrony with an inspiration of the user, an expiration of the user, or in synchrony with both an inspiration and an expiration of the user, as described in greater detail herein. For example, if the user is determined to be asleep, the control method can transition to the therapeutic mode and increase the average pressure in synchrony with an inhalation of the user. In some configurations, transitioning between control modes in synchrony with a user's respiration corresponds to increasing or decreasing a venting area of an adaptable venting arrangement, as described in greater detail herein with reference to FIGS. 14a to 14c. In some embodiments, transitioning from one pressure to another pressure is initialized during a particular breath state. For example, transitioning from a sub-therapeutic mode to a therapeutic mode can be achieved synchronously with the breath state by beginning to speed up the blower motor at the peak of patient exhalation. In this manner, the motor would have sufficiently sped up to deliver therapeutic pressure just as the patient begins to inhale. In this way, transitioning between modes in synchrony with a breathing state can include a transition that begins during a first breathing state and finishes during the subsequent breathing state (e.g., begins during an exhale and ends during the subsequent inhale).

Figure 3A:
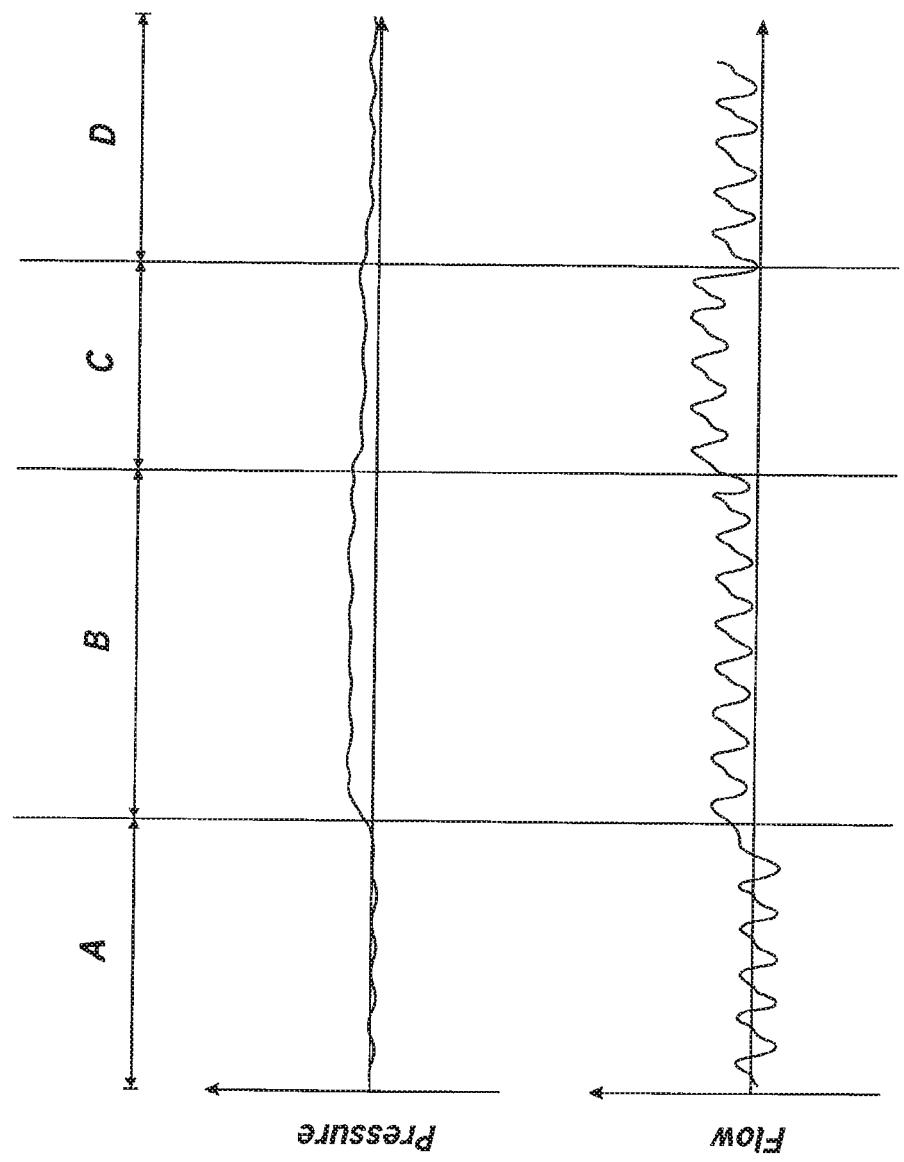

FIGS. 3A and 3B illustrate the effect of a control operating in accordance with certain features, aspects and advantages of the present invention. These plots are only intended to be representative and have been simplified accordingly. Section A of FIG. 3A shows normal breathing at the beginning of a session. The pressure is low (e.g., approximately 0 cm H2O) however the flow is averaging less than about 15 l/min.

Section B of FIG. 3A shows the device responding to the low flow rate in Section A, which results in increased flow generator speed (e.g., 118, 124 in FIG. 1), thereby causing the flow and pressure to rise.

Section C of FIG. 3A shows a leak being introduced (e.g., a mask leak occurs) and the level of flow increasing accordingly. The pressure drops slightly due to the leak.

Section D of FIG. 3A shows the algorithm responding to the increased level of flow by reducing the speed of the flow generator until the flow is again averaging approximately 15 l/min (e.g., 120, 128 in FIG. 1). The drop in speed further reduces the pressure.

Section E of FIG. 3B shows normal breathing.

Section F of FIG. 3B shows a user having an apnoea. The apnoea is shown by the flattening of the flow signal.

Section G of FIG. 3B shows that, in response to the event in Section F of FIG. 3B, the device raises the pressure and normal breathing resumes (e.g., 104, 106 in FIG. 1).

The chaotic flow signal at the end of Section G indicates that the user has awoken and, at Section H, the pressure is reduced accordingly until the approximately 15 l/min average flow is maintained again (e.g., 108, 102 in FIG. 1).

With reference again to FIG. 2, FIG. 2 presents a block diagram illustrating an embodiment of a breathing gases supply system that is arranged and configured in accordance with certain features, aspects and advantages of the present invention. The full system includes the gas supply device 200, which is an apparatus for delivering a supply of breathing gases, the supply conduit 202 and the user interface 204. As discussed above, the flow diversion device 250 can be located at, on or adjacent the user interface 204. Preferably, the flow diversion device 250 is in one of these locations because it allows venting to the atmosphere under certain operating conditions, which limits carbon dioxide rebreathing and provides oxygen. The supply conduit 202 extends from an outlet of the gases supply device 200 to the user interface 204. In some embodiments, the breathing gases supply system includes a CO2 removal arrangement configured to remove carbon dioxide from the gases supply system. Preferably, the CO2 removal arrangement can be positioned near the patient, such as in the supply conduit 202 or at the user interface 204.

The user interface preferably includes the bias flow vent 206 that allows a controlled leak from the user interface 204. The controlled leak allows the inside of the user interface 204 to be continuously flushed by fresh gases supplied by the supply device 200. The user interface 204 may comprise any of the many types of typical user interface for PAP delivery, including but not limited to, for example but without limitation, nasal masks, full face masks, oral masks, oral interfaces, nasal pillows, nasal seals or nasal cannulas.

The vent 206 may be located directly on the user interface 204, the vent 206 may be located adjacent the user interface 204 on a connector between the user interface 204 and the supply tube 202, or the vent 206 may be located through the wall of the supply tube 202 at a location close to the user interface 204, for example but without limitation.

The CO2 removal arrangement, if included, can be located on the user interface 204, adjacent the user interface 204 on a connector between the user interface 204 and the supply tube 202, or it may be located at the wall of the supply tube 202 at a location close to the user interface, for example but without limitation. The CO2 removal arrangement can include, for example, a CO2 absorption arrangement and/or a CO2 sucking arrangement.

The illustrated supply apparatus 200 includes a flow generator, which can comprise a fan 210 driven by an electric motor 212. Air is drawn through an inlet 214 in the housing of the apparatus by the fan 210. Pressurised air leaves the fan 210 and is supplied to the user through the supply conduit 202, for example. In some embodiments, controllable flow generators may draw on a source of high pressure gas and regulate a flow of gas from the high pressure source.

The apparatus 200 may include a humidifier 216. In some embodiments, the humidifier 216 comprises a pass-over humidifier where air passing through a humidifier chamber picks up a quantity of water vapour from a water supply contained in a reservoir 218. The water reservoir 218 may be heated by a heater 220. The humidifier 216 may be integrated within the same housing as the flow generator 210 or may be a separate component that can be used as an option.

The heater 220 and the motor 212 are supplied with power from a power supply 222. The amount of power to the motor 212 and the amount of power to the heater 220 can be controlled by outputs of a controller 224. The controller 224 is also supplied with power from the power supply 222. The controller 224 receives input from an electrical user control interface 226, for example but without limitation. The controller 224 preferably includes an embedded microcomputer with stored control programs or the like.

The controller 224 is also provided with an interface 228 that is used to connect with an external data source. For example but without limitation, the external data source may be a communication interface, such as a modem, or may be an interface to an external memory, such as a smart card, disk drive, flash memory or the like. For generic use, the interface 228 may be any suitable data communication port that is arranged and configured in accordance with any of the many available standards (e.g., a universal serial bus (USB) port). The interface 228 can be used for connecting a wide range of peripheral devices. In some configurations, the interface 228 can be replaced by or augmented with a wireless communication device (e.g., Bluetooth, Wi-Fi, etc.).

The controller 224 preferably includes interfaces for receiving input from the electrical user control interface 226 and for receiving input from one or more sensors. The sensors can include a flow sensor 230 and a pressure sensor 232. The pressure sensor 232 can be positioned downstream of the fan 210. The flow sensor 230 can be positioned upstream or downstream of the fan 210.

The apparatus preferably is configured to perform control methods in the form of control programs executable by a microcomputer of the controller 224, for example but without limitation. In some embodiments, the controller 224 may comprise a fixed electronic circuit implementing control programs, a programmed logic circuit (e.g., an FPGA) implementing control programs or the like. Any suitable Electronic circuits and logic circuits implementing the control program may be used. In fact, all of the methods and processes described herein may be embodied in, and fully automated via, software code modules executed by one or more general purpose computers or processors. The code modules may be stored in any type of computer-readable medium or other computer storage device. Some or all of the methods may be embodied in specialized computer hardware. In addition, the components referred to herein may be implemented in hardware, software, firmware, or a combination thereof.

The illustrated apparatus, which preferably operates according to the control methods described herein, provides a sub-therapeutic mode of operation that is applied to the user while the user is awake. Breathing at this lower pressure may be less arduous than at the low therapeutic pressures applied at the commencement of therapy by other devices. This may be more comfortable and more pleasant for the end user, thereby improving therapy acceptance and compliance. At the same time, a minimum flow through the supply conduit 202 is provided to supply an adequate flow of fresh breathing gases to the interface 204 to flush the user interface 204 and reduce the likelihood of user re-breathing.

As described above, upon the detection of sleep, or a breathing disorder event, the apparatus will increase the delivered pressure to a predetermined or automatically determined therapeutic level at a comfortable and tolerable rate. When sleep or a breathing disorder event occurs, the user can be assumed to be asleep. Accordingly, the user should not be aware of or consciously experience the required higher therapeutic pressures, again thereby hopefully improving compliance.

Preferably, if the user wakes during the sleep session, the apparatus will revert to the sub-therapeutic state. The now conscious user will not experience, or will only experience for a limited time, the higher therapeutic pressures that are supplied while they are asleep because the apparatus returns to the sub-therapeutic state. This should also increase user compliance, particularly in the later stages of a sleep session, where otherwise the user may remove and cast aside the user interface before trying to return to sleep.

The method as described may be adapted by further variations. A few of these variations have been described above and several more will be described below. This is not an exhaustive summary and many further variations and alternatives are possible without departing from the scope of certain features, aspects and advantages of the present invention.

According to one variation, the apparatus may monitor one or more of the flow, the pressure, or other parameters that may indicate user respiratory rate. From the user respiratory rate, the controller may determine increased respiratory rate or increased breath volume. In the presence of increased respiratory rate or breath volume, or both, the controller 224 may increase the desired flow level in the sub-therapeutic mode. Increased respiratory rate or increased breath volume may be indicative of carbon dioxide rebreathing. Increasing the desired flow level in the sub-therapeutic mode may adapt the sub-therapeutic mode flow level to account for prevailing system conditions. The controller 224 may further filter this response according to the present user sleep state, which may help to reduce the likelihood of false positives due to dreaming, mask leaks and the like.

According to a further variation, one or more routines may be provided to check for occurrences of negative pressure in the user interface 204 during the sub-therapeutic supply mode. For example, the control program of the controller 224 may measure, derive or calculate a pressure in the mask or interface 204 on a continuous basis, or at least at a point in time or points in time during user inhalation. If the mask or interface pressure drops below a predetermined threshold (e.g., about 0 cm H2O or slightly below about 0 cm H2O) during user inhalation, then the control program adapts the delivered therapy in an effort to reduce or eliminate these subzero pressures. These negative pressures may otherwise be experienced by the user as an undesirable feeling of being starved of air. The control program may apply the adaption instantaneously (e.g., applied within a breath cycle) or over a longer time period (e.g., adjusting an inhalation boost parameter periodically).

The controller 224 may obtain the pressure in the interface 204 by providing a sensor at the interface 204 to receive direct measurements of the internal pressure at the user interface. In some embodiments, the controller 224 may predict the pressure at the interface 204 from a measurement of the pressure of the delivered flow leaving the flow generator 210 (e.g., before or after the humidifier 216) and a predicted pressure drop between the location of the measurement and the interface 204 (e.g., across the length of the supply conduit). The control program can predict the pressure drop on the basis of the instantaneous flow along the conduit 202, for example. The control program can assume the conduit 202 has a certain flow resistance or can calculate the resistance of the conduit 202 or other assembly of components by implementing a pre-therapy test comparing delivered pressure and flow with no user interface connected to the conduit. The control program may implement any suitable method.

The control program may adapt the sub-therapeutic supply in a number of ways. One option would be to boost the target average flow. However, boosting the target average flow may boost the peak pressures during user exhalation and will boost the overall average pressure, thereby reducing some of the comfort advantages intended.

In some configurations, the controller can boost the supplied flow on user inhalation, for example, by increasing the output of the flow generator at the start of inhalation and subsequently reducing the output of the flow generator back to a lower level for exhalation. The control program may monitor user respiration to determine the start and end of inhalation by monitoring the variation in delivered flow or pressure on a breath-by-breath basis. While the average flow over multiple breaths is maintained substantially constant, the flow varies in an essentially sinusoidal manner in time with the user breathing. The flow is higher during inhalation than during exhalation. The control program can determine the inhalation phase from this variation.

According to another variation, the control program (e.g., the control program run by the controller) may provide a settable parameter providing for a boosted inhalation flow. For example, a settable parameter may be provided on a scale. A value of 0 indicates no boost to the input parameter for the flow generator during inhalation relative to exhalation. A progressively higher value indicates a progressively higher boost to the input parameter of the flow generator used during inhalation relative to exhalation. The user or the user's physician could set the parameter according to measurement, according to a qualitative assessment of total breathing volume of the user, or according to reported instances of breathlessness during the sub-therapeutic supply phase.

The controller 224, while implementing the sub-therapeutic phase, may control a baseline input parameter to the flow generator 210 according to the average delivered flow and, during periods of inhalation or periods of exhalation, may control the input parameter to the flow generator 210 according to a combination of the baseline parameter and the settable inhalation boost. According to this, the baseline could be applied during inhalation or exhalation. If the baseline is applied during exhalation, then the inhalation parameter is a boost above the baseline. Where the baseline is applied during inhalation, the exhalation pressure is a reduction below the baseline according to the set parameter. By boosting the flow (i.e., boosting beyond the normal fluctuation provided by the user breathing alone) during inhalation relative to exhalation, these variations reduce the likelihood of any feeling of starvation at the interface 204.

According to a further variation, the control method may include control of humidification of the breathing gases (e.g., by varying a power input to a humidification heater 220) such that humidification delivery in the sub-therapeutic mode is controlled independently of humidification delivery in therapeutic modes. For example, in the sub-therapeutic mode, the controller may reduce or disable humidification (e.g., by reducing or turning off power to the humidification heater 220).

According to a further variation, the apparatus may include a user selectable, or automatically initiated, test sequence. According to the test sequence, the control program causes the flow generator 210, 212 to deliver a controlled therapeutic pressure for a period of time. It is intended that the user will not consciously experience high pressures at the interface 204. The test sequence will provide an opportunity for the user to ensure that the mask is fitted correctly. The control program may provide for a test sequence selectable by a user at the electronic user control interface, or may provide for the test sequence to automatically commence at the beginning of the session, or both. The test sequence may provide for a pressure delivery at a preset minimum therapeutic pressure, a preset maximum therapeutic pressure, a preset test pressure, or another pressure selected according to previous use of the device (e.g., a 95th percentile pressure established from previous sessions).

In some configurations of the apparatus, such as described with reference to FIG. 2, the apparatus includes the flow sensor 230 and the pressure sensor 232. Each sensor, 230, 232 may be of any suitable type. For example, the flow sensor 230 may be a differential pressure sensor operating in conjunction with a flow restriction. In that case, parts of the differential pressure sensor may double as the pressure sensor. In some applications, an assessed pressure may be derived independently by a discreet pressure sensor. In some applications, the delivered pressure may be inferred from blower speed, or calculated from a sensed flow and blower speed, for example but without limitation. An assessment of the delivered pressure may also account for an estimated pressure drop between the PAP apparatus and the user, for example, by accounting for a pressure drop along the conduit 202 according to a measured flow. In addition, where the pressure sensor 232 is present, flow can be inferred from blower speed and the output of a pressure sensor rather than using a separate flow sensor. Otherwise, any suitable flow sensor can be used.

Figure 9A:
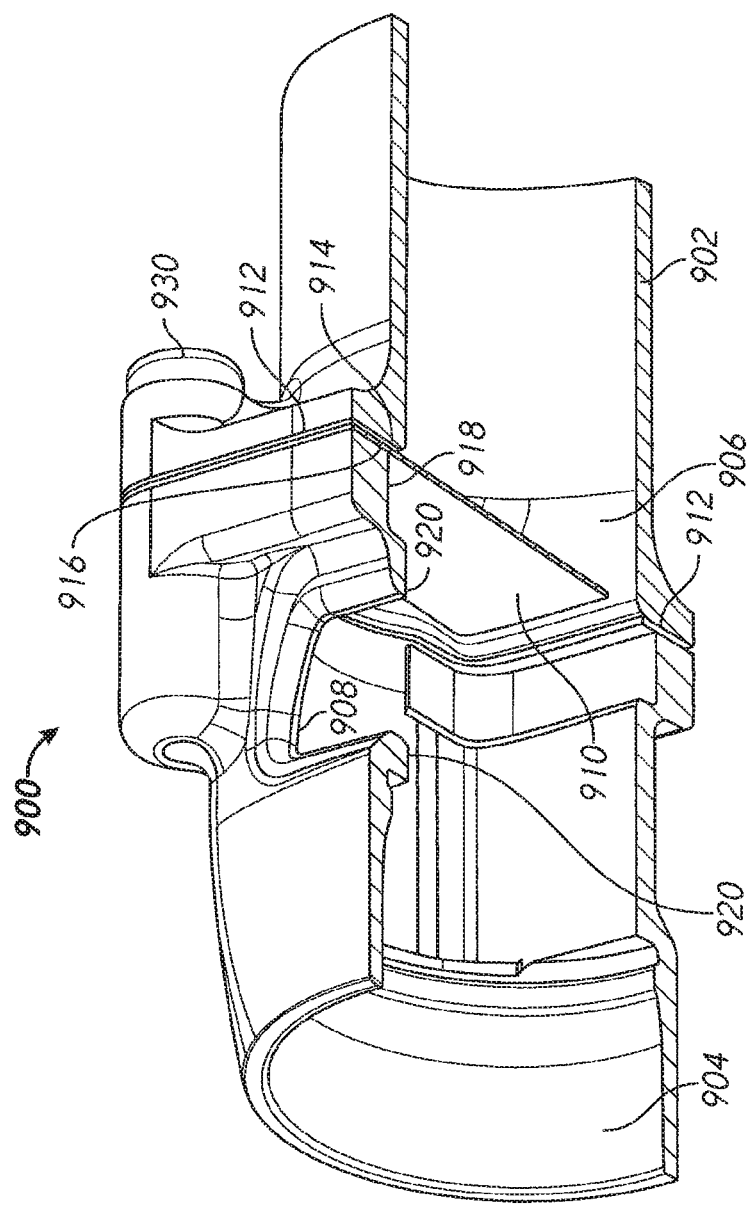
FIG. 9A is a cross-sectional side elevation of a flow diverting valve that is arranged and configured in accordance with certain features, aspects and advantages of the present invention.
Figure 9B:
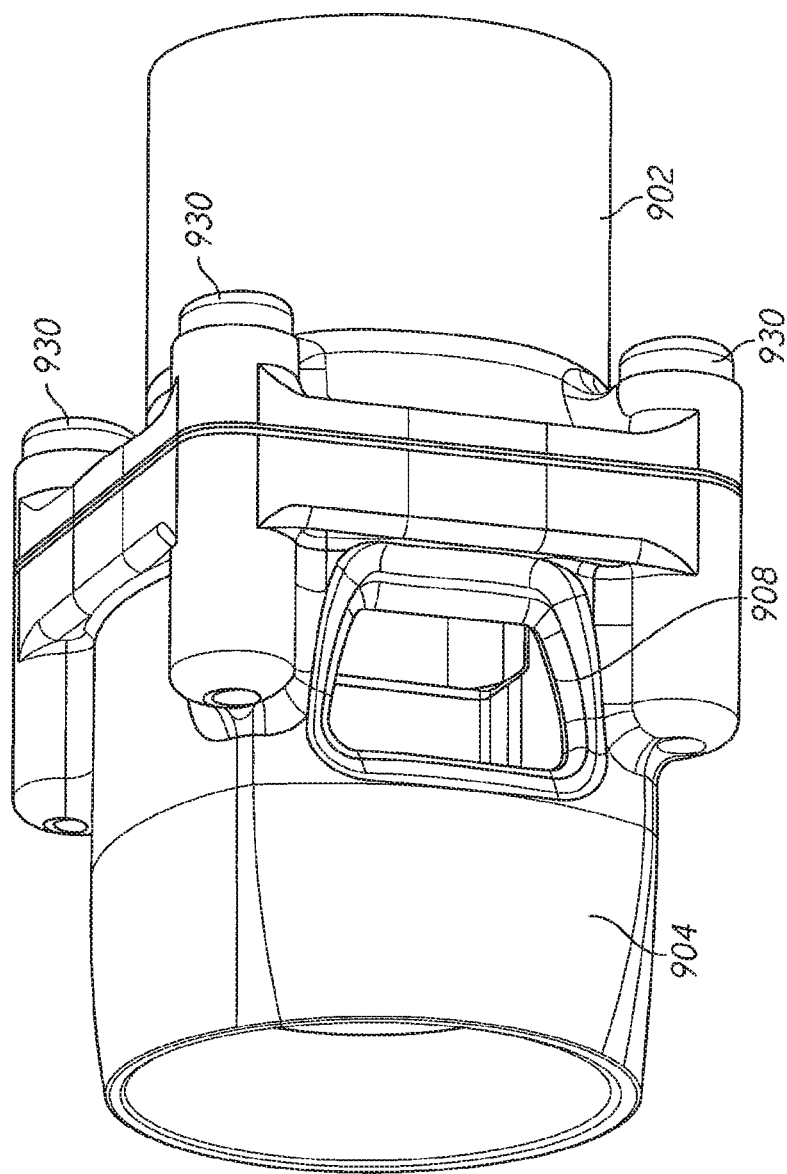
FIG. 9B is a perspective view of the valve of FIG. 9A.
Figure 9C:
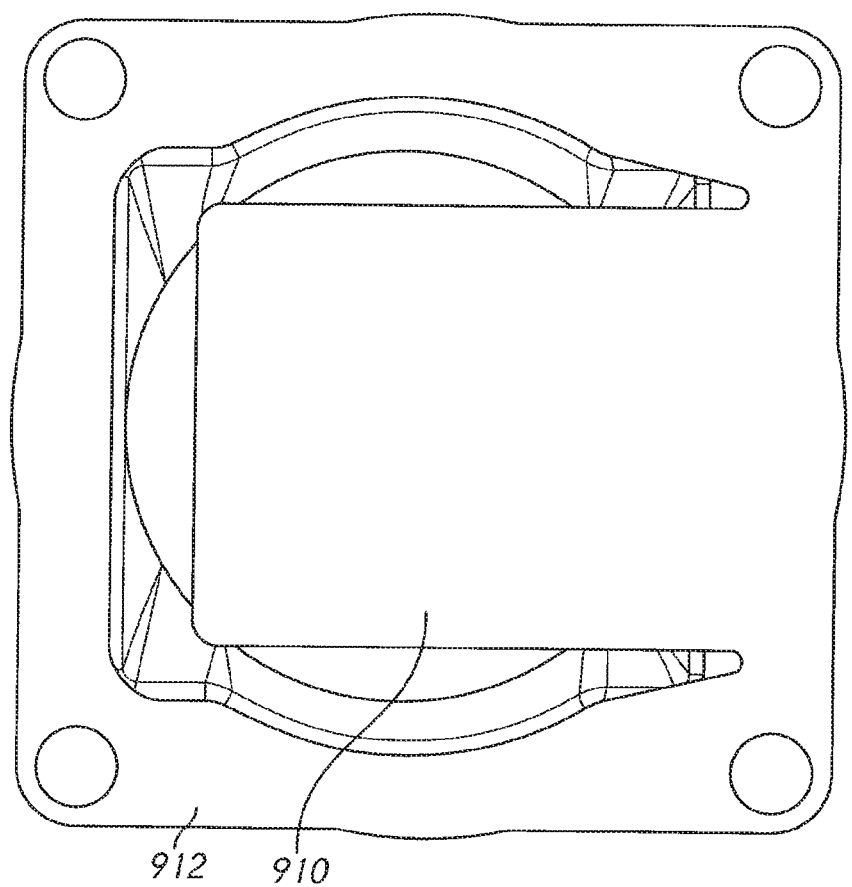
FIG. 9C is a cross-section of the value of FIG. 9A showing a profile of the valve.

FIG. 9A to FIG. 9C illustrate a flow diversion device 900 that can be used in an implementation of a system that is arranged and configured in accordance with certain features, aspects and advantages of the present invention. The flow diversion device 900 can be arranged as a connector for simplicity of assembly with other pre-existing components.

The illustrated flow diversion device 900 includes an inlet portion 902 and an outlet portion 904. In some embodiments, the inlet portion 902 comprises an inlet connector portion 902 and the outlet portion 904 comprises an outlet connector portion 904. The inlet connector portion 902 includes an external tapered connecting surface. The external tapered connecting surface can be a standard taper. The outlet connector portion 904 includes an internal tapered connecting surface. The internal tapered connecting surface is used to secure a swivel connector, for example but without limitation. Other configurations are possible.

A flow passage or bore is provided through a body of the flow diversion device 900 from the inlet end of the inlet portion 902 to the outlet end of the outlet portion 904. A central portion 906 comprises a flow port 908 extending through a wall of the flow diversion device 900. The flow path through the flow diversion device 900 can communicate with the ambient surroundings through the port 908.

A flexible valve member 910 extends into the flow path at a location between the inlet to the inlet portion 902 and the port 908. An internal perimeter surface 920 surrounding the port 908 may act as a land or valve seat for when the flow diversion device 900 is in the closed condition. In the closed condition, a valve flap cuts off flow from inside the user interface 204 to ambient surroundings through the port 908.

Flow through the flow diversion device 900 from the inlet of the inlet portion 902 to the outlet of the outlet portion 904 pushes against the valve member 910, which urges the valve member 910 toward the closed condition. Flow passing from the outlet portion 904 to the inlet portion 902 (e.g., in the case of user exhalation) pushes against the valve member 910 to urge it toward the inlet portion 902 and the opened condition.

The valve member 910 preferably is cantilevered from the inside surface of the wall forming the flow passage. The valve member 910 may be able to flex toward or away from the closed condition by bending adjacent its connection with the wall or by bending along its length. In some configurations, the valve member 910, when in the opened condition (i.e., extending into the flow path between the inlet and the outlet), the valve member 910 can bend toward the user during inhalation and/or toward the flow generator during exhalation. In the illustrated flow diversion device 900, the secured end of the valve member 910 is clamped between two portions of the flow diversion device 900. For example, a base of the valve member 910 may be clamped between an end surface 914 of the inlet portion 902 and an end surface 916 of the outlet portion 904.

With reference to FIG. 9C, the valve member 910 may be formed integrally with a gasket 912. The gasket 912 can be a perimeter gasket. In some configurations, the gasket 912 only extends a portion of the full perimeter of the flow diversion device 900. The gasket 912 may be sandwiched between the end surfaces 914, 916 around the circumference of the connector 900. In the illustrated configuration, the two parts containing the end surfaces 914, 916 of the flow diversion device 900 are secured together by a plurality of screws 930. In other configurations, the two portions of the flow diversion device 900 can be secured by snap fit connection, adhesives, over-moulding, ultrasonic welding or the like. In some applications, the valve flap 910 is a removable component.

Where the valve flap 910 displaces by bending along its length, the land or valve seat 920 for the port 908 preferably is disposed on or near a plane that is spaced away from the embedded portion of the valve member. In other words, the land or valve seat 920 is offset in a transverse direction of the illustrated passage such that, as the valve member 910 bends to cover the port 908, a portion of the valve member 910 toward the free end of the valve member 910 can sit against the land 920 and substantially close the outlet port 908. The offset advantageously allows the valve member 910 to easily cover at least a portion of the outlet port 908 by simply bending about one bending location. In some applications, the offset allows the valve member 910 to substantially cover the outlet port 908 without the valve member 910 having to adopt a convoluted shape.

In a simple arrangement, the offset is provided by a stepback or offset 918 displaced away from the land 920. Instead of the stepback 918, a curved surface may be provided between the base of the valve member 910 where it embeds in the wall of the flow diversion device 900 and the port 908. The curved surface may match the expected curvature of the valve member 910 when it is deflected by prevailing conditions to substantially cover the outlet port 908.

In some configurations, the flow passage cross-section in the region of the valve member 910 is a substantially square or rectangular cross-section and the valve member 910 comprises a matching but slightly smaller profile (e.g., square or rectangular shape). Preferably, a significant gap or space is provided between at least a portion of the perimeter of the valve member 910 and the inner surface of the wall defining the flow passage. The gap or space provides a significant flow path through the location of the valve 910 with the valve 910 in the open condition, as illustrated in FIG. 9A. By way of example, with reference to FIG. 9C, the overall flow passage of the illustrated valve can have a cross-sectional area of about 470 mm2. The valve flap can be about 16 mm wide and about 19 mm long such that it defines an area of about 300 mm2. Thus, the opening between the perimeter of the valve flap and the inner surface of the wall of the flow passage can be about 165 mm2. According to such a configuration, with the valve 910 in the open position, a substantial portion (e.g., slightly more than ⅓) of the flow path remains unimpinged by the valve. In some embodiments, the valve 910 may occlude about 50%, about 60%, about 70% or about 80% of the flow path. In other words, the valve 910 may occlude between about 50% and about 80% of the flow path. Preferably, the valve 910 may occlude between about 50% and 70% of the flow path. In some embodiments, the valve 910 may occlude between about 60% and about 80% of the flow path. In some embodiments, the valve 910 may occlude between about 60% and about 70% of the flow path. In some embodiments, the valve 910 may occlude about 65% of the flow path.

The preferred valve flap 910 is very flexible and can be formed as a single leaf of a suitable, flexible polymeric material. For example, the valve flap 910 in the illustrated valve can be made from LSR silicone with a Shore A hardness of about 40. The illustrated valve flap 910 can be moulded with a thickness of about 0.45 mm. The 0.45 mm thickness provides a sufficiently thin valve flap, wherein the valve flap 910 had a surface dimension of about 16 mm wide by about 19 mm long. Other sizes also can be used.

The valve port 908 is located downstream of the valve flap 910. The valve port 908 may be, for example, about 5 mm downstream to about 10 mm downstream, and preferably about 7 mm downstream, of the valve flap 910. The illustrated port 908 is approximately trapezoidal in perimeter shape, with the shorter of the two parallel sides being closer to the valve flap 910. In the illustrated embodiment shown in FIGS. 9A-9C, the port 908 has an area of about 86 mm2, a perimeter of about 36 mm2, an overall width of about 11 mm and an overall length of 8 mm. Thus, the area of the port 908 may be between about 10% and about 50% of the flow path, and most preferably between about 15% and about 25% of the area of the flow path.

Figure 10A:
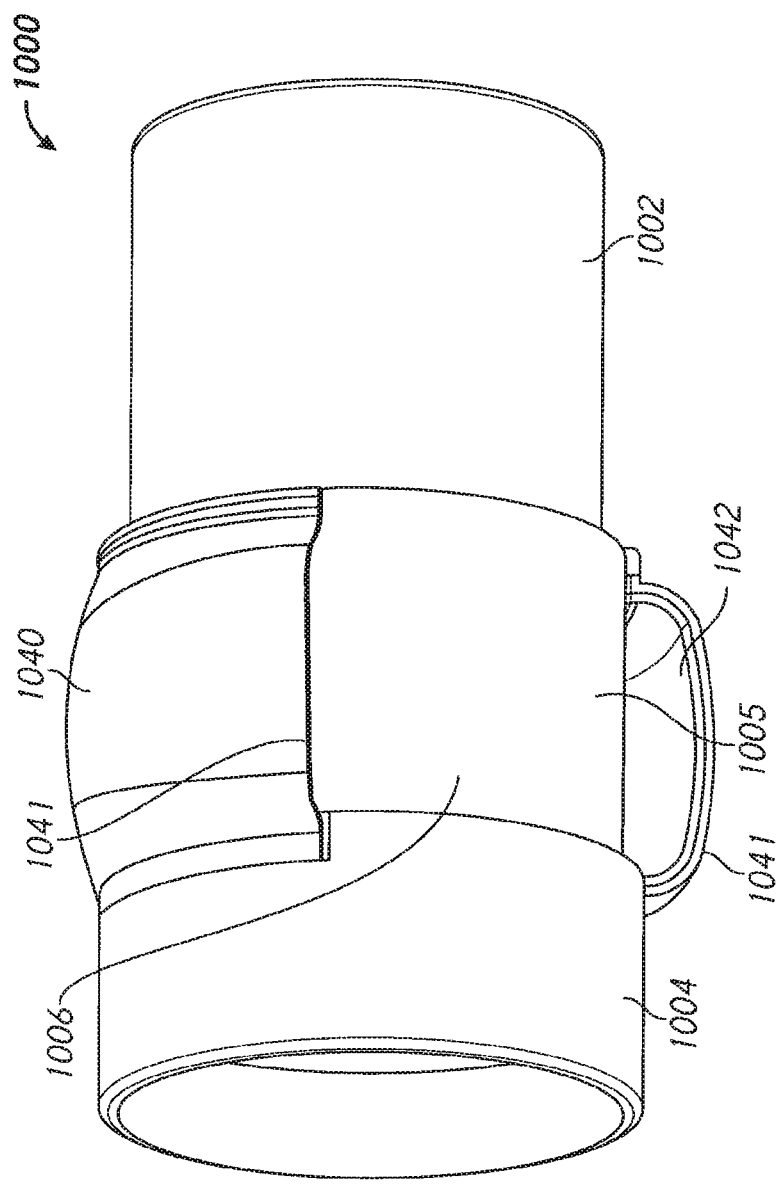
FIG. 10A is a side perspective view of a flow diverting valve that is arranged and configured in accordance with certain features, aspects and advantages of the present invention.
Figure 10B:
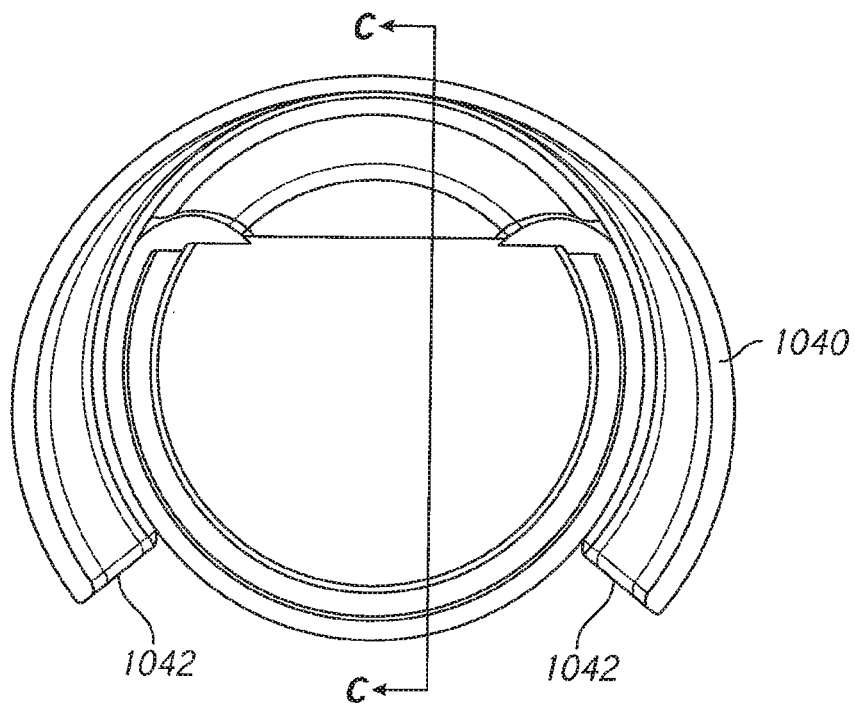
FIG. 10B is cross-sectional top view of the valve of FIG. 10A.
Figure 10C:
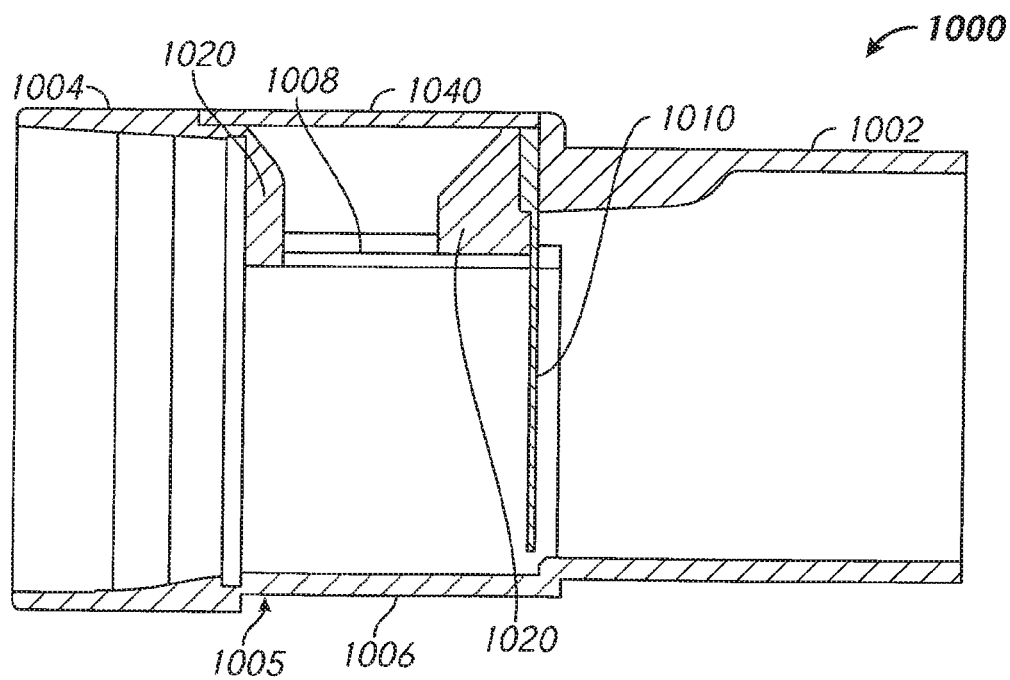
FIG. 10C is a sectioned view of the valve of FIG. 10A taken along the line C-C in FIG. 10B.
Figure 10D:
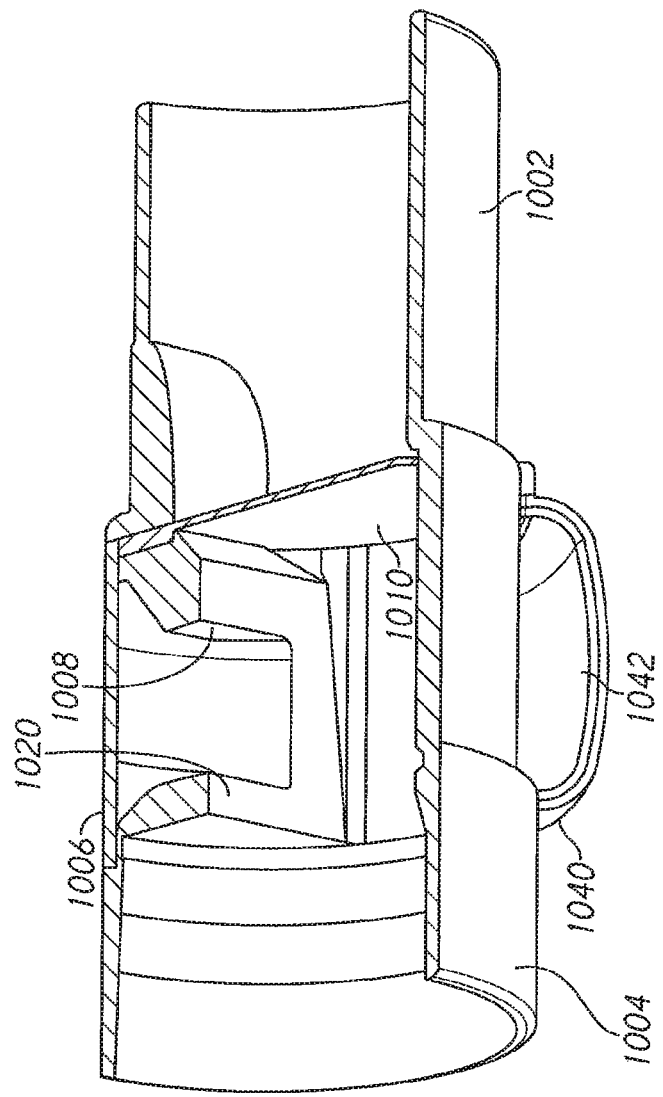
FIG. 10D is a perspective view of the sectioned valve of FIG. 10C.

With reference now to FIG. 10A to FIG. 10D, a further flow diversion device 1000 is illustrated. As illustrated in FIG. 10A, the flow diversion device comprises an inlet portion 1002 and an outlet portion 1004. The inlet and outlet portions 1002, 1004 can have any suitable configuration and can be configured similarly to the inlet and outlet portions 902, 904 described above.

A flow passage or bore is defined a body 1005 of the flow diversion device 1000 from the inlet portion 1002 to the outlet portion 1004. A central portion 1006 of the body 1005 comprises a flow port 1008 that extends through the wall of the body 1005 of the flow diversion device 1000. The flow path through the flow diversion device 1000 can communicate with the surroundings through the port 1008.

A flexible valve member 1010 extends into the flow path at a location between the inlet to the inlet portion 1002 and the port 1008. An inner surface 1020 surrounding the port 1008 may act as a land or valve seat for when the flow diversion device 1000 is in the closed condition. In the closed condition, the valve member 1010 generally cuts off flow from inside the user interface 204 to the ambient surroundings through the port 1008.

The port 1008, similar to the port 908, preferably is large enough to enable most of an exhalation flow to pass through the port 1008 into the ambient atmosphere. If the port 1008 is too small in area, the exhalation flow will take a path of least resistance around the port 1008 and go through the flow diversion device 1000 and the conduit instead. Because in such an instance, at least a large portion of the exhalation flow remains within the flow diversion device and the conduit, at least a portion of the exhalation flow likely would be rebreathed in the next inhalation. This is undesired.

On the other hand, if the port 1008 is too large in area, all of the exhaled gases will flow through the port 1008 to the ambient and there will be very little of the exhaled gases impinging upon the valve member 1010. The valve member 1010, when not positioned over the port 1008, creates a resistance to gases flow from the flow generator 210, 212. If the port 1008 is too large, the flow that urges the port 1008 into a resistance-generating position will be too small and will not be indicative of patient breathing.

Figure 11:
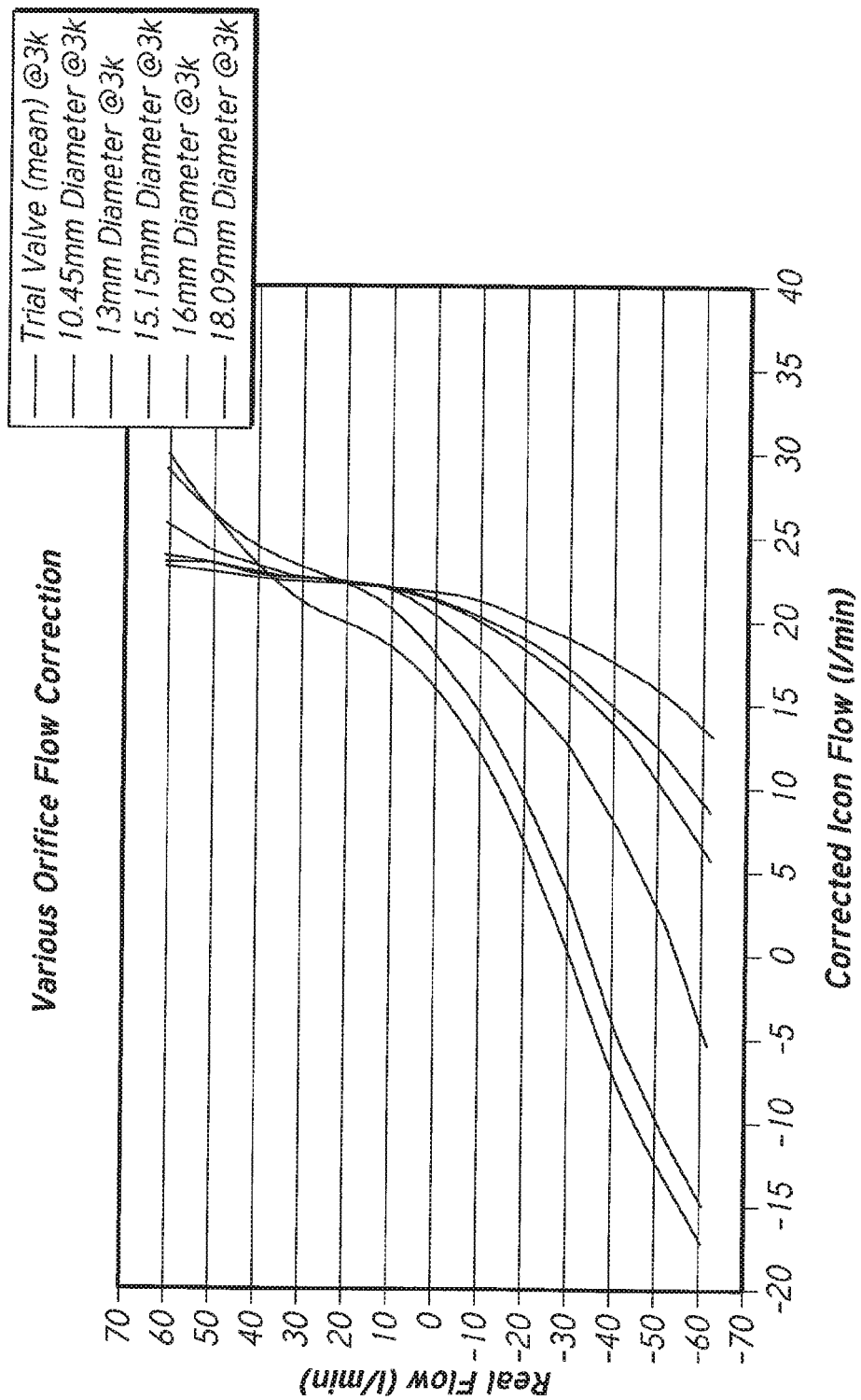
FIG. 11 is a graphical representation of an impact of valve orifice sizes on flow rates.

Under normal breathing conditions (e.g., a flow of about 25 L/min) and with a blower operating in a flow control mode with a flow rate of about 15-20 L/min, it has been found that the port 1008 preferably has a cross section of about 90 mm2. In some applications, the port 1008 can have a cross section of between about 40 mm2 and about 250 mm2. In some applications, the port 1008 can have a cross section of between about 85 mm2 and about 180 mm2. FIG. 11 represents various sizes of ports 1008 and the impact on flow rates.

With respect to the valve member 1010, for the valve member 1010 to function as a non-rebreathing valve, the size of the valve member 1010 preferably is large enough to substantially occlude the flow path from the outlet portion 1004 to the inlet portion 1002. If the valve member 1010 is too small, the exhalation flow will take the least resistance path and go down the conduit. If the exhalation flow goes down the conduit, then the exhalation flow likely will be rebreathed on the next inhalation.

With the valve member 1010 being generally perpendicular to the gases flow, the resistance to flow from the flow generator can be maximized. Thus, during exhalation, a larger valve member 1010 can increase the resistance to flow from the flow generator. It currently is believed that information regarding a user's breathing can be amplified and the controller 224 thereby can receive data having a better resolution with a larger valve member when compared to a smaller valve member or with a valve member without a valve seat when compared to a valve member with a valve seat. The valve member 1010, however, desirably is small enough to allow substantially free movement of the valve member 1010. In the illustrated configuration, the valve member 1010 does not have a seat in the flow path from the flow generator to the interface.

In the illustrated configuration, the port 1008 is covered with a shroud 1040. The shroud 1040 extends around at least a portion of the outer surface of the body 1005. In some configurations, the body 1005 is generally cylindrical and the shroud 1040 extends around a portion of the circumference of the body 1005. In the illustrated configuration, the shroud 1040 extends around an outer surface of the central portion 1006 of the body 1005. The shroud 1040 has a first end and a second end 1041 that define openings 1042. Gases passing out of the port 1008 pass through a passage defined between the illustrated shroud 1040 and the central portion 1006 of the body 1005 and are exhausted to the ambient atmosphere through the openings 1042. Similarly, air can pass through that same passage, into the port 1008 and into the flow diversion device 900.

With reference now to FIGS. 12A to 12D, a further flow diversion device 1200 is illustrated that can be used in an implementation of a system that is arranged and configured in accordance with features, aspects, and advantages described herein. The flow diversion device 1200 can be arranged as a connector for simplicity of assembly with other pre-existing components. In some embodiments, the flow diversion device 1200 comprises an adaptable venting arrangement configured to change a size of a venting area in response to changes in pressure.

Figure 12A:
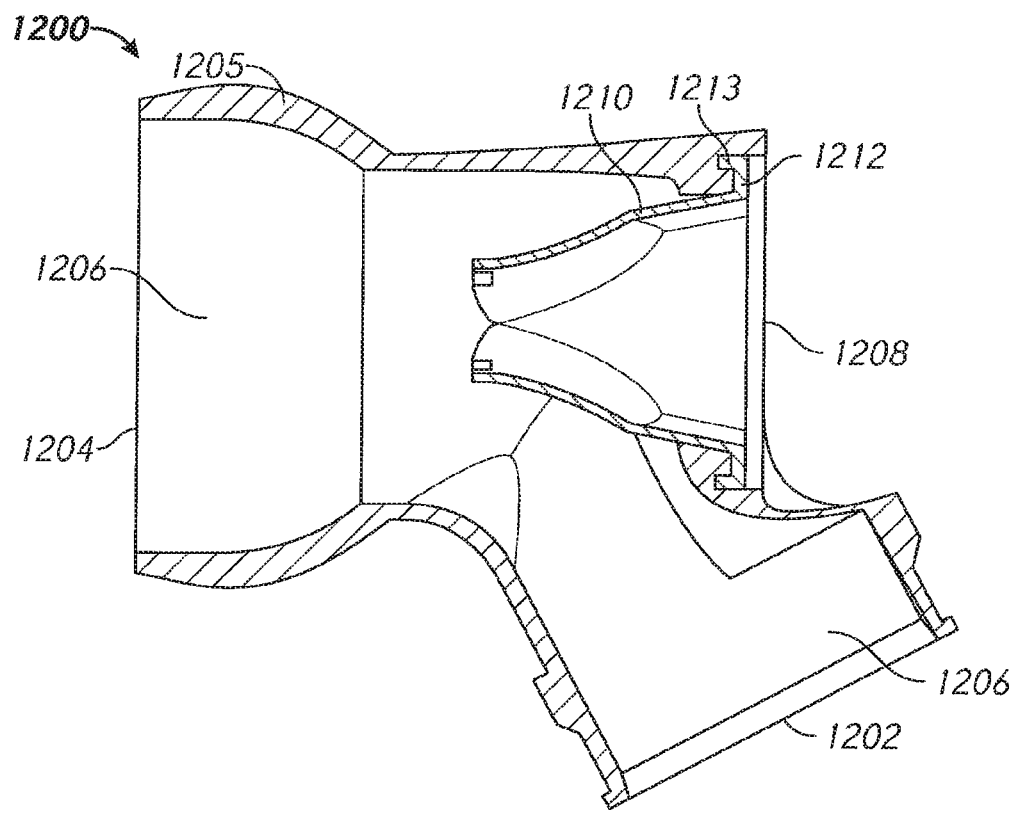
FIG. 12A is a cross-section view of an example venting arrangement comprising a cuspid valve, the venting arrangement being configured to be pressure-dependent.

As illustrated in FIG. 12A, the flow diversion device 1200 comprises an inlet portion 1202 and an outlet portion 1204. The inlet and outlet portions 1202, 1204 can have any suitable configuration and can be configured similarly to the inlet and outlet portions 902, 904, 1002, 1004 described herein with reference to FIGS. 9 and 10, respectively. For example and without limitation, the inlet portion 1202 can comprise a connector portion that includes an external tapered connection surface or an external feature configured to mate with a corresponding feature in a connecting element, such as a gases conduit. The outlet portion 1204 can comprise a connector portion that includes an internal tapered connection surface that is configured to mate with a corresponding connecting element, such as a swivel connector. Other connector configurations are possible.

A flow passage or bore 1206 is provided through a body 1205 of the flow diversion device 1200 from the inlet portion 1202 to the outlet portion 1204. Between the inlet portion 1202 and the outlet portion 1204, the flow diversion device 1200 comprises a flow port 1208 extending through a wall of the flow diversion device 1200. The flow path through the flow passage 1206 of the flow diversion device 1200 can communicate with ambient surroundings through the flow port 1208.

The flow diversion device 1200 includes a pressure-dependent valve 1210 positioned in the flow port 1208, such that gases passing between the flow passage 1206 and ambient pass through the pressure-dependent valve 1210. The pressure-dependent valve 1210 is adapted to assume an open configuration, allowing passage of gases to ambient from the flow passage 1206 through the flow port 1208, and a closed configuration, substantially occluding the flow port 1208. The pressure-dependent valve 1210 is adapted to assume the open configuration in response to a pressure within a first pressure range and to assume the closed configuration in response to a pressure within a second pressure range. In some embodiments, the minimum value in the second pressure range is greater than the maximum value in the first pressure range. In some embodiments, the first pressure range overlaps with the second pressure range.

Figure 12B:
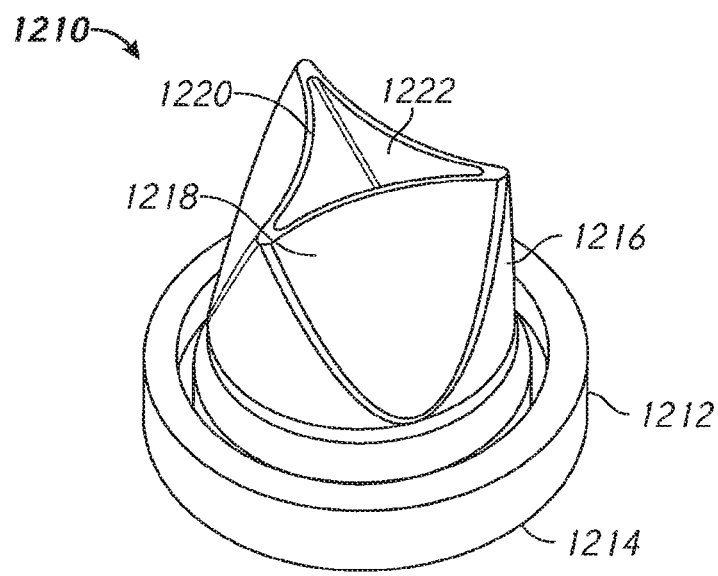
FIG. 12B is a perspective view of the valve in the example venting arrangement illustrated in FIG. 12A.

As illustrated in FIG. 12B, the pressure-dependent valve 1210 includes a base 1212. The perimeter of the base 1212 can be circular, elliptical, square, rectangular, or have any regular or irregular shape. The base 1212 can include an opening 1214 wherein gases flowing through the pressure-dependent valve 1210 pass through the opening 1214. The base 1212 and the opening 1214 can be configured to couple with the flow port 1208 and the body 1205 of the flow diversion device 1200. For example, the base 1212 can include a feature or raised element 1213 along the base 1212 that mates with a corresponding feature on the body 1205 of the flow diversion device 1200, as illustrated in FIG. 12A. When installed, the interaction between the raised element 1213 of the base 1212 and the body 1205 can create a seal around the perimeter of the base 1212. The base 1212, the body 1205, and the flow port 1208 can thus be configured to allow gases to flow between the flow passage 1206 and ambient through the opening 1214 of the valve 1210 and to otherwise prevent gases from entering the flow passage 1206 from ambient.

Returning to FIG. 12B, the pressure-dependent valve 1210 includes a resilient valve member coupled to the base 1212, the resilient valve member comprising a plurality of cuspids 1216 wherein a plurality of cuspid wings 1218 attach adjacent cuspids 1216. Each of the plurality of cuspids 1216 is configured to have a proximal end that couples to the base 1212 and a distal end extending from the base 1212, each cuspid 1216 generally extending in the same direction. The pressure-dependent valve 1210 includes a plurality of cuspid wings 1218 that attach adjacent cuspids, such that a left edge of a cuspid wing attaches to a right end of a first cuspid, and a right edge of the cuspid wing attaches to a left end of a second cuspid, the second cuspid adjacent to the first cuspid. In this manner, the combination of cuspids 1216 and cuspid wings 1218 form a sealed valve flow passage. As illustrated in FIG. 12B, the pressure-dependent valve 1210 includes three cuspids 1216 and three cuspid wings 1218, but any suitable number of cuspids and cuspid wings can be used. For example, and without limitation, two, four, five, six, seven, eight, or more than eight cuspid and cuspid wings can be used. As illustrated, there is a curved interface between a cuspid 1216 and a cuspid wing 1218, but the interface can be, for example and without limitation, curved, straight, jagged, wavy, or any other suitable configuration.

Figure 12C:
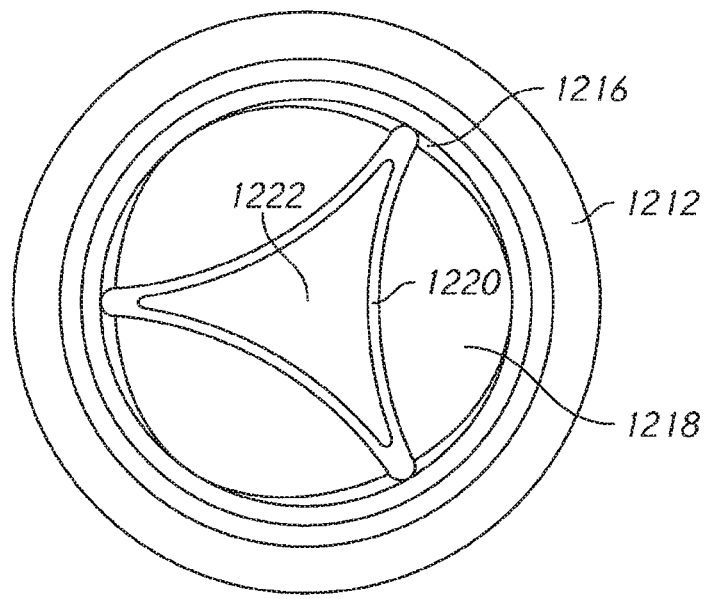
FIG. 12C is a top view of the valve in the example venting arrangement illustrated in FIG. 12A, wherein the valve is substantially open.
Figure 12D:
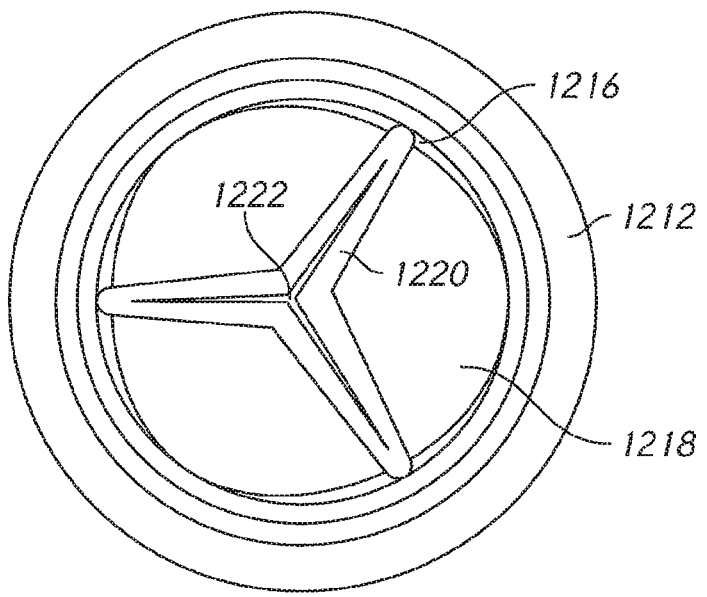
FIG. 12D is a top view of the valve in the example venting arrangement illustrated in FIG. 12A, wherein the valve is substantially closed.

The pressure-dependent valve 1210 includes a cuspid lip 1220 at a distal end of each of the cuspid wings 1218, the cuspid lips 1220 forming a valve aperture 1222. Accordingly, in the first configuration illustrated in FIG. 12C, the pressure-dependent valve 1210 is configured to allow gases to flow through the valve aperture 1222 and the opening. In the second configuration illustrated in FIG. 12D, the pressure-dependent valve 1210 is configured to substantially close the valve aperture 1222 by moving the cuspid lips 1220 to be near one another or to be in contact with one another, thereby substantially preventing gases from flowing through the sealed valve flow passage. In some embodiments, the resilient valve member coupled to the base 1212 comprises a flexible arrangement forming a lip 1220 defining a valve aperture 1222, but does not comprise multiple sides as shown in FIGS. 12B-D. For example, the flexible arrangement can have a substantially circular, elliptical, or other rounded cross-section. Configured in this way, the flexible arrangement can be configured as a cylinder or tapered cylinder with the lip 1220 configured to open and close in response to changes in pressure.

The pressure-dependent valve 1210 is adapted to reduce the size of the valve aperture 1222 in response to an increase in pressure through the flow passage 1206 and to increase the size of the valve aperture 1222 in response to a decrease in pressure. In some embodiments, when the pressure through the flow passage 1206 is below a low pressure threshold, the valve aperture 1222 is substantially open, approaching a maximum aperture size. For example, the maximum aperture size can be at least about 90 mm2, at least about 60 mm2, at least about 40 mm2, at least about 30 mm2, or at least about 20 mm2. In some embodiments, when the pressure through the flow passage 1206 is above a high pressure threshold, the valve aperture 1222 is substantially closed. For example, when the pressure exceeds the high pressure threshold, the cuspid lips 1220 can come into contact in response to the elevated pressure, as illustrated in FIG. 12D. In some embodiments, the pressure-dependent valve 1210 is adapted to change the size of the valve aperture 1222 as a function of pressure. For example, the size of the valve aperture 1222 can have a maximum aperture under atmospheric pressures and the size can smoothly decrease with a steady increase in pressure until the pressure exceeds the high pressure threshold wherein the size of the valve aperture 1222 is at a minimum. As another example, the size of the valve aperture 1222 can be near a maximum size when exposed to a pressure within a low pressure range and the size of the valve aperture 1222 can be near a minimum size when exposed to a pressure within a high pressure range.

In some embodiments, the pressure-dependent valve 1210 can be resistant to changes in flow when pressure is substantially constant. For example, the pressure-dependent valve 1210 can be adapted to remain substantially open when a pressure in the flow passage 1206 falls within the first range of pressures even where the flow varies. The pressure-dependent valve 1210 can be adapted to remain substantially closed when a pressure in the flow passage 1206 falls within the second range of pressures even where the flow varies. The pressure-dependent valve 1210 can be adapted to remain in the first configuration when a pressure in the flow passage 1206 is within the first range of pressures and the second configuration when the pressure is within the second range of pressures, and to not change configurations when flow through the flow passage 1206 varies. The pressure-dependent valve 1210 can be configured to transition between the first configuration and the second configuration in response to a change in pressure between the first range of pressures and the second range of pressures and not to a change in flow. In some embodiments, the pressure-dependent valve 1210 is not activated by flow but is substantially pressure-dependent.

The plurality of cuspids 1216 and the plurality of cuspid wings 1218 can be made of a suitable, elastomeric material. When subjected to a differential in pressure, e.g. when a pressure on the exterior faces of the cuspids 1216 and the cuspid wings 1218 exceeds a pressure on the interior faces, the cuspids 1216 and cuspid wings 1218 can deform, bringing the cuspid lips 1220 toward one another. When the pressure differential increases, the cuspid lips 1220 can become closer to one another, and when the pressure differential decreases, the cuspid lips 1220 can become farther apart. Where there is no pressure differential, the valve aperture 1222 can have a default or equilibrium size, corresponding to a substantially open configuration. Where pressure differential exceeds a high pressure threshold, the valve aperture 1222 can have a near-minimum size, corresponding to a substantially closed configuration.

Returning to FIG. 12A, the flow diversion device 1200 comprises an elbow connector that can be coupled to a user interface. The flow diversion device 1200 can be of any suitable shape or configuration designed to direct a flow of gases between the user interface, the flow generator, and ambient. The pressure-dependent valve 1210 can be configured to be a part of the flow diversion device 1200 and to regulate a flow of gases between the flow passage 1206 and ambient by changing a size of the valve aperture 1222, as described herein.

Figure 13A:
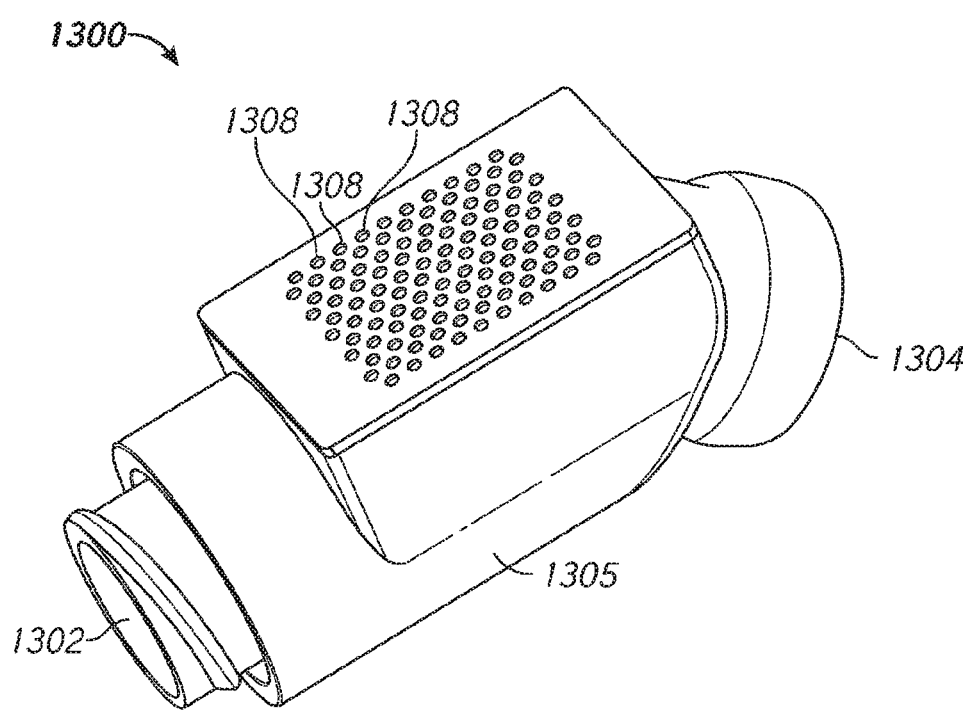
FIG. 13A is a perspective view of an example venting arrangement configured to provide constant flow.
Figure 13B:
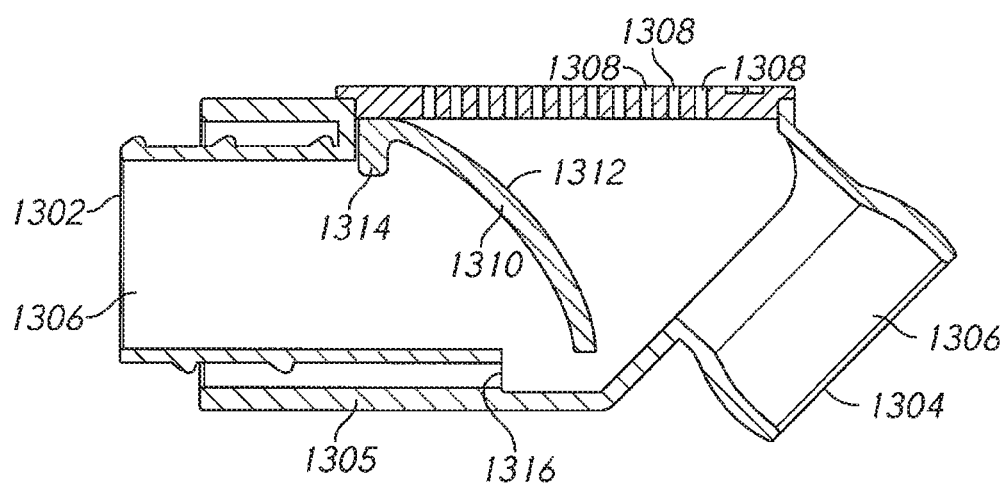
FIG. 13B is a cross-sectional side elevation of the constant-flow venting arrangement illustrated in FIG. 13A, showing a curved valve member.
Figure 13C:
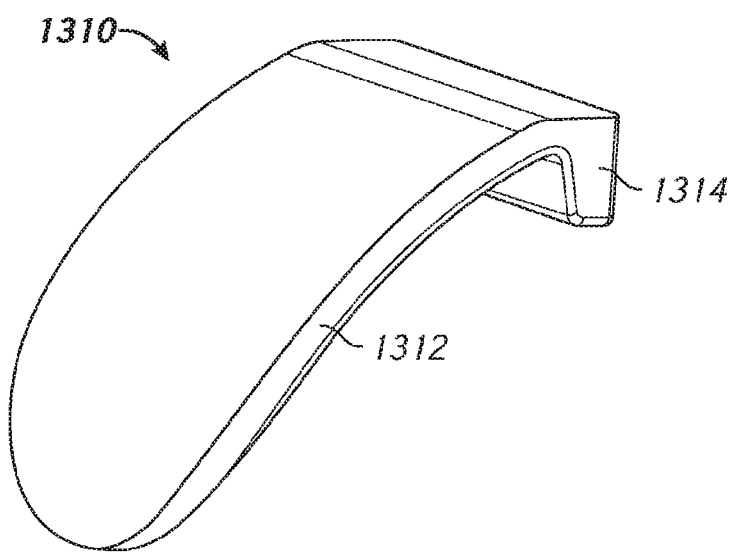
FIG. 13C is a perspective view of the curved valve member of the example constant-flow venting arrangement illustrated in FIG. 13A.

With reference now to FIGS. 13A to 13C, a further flow diversion device 1300 is illustrated that can be used in an implementation of a system that is arranged and configured in accordance with features, aspects, and advantages described herein. The flow diversion device 1300 can be arranged as a connector for simplicity of assembly with other pre-existing components. In some embodiments, the flow diversion device 1300 comprises an adaptable venting arrangement configured to change a size of a venting area and to provide a substantially constant flow through the flow diversion device 1300 when subjected to pressure within a pressure range. In some embodiments, the flow diversion device 1300 can regulate flow through a pressure range, such that a substantially constant flow rate is provided at the vent with changing pressure over the pressure range. The pressure range can be, for example, between 0 cmH2O and about 30 cmH2O, or between about 0 cmH2O and about 20 cmH2O. This can reduce noise, draft, and/or water usage compared to other flow diversion devices.

As illustrated in FIG. 13A, the flow diversion device 1300 comprises an inlet portion 1302 and an outlet portion 1304. The inlet and outlet portions 1302, 1304 can have any suitable configuration and can be configured similarly to the inlet and outlet portions 902, 904, 1002, 1004, 1202, 1204 described herein with reference to FIGS. 9, 10, and 12, respectively, including elements and features configured to connect with other elements of the system, such as a gases conduit and/or the user interface. The flow diversion device 1300 includes a body 1306 and one or more flow ports 1308. As illustrated, the flow ports 1308 comprise a plurality of passageways between ambient and an interior of the body 1305, but other configurations are possible as well. For example, the flow port 1308 can be a single passageway or opening in the body 1305, or a plurality of openings arranged in rows and columns, in staggered columns, in a circular pattern, in a random pattern, or in any other suitable or desirable configuration.

With reference to FIG. 13B, the flow diversion device 1300 can include a flow passage or bore 1306 provided through the body 1305 of the flow diversion device 1300 from the inlet portion 1302 to the outlet portion 1304. Between the inlet portion 1302 and the outlet portion 1304, the flow diversion device 1200 includes the flow port 1308 extending through a wall of the flow diversion device 1300. The flow path through the flow passage 1306 of the flow diversion device 1300 can communicate with ambient surroundings through the flow port 1308.

The flow diversion device 1300 includes a constant-flow valve 1310 configured to provide a constant flow with increasing pressure. The constant-flow valve 1310 is positioned within the flow diversion device 1300 to regulate a flow of gases through the flow passage 1306. In some embodiments, the constant-flow valve 1310 can be adapted to provide a constant flow rate through the flow passage 1306 when a pressure through the flow passage 1306 exceeds a constant-flow pressure threshold. The constant-flow valve 1310 can be adapted to be movable between a first position and a second position wherein, in the first position, the flow passage 1306 is substantially occluded leaving the flow port 1308 substantially open for flow from the user interface to ambient, and, in the second position, the flow port 1308 is substantially occluded leaving the flow passage 1306 substantially open for flow from the inlet portion 1302 to the outlet portion 1302.

In some embodiments, the constant-flow valve 1310 includes a curved valve member 1312 coupled to the at least one wall adjacent to the flow port 1308. The curved valve member 1312 can be configured to substantially occlude the flow passage 1306 in the first position and to substantially occlude the flow port 1308 in the second position. The curved valve member 1312 can be configured to move between the first position and the second position. The curved valve member 1312 can be coupled to the body 1305 at the valve member anchor 1314. The anchor 1314 can be secured to the body 1305 using any suitable means including, without limitation, fasteners, adhesives, friction, and the like.

In some embodiments, as illustrated in FIG. 13C, the curved valve member 1312 has a substantially parabolic cross-section. The curved valve member 1312 can have other cross-sections, including, without limitation, elliptical arc, circular arc, hyperbolic, a portion of a polygon, a series of straight edges approximating any of the above, and the like. The design of the curved valve member 1312, as implemented in the flow diversion device 1300, can be configured to become increasingly difficult to close with increasing pressure, thereby providing a substantially constant flow with increasing pressure.

Returning to FIG. 13B, the constant-flow valve 1310 can be configured to provide a substantially constant flow based at least in part to a response of the curved valve member 1312 to increases in pressure. As pressure in the flow passage 1306 increases, the curved valve member 1312 becomes increasingly difficult to move. One result of this property is that as pressure increases, the constant-flow valve 1310 provides for a substantially constant flow. In some embodiments, the constant-flow valve 1310 maintains the curved valve member in the first position when a pressure through the flow passage is within a first pressure range and the second position when the pressure through the flow passage is within a second pressure range. In some embodiments, the constant-flow valve 1310 maintains the curved valve member in the first position when a flow rate through the flow passage is within a first flow range and the second position when the flow rate through the flow passage is within a second flow range.

The flow diversion device 1300 can include a land or valve seat 1316 configured to provide a stop for the curved valve member 1312. In some embodiments, when the constant-flow valve 1310 is in the first position, the curved valve member 1312 abuts the land or valve seat 1316, thereby substantially opening the flow port 1308 to allow gas to flow from the user interface to ambient. In some embodiments, when the constant-flow valve 1310 is in the second position, the curved valve member 1312 substantially occludes the flow port 1308, thereby allowing gas to flow from the inlet portion 1302 to the outlet portion 1304.

The curved valve member 1312 can be made of any suitable material. In some embodiments, the curved valve member 1312 is made of a flexible, polymeric or elastomeric material. The curved valve member 1312 can bend or flex in response to changes in pressure. In some embodiments, the curved valve member 1312 can be made of a substantially rigid material and can be rotatably coupled to the body 1305 at the anchor 1314, which acts as a pivot. The constant-flow valve 1310 can mounted to the flow diversion device 1300 in such a way as to provide resistance to the rotation of the curved valve member, for example and without limitation, through the use of springs, friction, or some other method. Based at least in part to this resistance, when the constant-flow valve 1310 is exposed to a pressure differential that is approximately zero, the curved valve member 1312 assumes a default or equilibrium position, and when exposed to a pressure differential that is greater than a high pressure threshold, the curved valve member 1312 assumes a position that substantially occludes the flow port 1308.

The flow diversion device 1300 comprises an elbow connector that can be coupled to the user interface. The flow diversion device 1300 can be of any suitable shape or configuration designed to direct a flow of gases between the user interface, the flow generator, and ambient. The constant-flow valve 1310 can be configured to be a part of the flow diversion device 1300 and to regulate a flow of gases between the flow passage 1306 and ambient by changing a position of the curved valve member 1312, as described herein.

Other valve constructions also are possible without departing from the general scope of the present invention. In some configurations, valves can be used that are similar to those described in U.S. Provisional Patent Application No. 61/504,295, filed Jul. 4, 2011, which is hereby incorporated by reference in its entirety. In addition, the Quattro anti-asphyxia valve by ResMed has suitable characteristics, although not as good as the valve described with reference to FIGS. 9A to 9C. Other valve constructions may be devised that meet the desired functional criteria for opening and closing with respect to the prevailing conditions in a stable manner. These preferred functional aspects will be apparent from the discussion below with reference to FIGS. 5, 6, 7 and 8. Furthermore, the valve constructions described and incorporated by reference herein can be used together in cooperation. For example, the pressure-dependent valve illustrated in FIGS. 12A to 12D can be used in conjunction with the constant-flow valve illustrated in FIGS. 13A to 13C. The valve constructions can be used in the system in any suitable combination with one another and in any suitable configuration to provide desired pressure and/or flow.

Example Tests of Values and Systems

Behaviour of systems that have been arranged and configured in accordance with certain features, aspects and advantages of the present invention (e.g., utilising the valve described with reference to FIGS. 9A-9C and also an alternative commercially available valve) are described below. The tests demonstrated comparative performance of the valves and comparative performance of different control methods when used with the valves. Tests were conducted using a test setup as illustrated in FIG. 4.

Figure 4:
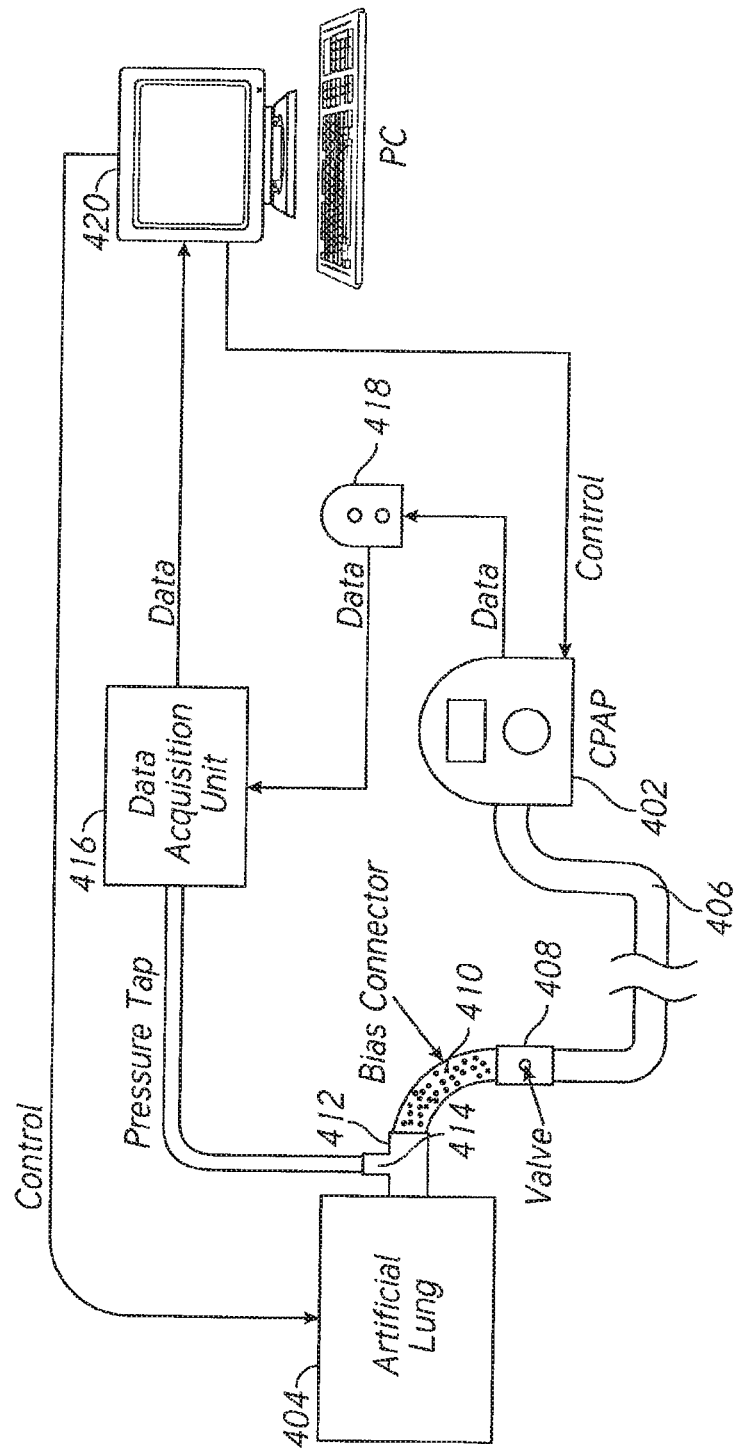
FIG. 4 is a block diagram of an experimental setup used to evaluate machines arranged and configured in accordance with certain features, aspects and advantages of the present invention.

The test setup illustrated in FIG. 4 comprises a CPAP flow generator 402 that is connected to deliver flow to an artificial lung 404. The CPAP flow generator 402 used in the experiments described herein was a Fisher & Paykel ICON Auto available from Fisher & Paykel Healthcare Limited, Auckland, New Zealand. The CPAP flow generator 402 featured modified software that was modified to remove lower limits. The artificial lung was an ASL5000 available from Ingmar Medical Ltd of Pittsburgh, USA.

The CPAP flow generator 402 was connected to the artificial lung 404 via a delivery conduit 406. The delivery conduit 406 was the 1.8 m supply hose supplied with the ICON Auto.

Between the user end of the delivery conduit 406 and the inlet port of the artificial lung were, in series, the valve 408 being tested, a bias flow connector 410, and a connector 412 including a port 414 for measuring characteristics of the gases stream. The bias flow connector 410 was an elbow from an HC407 nasal mask available from Fisher & Paykel Healthcare Limited. In the illustrated setup, the port 414 of the connector 412 was connected to a data acquisition unit 416 for measuring pressure at the entrance to the artificial lung. Additional data collected by the CPAP flow generator 402, including delivered flow, was supplied to a data interface box 418 and on to data acquisition unit 416. The collected data from data acquisition unit 416 was provided to a computer 420 or other suitable processing unit. The computer 420 can be connected to the artificial lung 404 to provide control signals to the artificial lung 404 and to the CPAP flow generator 402 to provide control signals to the CPAP flow generator 402.

Testing of Valve Characteristics under Different Control Modes

In a first set of tests, the apparatus shown in FIG. 4 was used to consider the characteristics of the valve shown in FIGS. 9A-9C and the characteristics of an existing anti-asphyxia valve. These tests show both comparative performance of the valves and comparative performance of the control methods. The existing anti-asphyxia valve is supplied with the ResMed Quattro Full Face User Interface (available from ResMed Pty Limited of Sydney, Australia). The tests demonstrate some of the advantages of the preferred control (i.e., the control as used with either valve) and some of the advantages in this application of the valve of FIGS. 9A-9C over the ResMed anti-asphyxia valve.

For each valve, two series of tests were conducted. For each test in each series, the artificial lung was set up to run through a breath test sequence including: (1) four breaths at 250 ml tidal volume; (2) pause; (3) four breaths at 500 ml tidal volume; (4) pause; (5) four breaths at 750 ml tidal volume; (6) pause; (7) and four breaths at 1000 ml tidal volume. All breaths were sinusoidal at 15 breaths per minute with a 1:1 expiration to inspiration ratio.

In the first test series, the CPAP flow generator 402 was controlled to run at a constant motor speed for the duration of each test. That is, the device ran without pressure or flow feedback control. The device 402 was set to run at a speed at which the delivered average flow was expected to be low and the valve 408 open. The breath sequence was played and the behaviour of the valve 408 was noted. The speed was increased by 1000 rpm and the process was repeated. This cycle was continued, increasing the speed by 1000 rpm each time until the valve 408 reached a stable closed state. Then the process was repeated, reducing the speed by 1000 rpm in each of the test sequences until the valve 408 reached a stable open state. At each of the tests, the behaviour of the valve 408, the average mask pressure and the average flow rate were recorded.

Figure 5A:
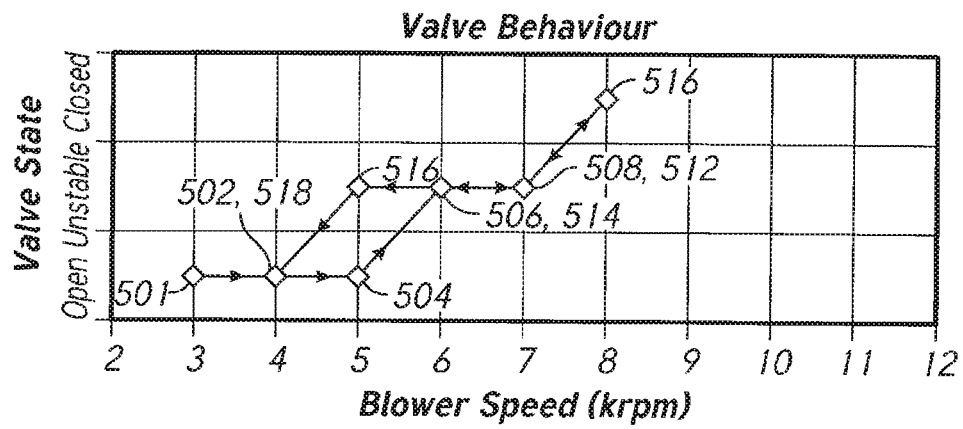
FIGS. 5A to 5F are plots that show opening and closing characteristics of a flow diversion device that is arranged and configured in accordance with certain features, aspects and advantages of the present invention.
Figure 5B:
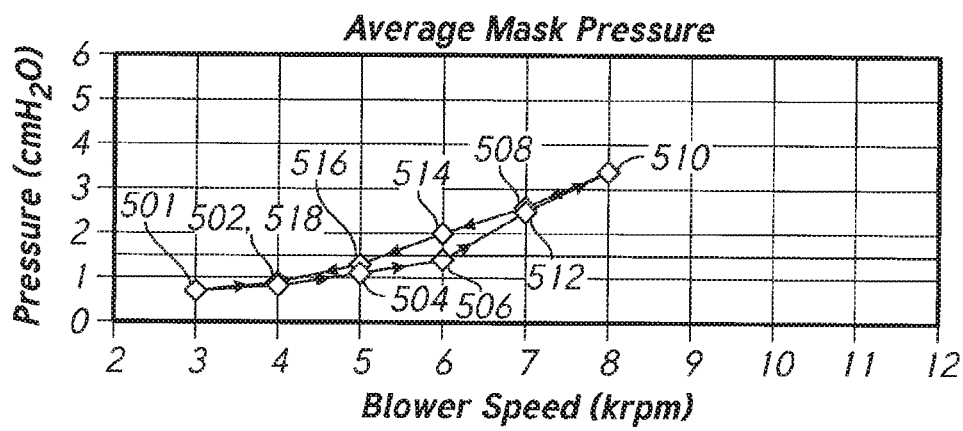
Figure 5C:
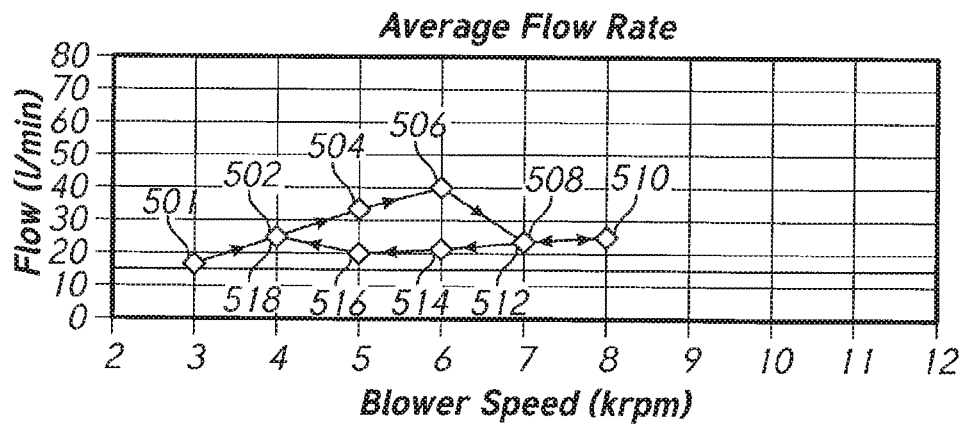
Figure 6A:
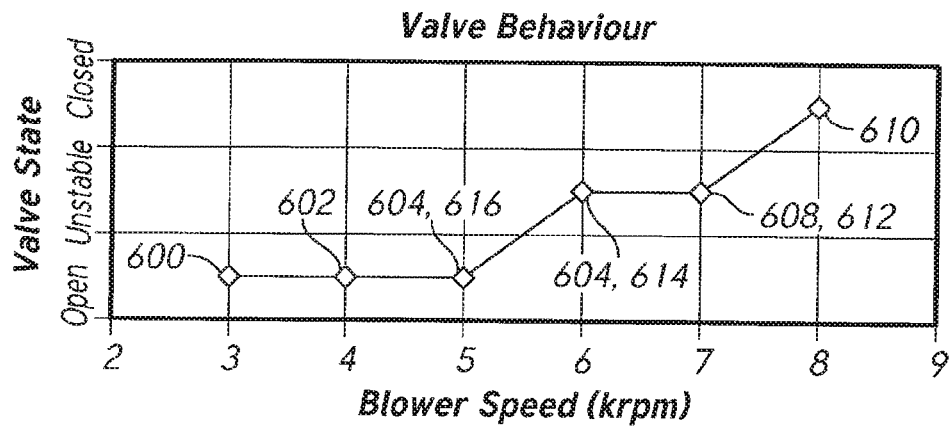
FIGS. 6A to 6F are plots that show opening and closing characteristics of a flow diversion device that is arranged and configured in accordance with certain features, aspects and advantages of the present invention.
Figure 6B:
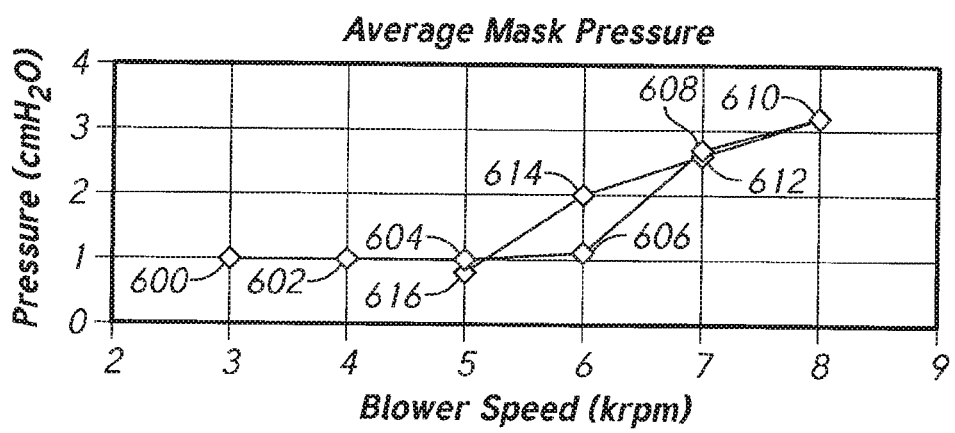
Figure 6C:
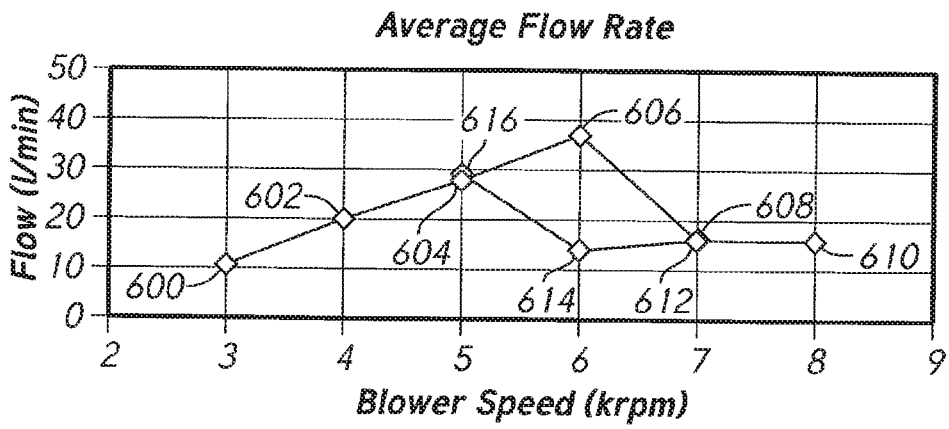

For the valve illustrated in FIGS. 9A-9C, the results of this sequence of tests are illustrated in FIGS. 5A-5C. These figures are discussed in more detail below. For the ResMed Quattro valve, the results of this sequence of tests are illustrated in FIGS. 6A-6C. These results are discussed in more detail below.

Figure 5D:
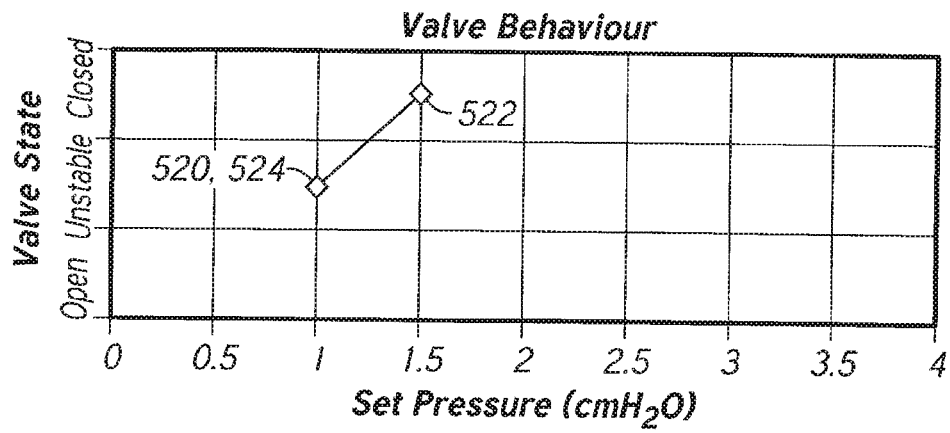
Figure 5E:
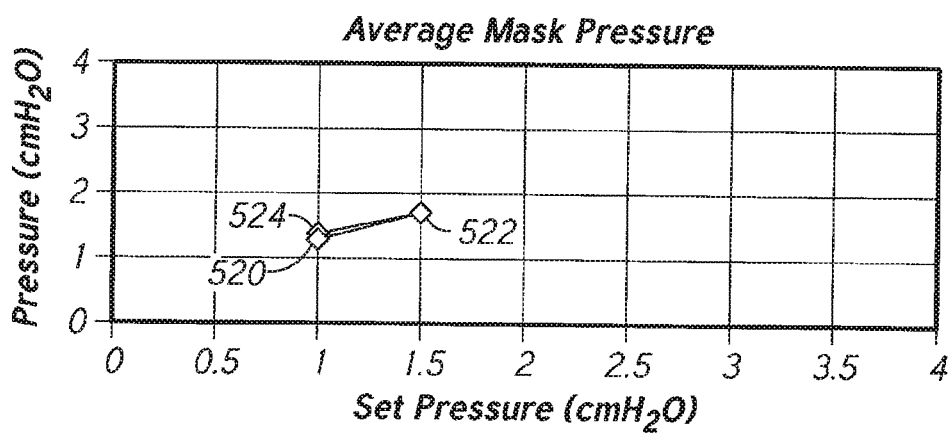
Figure 5F:
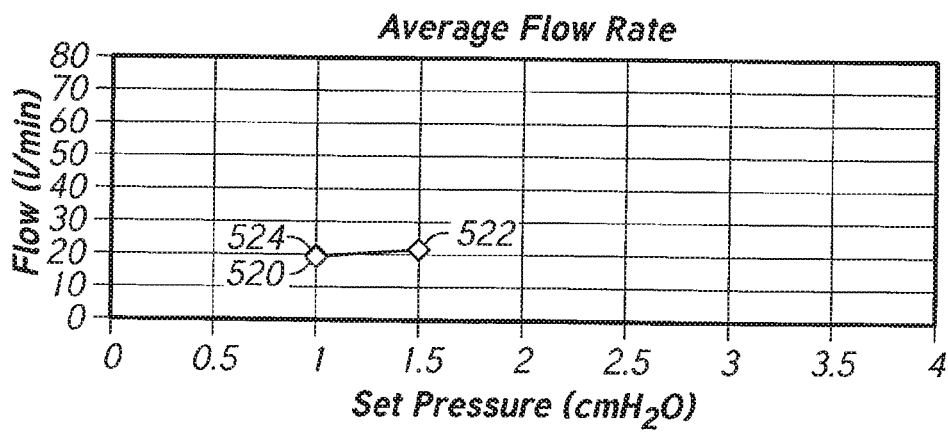
Figure 6D:
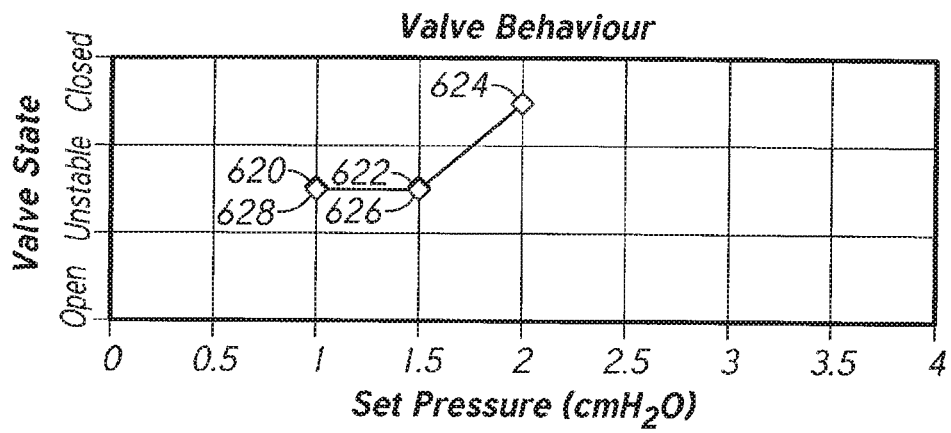
Figure 6E:
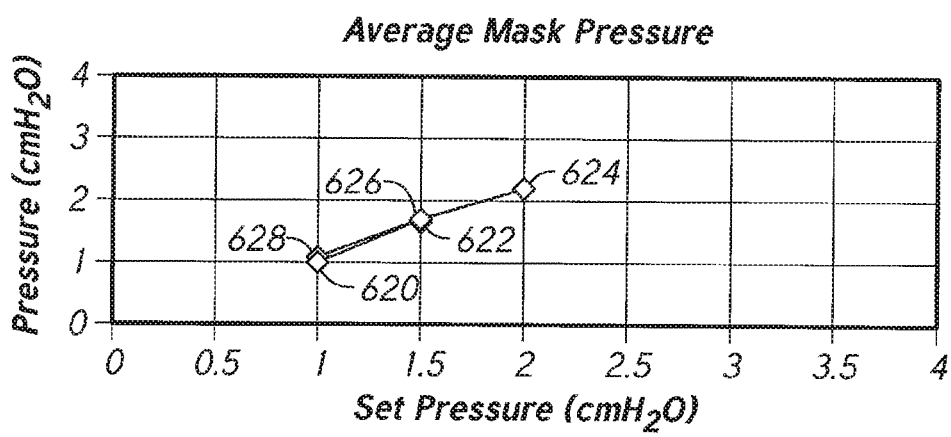
Figure 6F:
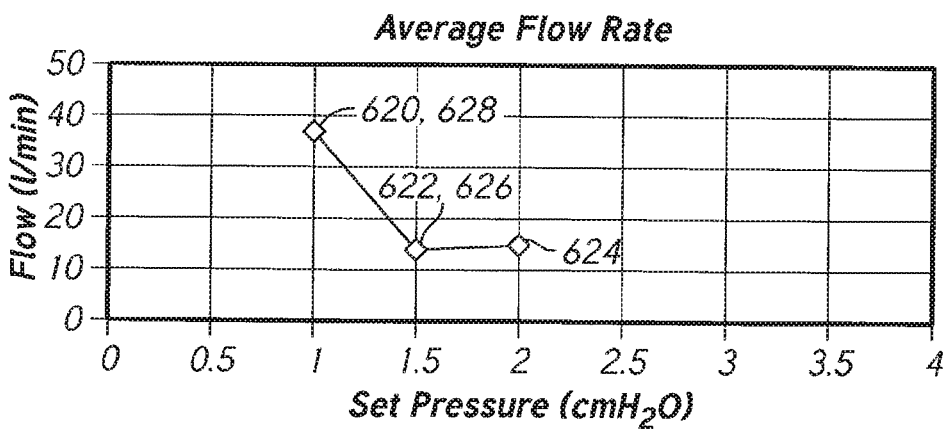

In the second sequence of tests on each valve 408, the CPAP flow generator 402 was run in a pressure feedback mode. The first test in the sequence had the set pressure for the flow generator at 1 cm H2O. Subsequent tests were conducted at increasing pressures, increasing the set pressure by 0.5 cm H2O for each subsequent test. Once the valve 408 reached a stable closed state, the process was repeated in reverse, reducing the set pressure by 0.5 cm H2O for each subsequent test. For each test, the state of the valve 408, the average flow and the average pressure were recorded. The results of this testing for the valve of FIGS. 9A-9C are illustrated in FIGS. 5D-5F. The results of this testing for the ResMed Quattro valve are illustrated in FIGS. 6D-6F.

Test Results for Valve of FIGS. 9A-9C

FIGS. 5A to 5C illustrate the behaviour of the valve 408 shown in FIGS. 9A-9C (i.e., the flow diversion device 900) under constant flow generator speed conditions. This illustrates, for example, the way the valve 408 will behave when the flow generator 402 is controlled with slow feedback based on average flow. The flow generator 402 will not react to the breathing cycle changes in flow or pressure and, over a sequence of breaths, will maintain essentially a constant flow generator speed. The instantaneous flow and pressure will fluctuate as the user breathes. FIG. 5B, which indicates the measured pressure, and FIG. 5C, which indicates the measured flow, both represent the average of the pressure or flow over the breaths of the test. The valve state behaviour in FIG. 5A was by observation. Either the valve 408 remained closed across all of the sequence of breaths, the valve 408 remained open across all of the sequence of breathes, or was instable and moved between the open and closed states in response to the breathing cycle.

The sequence of tests is indicated by the sequence of data points 501, 502, 504, 506, 508, 510, 512, 514, 516, 518. For simplicity, this sequence of data points is indicated by the same reference numerals in each of FIGS. 5A, 5B and 5C.

In FIG. 5A, it can be seen that the behaviour of the illustrated valve, when commencing in the open state, remains stable in the open state at blower speeds of 3000, 4000 and 5000 rpm (data points 501, 502 and 504 in FIG. 5A). At these blower speeds, the pressure delivered to the artificial lung remains below about 1.5 cm H2O (data points 501, 502 and 504 in FIG. 5B). Also within this range, the delivered flow at 3000 rpm was above about 15 litres per minute and the delivered flow at 5000 rpm above about 30 litres per minute. Accordingly, the illustrated valve provides for substantial adjustment of the delivered flow to compensate for large bias flow vents or leaks at the mask without excessively increasing the delivered sub-therapeutic pressure and with the valve staying stable in the open position.

With the illustrated valve of FIGS. 9A-9C and the illustrated flow generator, when reducing the output of the flow generator in response to user awakening, and subsequently entering the constant average flow (i.e., constant rotor speed) mode, the initial flow generator speed should be at or below 4000 rpm so that the valve exhibits the initial stable behaviour (see, for example, the transition between data points 516 and 518 in FIG. 5A).

FIGS. 5D-5F illustrate the results of testing in the pressure feedback mode. As discussed above, the pressure feedback mode is entered to provide therapeutic pressures once the user is asleep. One preferable characteristic of the valve illustrated in FIGS. 9A-9C is to exhibit stable closed behaviour under pressure feedback control at a set pressure that is close to the average mask pressure delivered immediately prior, when the valve behaviour was stable open under constant rotor speed control.

With reference to data points 520 and 524, the valve of FIGS. 9A-9C exhibits unstable behaviour with the pressure feedback control at 1 cm H2O set pressure whether commencing at this set pressure or returning to this set pressure from higher set pressure. However, as indicated by data point 522, at 1.5 cm H2O set pressure, the valve exhibits stable behaviour. At this set pressure, the system delivered an average pressure of about 1.7 cm H2O and delivered an average flow of about 20 litres per minute.

Performance of the Valve of FIGS. 9A-9C in Combination with Preferred Control Modes The delivered average mask pressure with the valve stable and closed (e.g., about 1.7 cm H2O) is less than about 1 cm H2O higher than the delivered average mask pressure under the constant rotor speed control with the valve stable open (data points 501, 502 and 504 in FIG. 5B). The delivered average flow at this setting is within the range of the delivered average flow indicated by data points 501, 502 and 504 in FIG. 5C.

Data point 522 relates to the valve stable and closed (i.e., pressure mode) and generates a mask pressure of about 1.7 cm H2O. Data point 518 relates to the valve stable and open (i.e., speed mode) and generates a mask pressure of about 0.9 cm H2O. The delivered average mask pressure with the valve stable and closed (about 1.7 cm H2O) can be less than about 1 cm H2O higher than the delivered average mask pressure under the constant rotor speed control with the valve stable open (i.e., data points 501, 502 and 504 in FIG. 5B). The delivered average flow at this setting can be within the range of the delivered average flow indicated by data points 501, 502 and 504 in FIG. 5C.

Accordingly, using the illustrated valve and flow generator control combination, the system may move from the sub-therapeutic mode, with a flow generator speed of about 4000 rpm delivering about 0.9 cm H2O, average mask pressure and about 25 litres per minute average flow, to a therapeutic mode, with pressure feedback control, delivering about 1.7 cm H2O average mask pressure and about 20 litres per minute average flow.

When switching from the therapeutic delivery mode to the sub-therapeutic delivery mode (e.g., in response to user awakening), one could expect generally the same transition between system conditions, but in reverse.

Test Results for ResMed Anti-Asphyxia Valve

FIGS. 6A to 6C illustrate the behaviour of the ResMed Quattro valve under constant flow generator speed. This illustrates the way the valve will behave where the flow generator is controlled with slow feedback based on average flow, such as in the preferred sub-therapeutic mode according to certain features, aspects and advantages of the present invention. FIG. 6A illustrates the observed valve state in each of the tests. FIG. 6B indicates the average measured pressure in each of the tests and FIG. 6C illustrates the average measured flow in each of the tests. The sequence of the tests is indicated by the sequence of data points 600, 602, 604, 606, 608, 610, 612, 614, 616. For simplicity, this sequence of data points is indicated by the same reference numerals in each of the FIGS. 6A, 6B and 6C.

From FIG. 6A, it can be seen that the behaviour of the ResMed Quattro valve when commencing in the open state remains stable in the open state at blower speeds of 3000 rpm, 4000 rpm, 5000 rpm (data points, 600, 602 and 604). At these blower speeds, the pressure delivered to the artificial lung is approximately 1 cm H2O (data points 600, 602 and 604 in FIG. 6B). The delivered flow at 4000 rpm is about 20 litres per minute and the delivered flow at 5000 rpm is about 30 litres per minute. However, the delivered flow at 3000 rpm is only about 10 litres per minute, which is lower than desirable. Accordingly, the average flow rate across the range of flow generator speed at which the ResMed Quattro valve is stable is approximately 10 litres per minute to 30 litres per minute compared to approximately 15 litres per minute to 35 litres per minute for the valve of FIGS. 9A-9C.

Referring to FIGS. 6D to 6F, these figures illustrate the results of testing in the pressure feedback mode. With reference to data points 620, 622, 624, 626, the ResMed Quattro valve exhibits unstable behaviour with the pressure feedback control at a 1 cm H2O set pressure whether commencing at this set pressure or returning to this set pressure from a higher set pressure. The valve remains unstable at 1.5 cm H2O set pressure (data points 622 and 626 in FIG. 6A). The valve exhibits stable behaviour once the set pressure reaches 2 cm H2O (data point 624 in FIG. 6A). With a set pressure of 2 cm H2O, the delivered average pressure was about 2.2 cm H2O (data point 624 in FIG. 6E). At 2 cm H2O, the delivered average flow rate was about 15 litres per minute (data point 624 in FIG. 6F).

Performance of the ResMed Valve in Combination with the Preferred Control Mode

The delivered average mask pressure with the ResMed Quattro valve at the lowest set pressure for stable closed valve behaviour is approximately 1.2 cm H2O above the delivered average mask pressure under constant speed control with the valve open. The delivered average flow rate is at the lower end of the average flow rate range using motor speed control.

Using this valve and flow generator combination, one could expect to transition from the sub-therapeutic mode (i.e., with a flow generator speed of about 4000 rpm), delivering about 1 cm H2O average mask pressure and about 20 litres per minute average flow, to a therapeutic mode with pressure feedback control, delivering about 2.2 cm H2O mask pressure and about 15 litres per minute average flow. When switching from a therapeutic delivery to the sub-therapeutic delivery, one could expect the same transition between system conditions but in reverse.

Comparison of FIGS. 9A-9C Valve Performance with ResMed Valve Performance Both the valve of FIGS. 9A-9C and the ResMed valve provide adequate performance in conjunction with the preferred control—switching from an open loop control to a pressure feedback control—at the transition from sub-therapeutic to therapeutic modes. In each case, the delivered flows at the transition are sufficient and the pressure step is reduced compared with the same transition under pressure feedback only control. However, the valve of FIGS. 9A-9C provided a lower step in mask pressure (e.g., about 0.8 cm H2O) when compared with the ResMed valve (e.g., about 1.2 cm H2O) and provided a greater flow at both the sub-therapeutic and the therapeutic pressures around the transition.

Comparison Using the Example Control Method in a Sequence of Simulated Breaths

The effect of particular valve behaviour can be seen in the results of the additional test sequence executed on each of the ResMed Quattro valve and the valve of FIGS. 9A-9C. According to the second test sequence, the artificial lung was set up to simulate continuous breathing at 1000 ml tidal volume, with all breaths sinusoidal at 15 breaths per minute with a one-to-one expiration to inspiration ratio. The flow generator was controlled to commence with a constant speed of 3000 rpm. After a period of time, the flow generator was switched to a pressure feedback mode with a set pressure of 1.5 cm H2O. Throughout the test, the valve behaviour was observed and the delivered flow (i.e., the flow leaving the flow generator) and the pressure at the artificial lung were recorded.

Figure 7A:
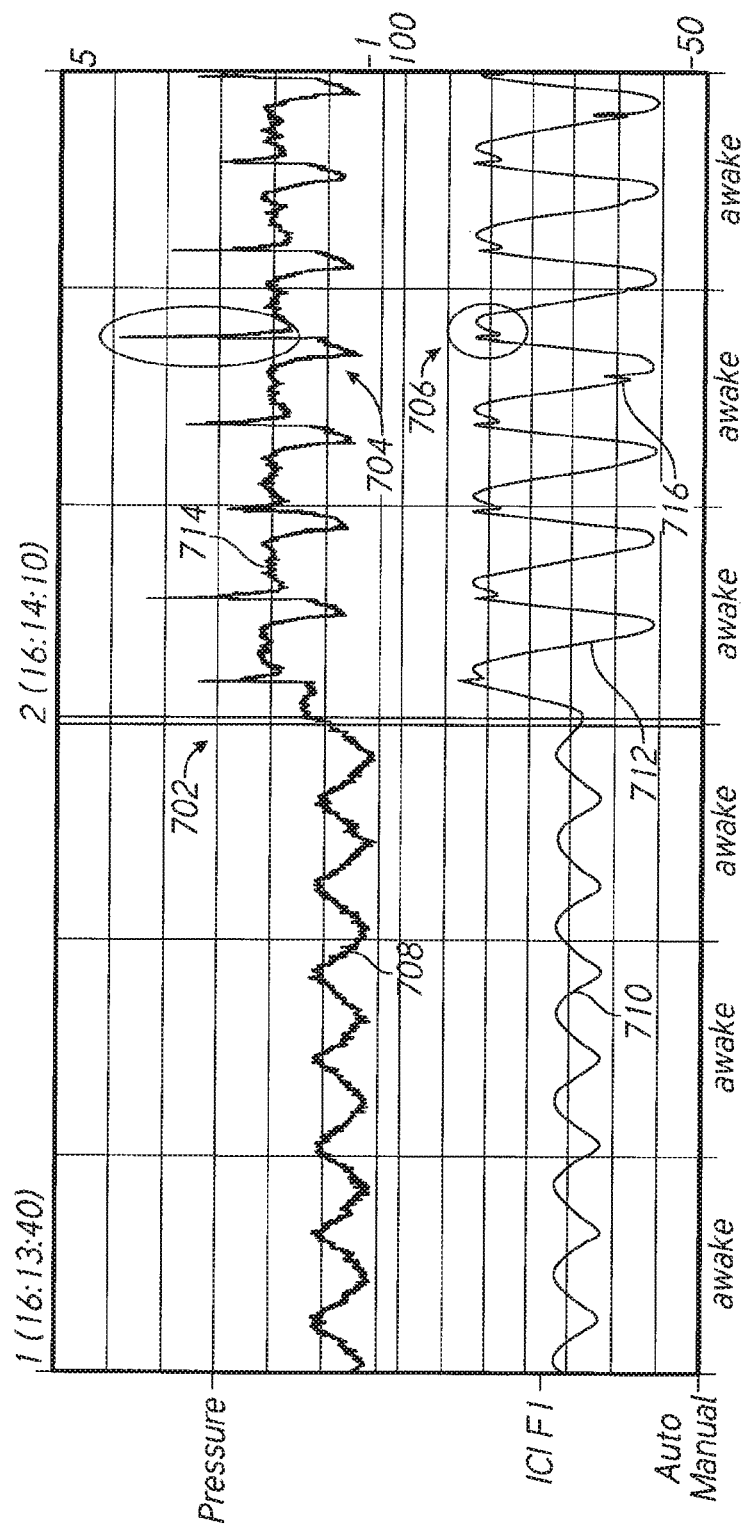
FIGS. 7A and 7B are plots that show flow and pressure versus time for each of two valves and illustrate differences in the valve characteristic between the two valves.
Figure 7B:
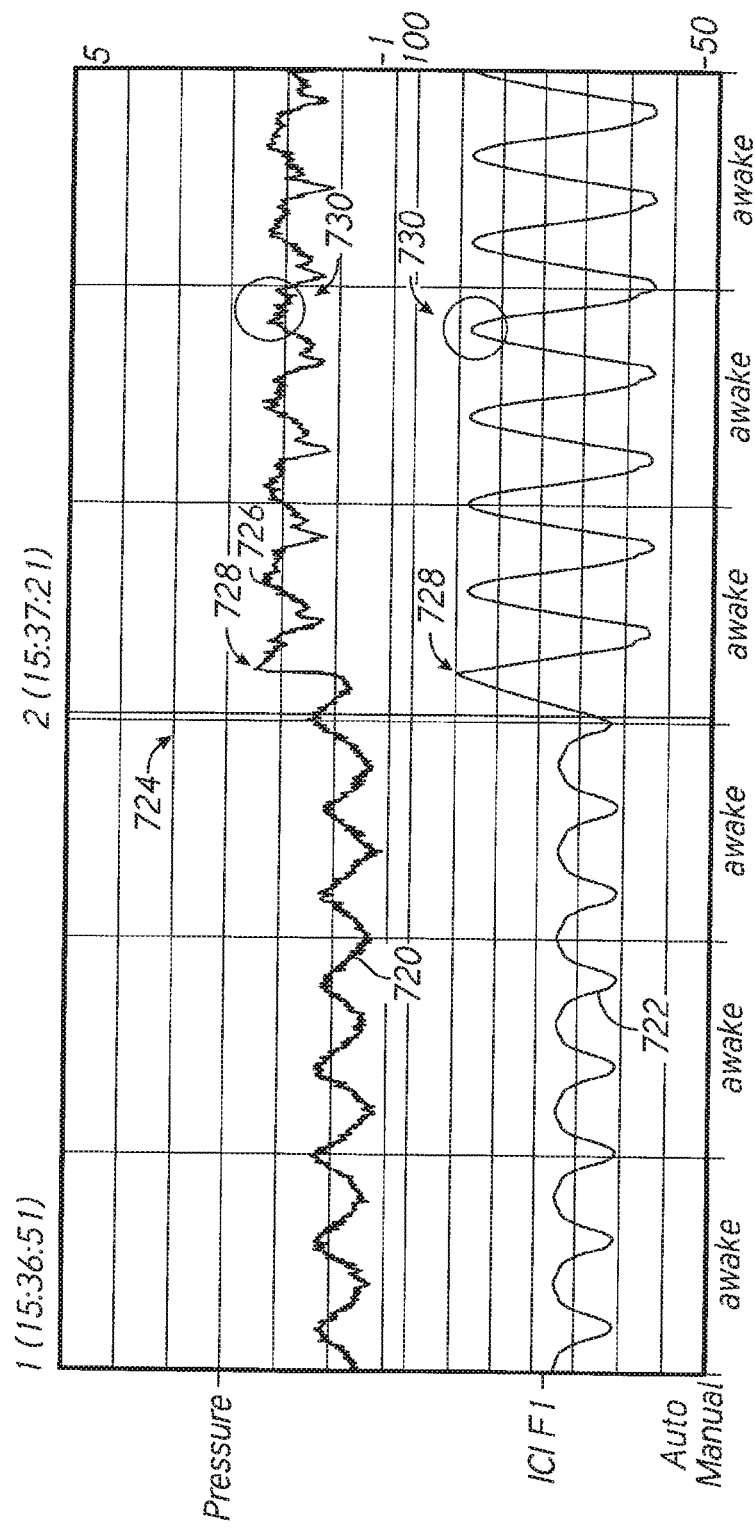

FIG. 7A plots the pressure and flow versus time for the ResMed Quattro valve. FIG. 7B plots the pressure and flow versus time for the valve of FIGS. 9A-9C.

Referring in particular to FIG. 7A, the pressure plot shows a first portion 708 while the flow generator is in constant speed mode and a second portion 714 after the flow generator transitions to pressure feedback mode with a set pressure of 1.5 cm H2O at time 702. With the flow generator in constant speed mode at portion 708, the pressure fluctuates with the sinusoidal breathing pattern imposed by the artificial lung. After the transition to pressure feedback mode, the pressure feedback control is trying to assert control over the pressure and reduces the influence of the imposed breathing.

In the flow plot, portion 710 precedes the transition 702 and portion 712 is after the transition 702. In portion 710, the flow fluctuates with user breathing approximately opposing the fluctuation of pressure. As the artificial lung exhales, the pressure rises and the delivered flow reduces. As the artificial lung inhales, the pressure drops and the delivered flow increases.

After the transition 702, the delivered flow 712 remains in phase with the user breathing. The delivered pressure 714 is more complex, as the feedback control tries to respond to the instantaneous pressure.

One feature of these plots is that the set pressure of 1.5 cm H2O has not been sufficient to bring this valve into a stable, closed condition. This is illustrated by the highlighted spikes 704 in the pressure plot and the highlighted irregularity 706 in the flow plot. The spike 704 and the irregularity 706 occur in each breath in the sequence after entering the pressure feedback mode. The spikes and irregularities indicate that the valve is unstable at 1.5 cm H2O and correspond with the valve snapping shut. The valve then reopens at some point in the cycle and snaps shut again at the start of the next exhalation.

FIG. 7B shows similar plots for the valve illustrated in FIGS. 9A-9C. Again, the plots include portions 720, 722 prior to a transition 724 to the pressure feedback control with a set pressure of about 1.5 cm H2O. For this valve, the difference in average pressure between the period 720 prior to the transition 724 and the period 726 after the transition 724 is lower than the difference in average pressure during the period 708 and average pressure in period 714 for the ResMed Quattro valve. Despite this, the valve of FIGS. 9A-9C has entered a stable closed condition at moment 728 and, as indicated at 730, there are no conspicuous spikes in the pressure plot and no significant discontinuity peaks or irregularities of the flow curve. This corresponds with the observation that the valve had entered a stable, closed condition.

Thus, the valve of FIGS. 9A-9C outperforms the ResMed anti-asphyxia valve by achieving stable closed behaviour at a lower delivered pressure and with a smaller increase in system conditions from a stable open condition.

Figure 8A:
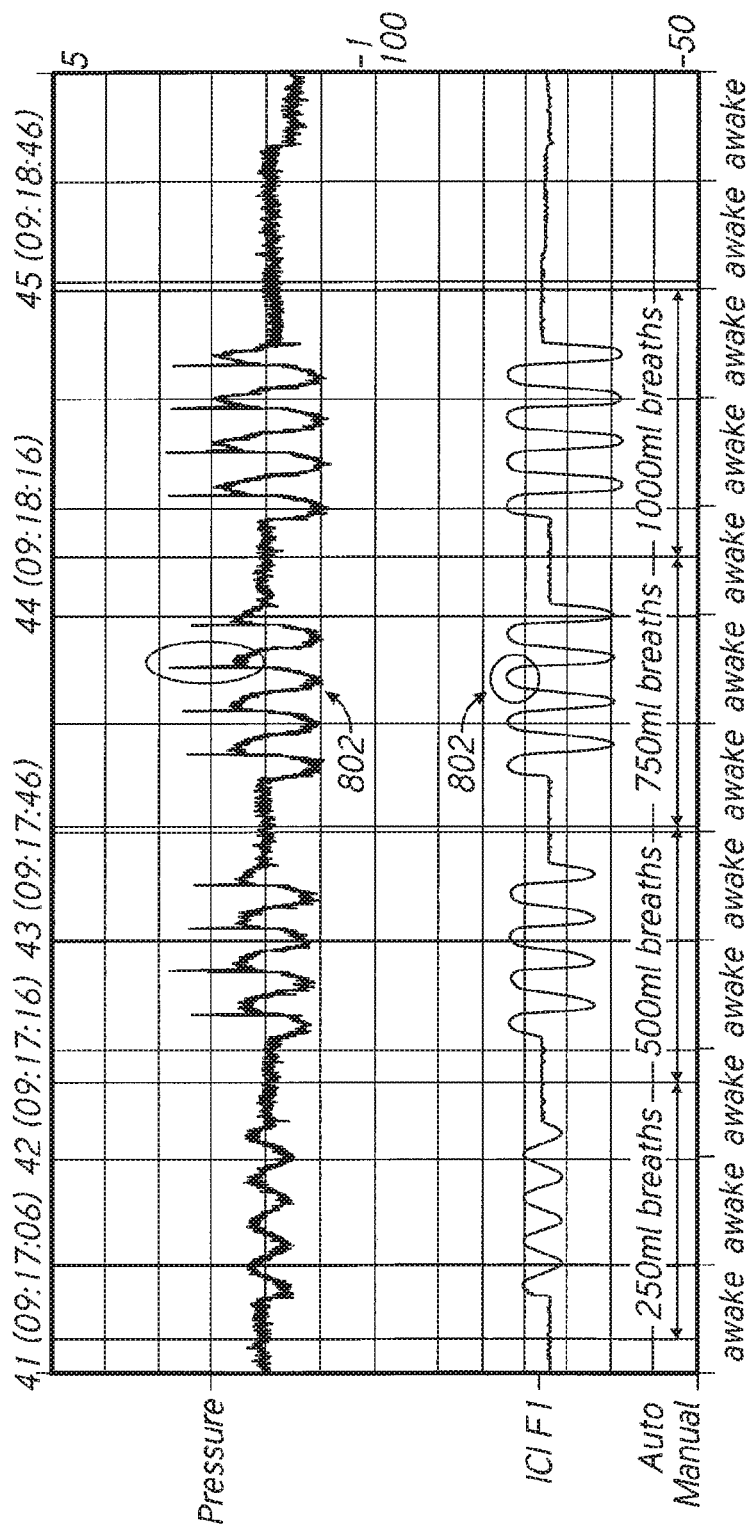
FIGS. 8A and 8B are plots that show flow and pressure versus time that illustrate differences between operating in a flow control mode when the valves are on the verge of closing and operating in a pressure control mode.
Figure 8B:
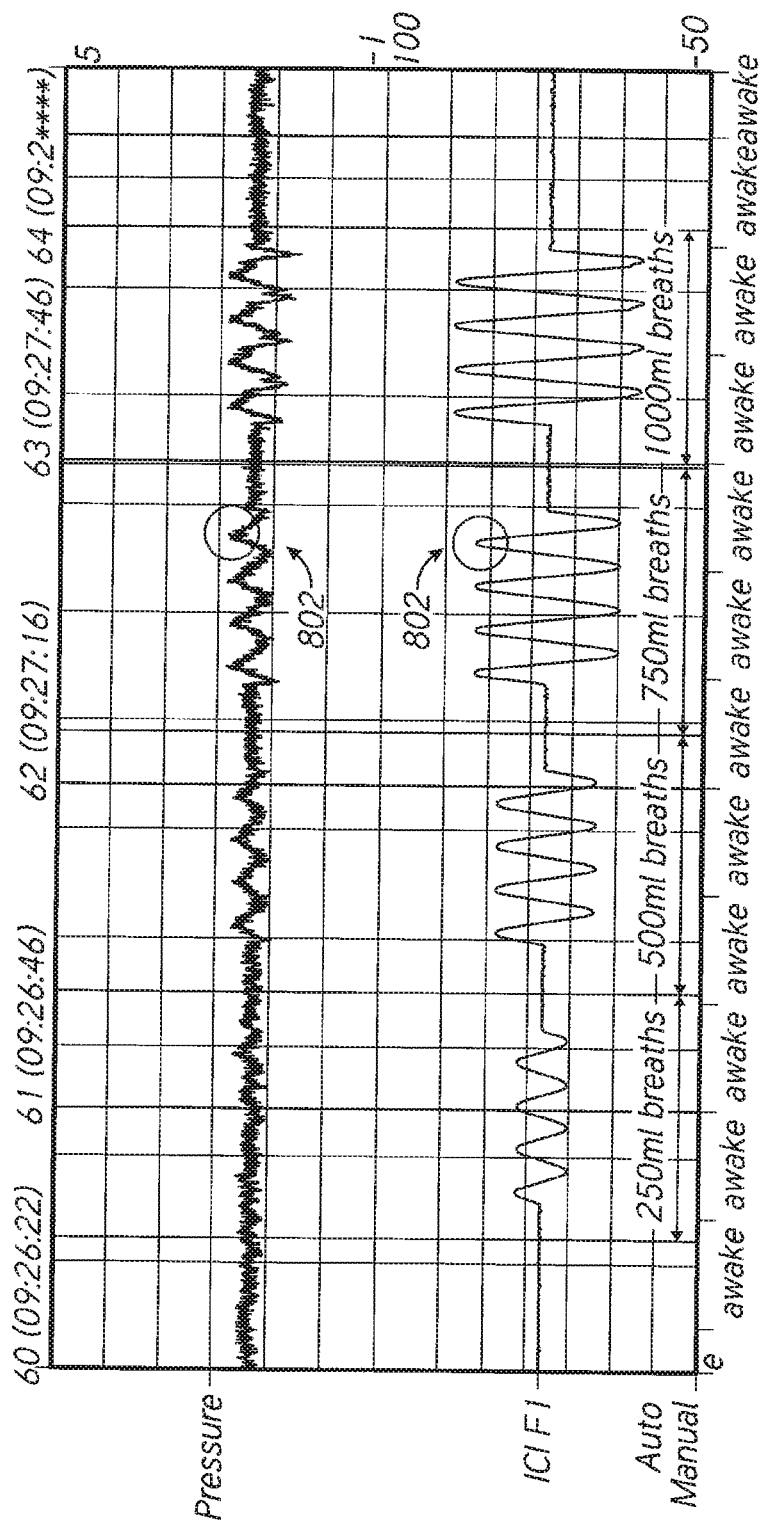

FIGS. 8A and 8B illustrate different characteristics under open loop control and under pressure feedback control for the valve of FIGS. 9A-9C. FIG. 8A illustrates features that correspond to valve instability. FIG. 8B illustrates the effect of pressure feedback on flow fluctuation. Both FIG. 8A and FIG. 8B relate to the valve in the closed state. The sequence was run firstly with the flow generator controlled to have a constant rotor speed of 5000 rpm. In the second test, the flow generator was operated in a pressure feedback mode with a set pressure of 1.5 cm H2O.

The behaviour of the valve of FIGS. 9A-9C was observed in the two modes. Furthermore, the flow and pressure were recorded throughout the tests.

FIG. 8A provides flow and pressure versus time plots for the test conducted with open loop control and with the CPAP speed controlled at 5000 rpm. FIG. 8B shows the pressure and flow versus time plots with pressure feedback control and with the CPAP flow generator pressure set to about 1.5 cm H2O.

FIG. 8A illustrates that the illustrated valve is becoming unstable with a blower speed at 5000 rpm having previously been higher. Instability in FIG. 8A is indicated by the pressure spike 802 becoming apparent in the early part of expiration in each breath.

This can be compared with the performance of the valve recorded in FIG. 8B in the pressure control mode. In the pressure control mode, with a set pressure of 1.5 cm H2O, there are no large transient peaks in the pressure curve, indicating that the valve is stable. However, the peak to peak flow fluctuation is much greater than the flow fluctuation in the open loop control mode illustrated in FIG. 8A.

Overview of Operating Characteristics of Flow Diversion Device and Control Techniques Desirably, the flow diversion device and the control of the flow generator work in cooperation with one another. In some configurations, with the flow generator not generating flow, the user will inhale ambient air through the port of the flow diversion device and exhale air mostly out to ambient through the port. During exhalation, some small portion of the exhaled gases may push the valve member to bend the valve member downward toward the flow generator and a small portion of the exhaled gases may travel down the conduit beyond the valve member.

In some configurations, with the flow generator generating a sub-therapeutic flow of gases (i.e., flow control mode), the user will inhale mostly ambient air through the port while the flow from the flow generator bends the valve slightly toward the user and, as such, provides a small portion of flow to the user. During exhalation, most of the exhalation passes through the port with some portion of the exhalation moving the valve member back toward the flow generator, which slows the flow from the flow generator. Dependent upon the exhalation flow from the user, the flow rate from the user may vary. Thus, the varying flow rate may be indicative of the user breathing, which enables the controller 224 to monitor breathing patterns and identify events (e.g., apnea).

In some configurations, with the flow generator generating a therapeutic flow of gases (i.e., pressure control mode), during inhalation, the valve member overlies the port and the user breathes gases from the flow generator. During exhalation, the user breathes against the flow from the flow generator and the valve member overlies the port.

In some configurations, the flow diversion device includes an adaptable venting arrangement configured to change a size of a venting area, the venting area providing a path between the flow diversion device and ambient. For example, the valves described herein with reference to FIGS. 9, 10, 12, and 13 can be configured to change a size of a venting area by variably occluding the port to ambient. In like manner, other valves or similar devices can be included in the flow diversion device to work in cooperation with the control of the flow generator to provide desired, selected, or defined flows or pressures by changing a size of the venting area.

The adaptable venting arrangement can be used in cooperation with the control of the flow generator to provide, for example, relatively lower pressures (compared to systems with fixed venting arrangements) when operating in a sub-therapeutic mode. For example, when the system operates in the sub-therapeutic mode (e.g., when the system determines the user is awake), the venting arrangement can be configured to have a venting area that is at least about 60 mm2, at least about 40 mm2, at least about 30 mm2, or at least about 20 mm2. In some configurations, when the adaptable venting arrangement provides a venting area of about 60 mm2, the gases pressure can be less than or equal to about 1 cm H2O or less than or equal to about 0.5 cm H2O. Decreasing the size of the venting area can increase the pressure in the system. Increasing the size of the venting area can decrease the pressure in the system but it can also decrease a flow. Decreasing the flow can be disadvantageous if the flow decreases to a point where it can no longer flush the user interface. In some configurations, the system can be adapted to provide sufficient flow to flush the user interface when the venting area is about 60 mm2 and the gases pressure is less than or equal to about 0.5 cm H2O. For example, with the venting area at least about 60 mm2 and the gases pressure less than or equal to about 0.5 cm H2O, the flow generator can be configured to provide a flow of at least about 15 litres per minute, at least about 12 litres per minute, or at least about 10 litres per minute. It can be desirable to supply pressure at or near atmospheric pressure in the sub-therapeutic mode to increase comfort of the user, thus it may be desirable to increase the size of the venting area while maintaining a sufficient flow to flush the user interface.

In some embodiments, the system is configured to change a state of CO2 removal based at least in part on sleep state to maintain a minimum level of CO2 removal from the system. CO2 removal can be at a first state when the patient is determined to be awake and at a second state when the patient is determined to be asleep. Alternatively a level of CO2 removal arrangement may stay constant throughout operation of the device in different mode to maintain the minimum required level of CO2 removal from the system.

Figure 14:
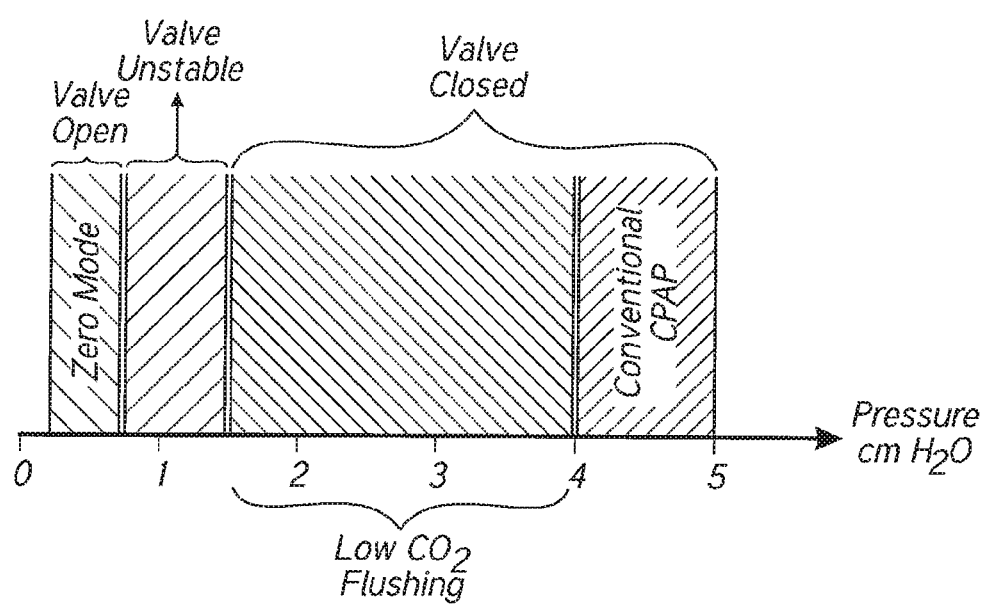
FIG. 14 is a graphical depiction illustrating a relationship among valve position, various modes of operation and operating pressures.

With reference now to FIG. 14, when using valves such as those described above, there is a transition of the valve from an open position (e.g., sub-therapeutic pressures) to a closed position (e.g., therapeutic pressures). As illustrated, in a so-called "zero" mode, during which the valve does not overlie the port, the valve is opened. In the illustrated configuration, the valve closes or substantially closes the port in both the low carbon dioxide flushing mode and in the conventional CPAP mode (e.g., therapeutic mode). In between the zero mode and the low carbon dioxide flushing mode, the valve is substantially unstable. The region in which the valve is generally unstable preferably is minimized by rapidly progressing between the two adjoining modes. Moreover, time spend in the low carbon dioxide flushing mode preferably also is minimized by rapidly progressing between the zero mode and the conventional CPAP mode.

In some configurations, the valve can be moved to the closed position through a step change that increases the pressure from a zero mode pressure (e.g., about 0.5 cm H20) to at least a low carbon dioxide flushing mode (e.g., about 2.0 cm H2O). The step change results in the valve moving from open to closed without dwelling within the valve unstable range. Following the step change, the pressure then can be increased into the conventional CPAP range quickly to minimize time in the low carbon dioxide flushing zone.

Figures 15A, 15B, 15C:
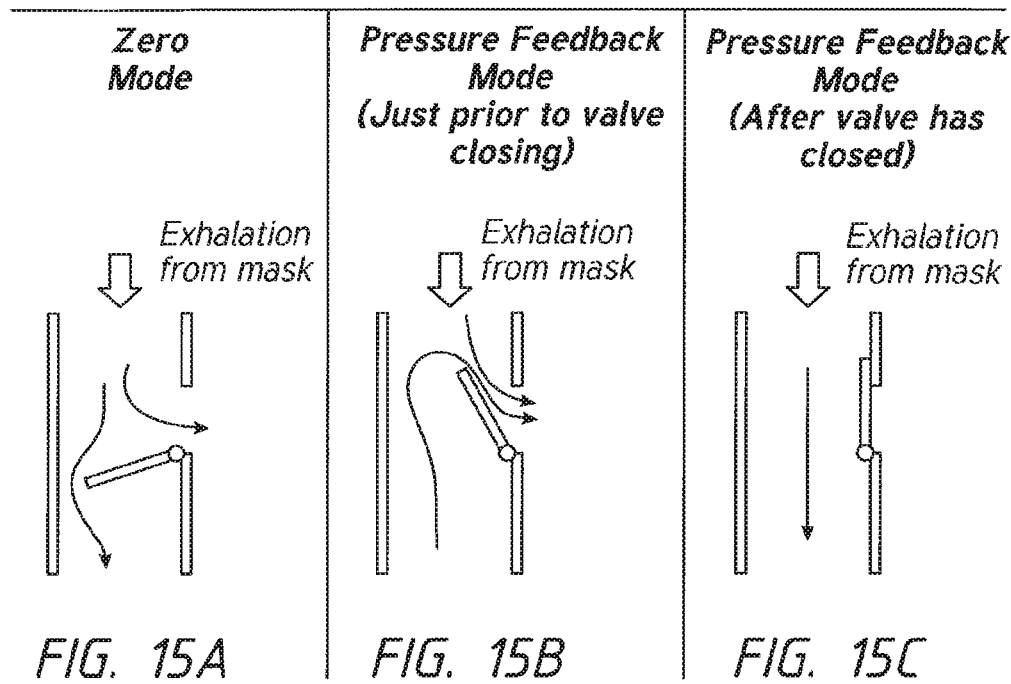
FIGS. 15a-15c are schematic depictions of valve closure during exhalation.
Figures 16A, 16B, 16C:
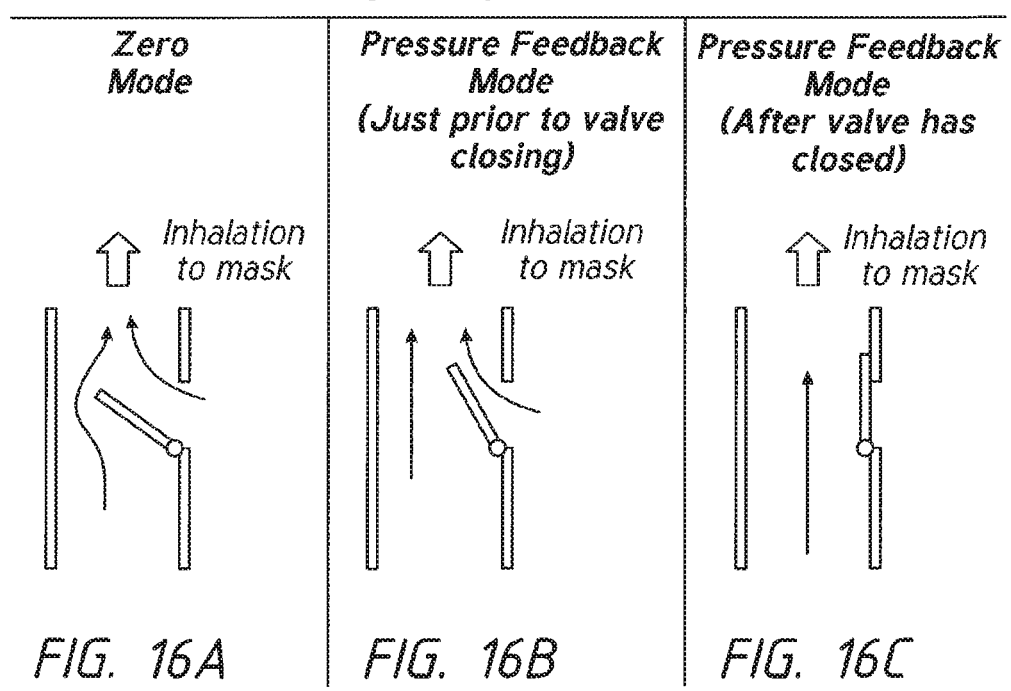
FIGS. 16a-16c are schematic depictions of valve closure during inhalation.

It has been found, however, that the step change from zero mode to low carbon dioxide flushing mode or conventional CPAP mode can result in an audible thud caused by the valve slapping shut and also can result in a pressure spike experienced by the user. Both of these results are undesired. With reference to FIGS. 13a-13c, uncontrolled transition from zero mode to low carbon dioxide flushing or conventional CPAP mode is schematically shown. As illustrated, the transition can occur during exhalation if uncontrolled. In zero mode, as shown in FIG. 15a, during exhalation, a portion of the exhaled air passes through the port to ambient while a smaller portion of the exhaled air passes the deflected valve. As the pressure increases prior to the valve closing, if the user exhales, the air being delivered from the pressure source as well as the exhaled air passes through the port to ambient, which works to keep the valve from fully sealing shut. When the valve fully closes, the user continues to exhale against the flow from the pressure source, which can no longer escape through the now closed port. The closing of the valve greatly reduces or prevents the diversion of flow from the pressure source and, therefore, the closing of the valve is experienced by the user as a sudden pressure spike, and operation then can continue with the valve occluding the port to ambient.

FIGS. 14a-14c illustrate the behavior of the valve when closing during an inhalation cycle. Comparing FIGS. 13a-13c to FIGS. 14a-14c demonstrates the improved closing and helps explain why a pressure spike is not experienced with the closing of the valve. As illustrated in FIG. 15a, during zero mode, a small portion of the air originates from the pressure source while a larger portion of the air flows in through the port from ambient. As the pressure of the pressure source increases, the valve moves toward a closed position, which decreases the flow from ambient through the port while increasing the flow from the pressure source. Finally, when the valve is fully closed, the pressure source supplies the full flow to the user. Thus, closing of the valve during inhalation does not result in a significant pressure spike and allows the valve to close more quietly.

Figure 17:
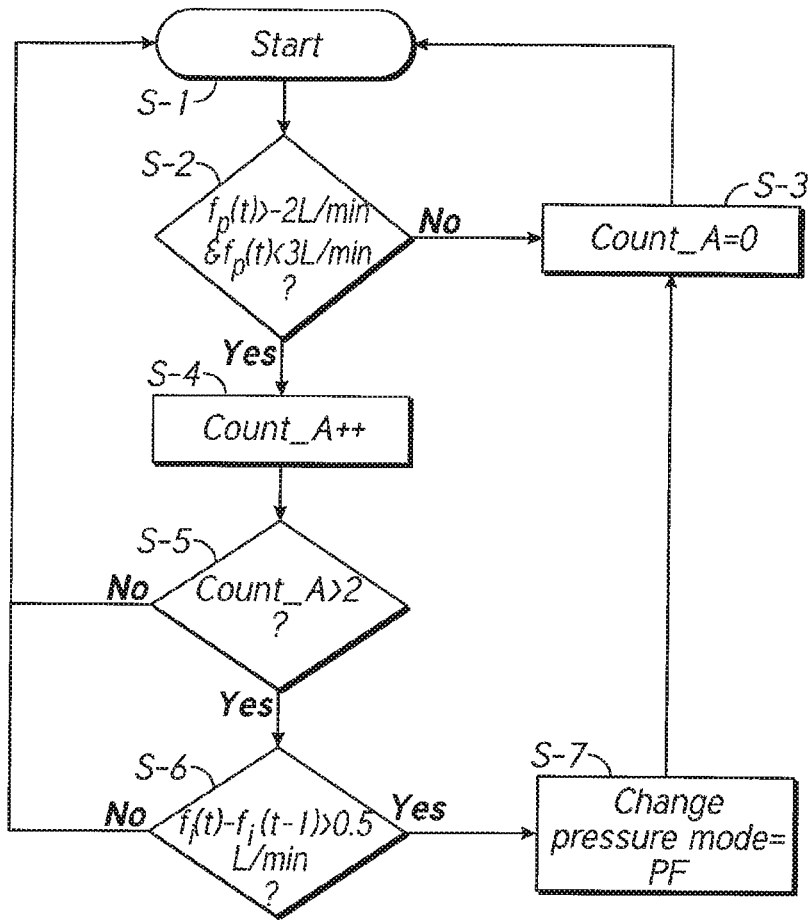
FIG. 17 is a flow routine for controlled closing of a valve during inspiration.

FIG. 17 illustrates a control routine that can be used to transition the valve from open to closed during an inhalation of the user. The decision to transition the valve can be made using any suitable routine.

The control routine of FIG. 17 can be implemented in any suitable manner. In some configurations, the routine can be initiated every 20 ms or as frequently as desired. Desirably, each finite increase in pressure is synchronized with the onset of spontaneous inspiration. In some configurations, the total number of breaths and the number of breaths where change is applied can be used to determine the speed of adjustments in pressure between two levels of positive pressure.

With reference to FIG. 17, upon starting (S-1), the routine evaluates the patient respiration rate. For example, the patient respiration rate ($f_p(t)$) can be determined using the average flow rate ($f_b(t)$=average flow*100) and the instantaneous flow rate ($f_i(t)$) using the following relationship:

$$f_p(t)=f_i(t)-f_b(t)$$

The flow rate can be determined using any suitable sensing arrangement. In some configurations, a differential pressure flow sensor can be used such that flow in a first direction can be differentiated from flow in a second direction. In general, in one configuration, the flow rate at the start of inspiration will be higher than the flow rate during expiration because exhaled gases work against the flow from the pressure source. Thus, the patient respiration rate takes into account instantaneous changes in the flow rate, which can be used to determine the onset of an inspiratory cycle.

The patient respiration rate $f_p(t)$ then can be compared against a range to determine when the calculated patient respiration rate $f_p(t)$ falls within a range indicative of inspiration. See S-2. In the illustrated configuration, the calculated respiration rate $f_p(t)$ is compared to a range of between about −2 L/min and about 3 L/min. Other ranges also are possible.

If the calculated patient respiration rate $f_p(t)$ falls outside of this range, a counter is cleared and the routine begins again. See S-3. On the other hand, if the calculated patient respiration rate $f_p(t)$ falls within this range, the counter is increased (see S-4) and the instantaneous flow value $f_i(t)$ is stored. The counter also is checked against a value (see S-5). In the illustrated configuration, the counter is checked against the value 2. By using the counter, transient fluctuations can be filtered and such that a non-inspiratory fluctuation will be less likely to cause a change in pressure. If the counter has not exceeded the value (see S-5), then the routine continues checking the calculated patient respiration rate until the counter exceeds the value.

When the counter exceeds the value, then the difference between the most recent instantaneous flow rate $f_i(t)$ and the stored instantaneous flow rate $f_i(t-1)$ are compared against a flow rate value indicative of fluctuation (e.g., 0.5 L/min). (see S-6). If the product does not exceed this value, then the routine repeats. If the product does exceed this value, then the routine indicates a change from zero mode to pressure mode (e.g., conventional CPAP mode) (see S-7) and the counter is reset (see S-3).

Through implementation of the routine set forth in FIG. 17, it is possible to time pressure increases from zero mode into a pressure control mode with patient inspiration. Such a timing results in less perceived pressure spikes and less perceived valve slap or noise. While less important to patient perception, changing from pressure feedback mode to zero mode can be performed in a manner that employs decreases in pressure that coincide with patient exhalation. By instituting such a change, it is possible to decrease a perceived "air starvation" sensation that might otherwise be experienced by the user when the pressure source changes to a substantially constant speed mode, which can be used during zero mode.

Figure 18:
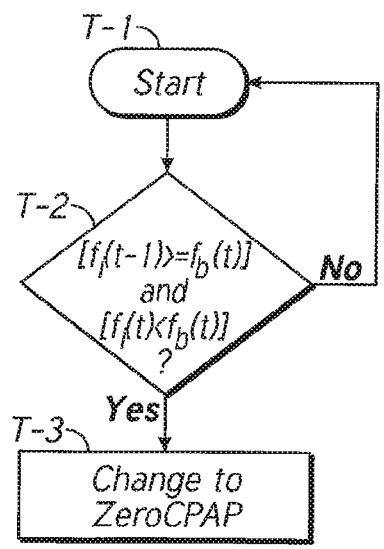
FIG. 18 is a flow routine for controlled opening of a valve during exhalation.

FIG. 18 illustrates an example of a routine that can be used to facilitate transition from pressure feedback mode to zero mode. The control routine of FIG. 18 can be implemented in any suitable manner. In some configurations, the routine can be initiated every 20 ms or as frequently as desired. Desirably, each finite decrease in pressure is synchronized with the onset of spontaneous exhalation. With reference to FIG. 18, upon starting (T-1), the routine compares a stored value of the instantaneous flow rate ($f_i(t-1)$) and the current value of the instantaneous flow rate ($f_i(t)$) against the current average flow rate ($f_b(t)$=average flow*100). See T-2. If the prior instantaneous flow rate is greater than or equal to the average flow rate and if the current instantaneous flow rate is less than the average flow rate, then the routine initiates a change to zero mode. If not, then the routine continues to monitor for the condition under which the routine will transition to zero mode.

Figure 19:
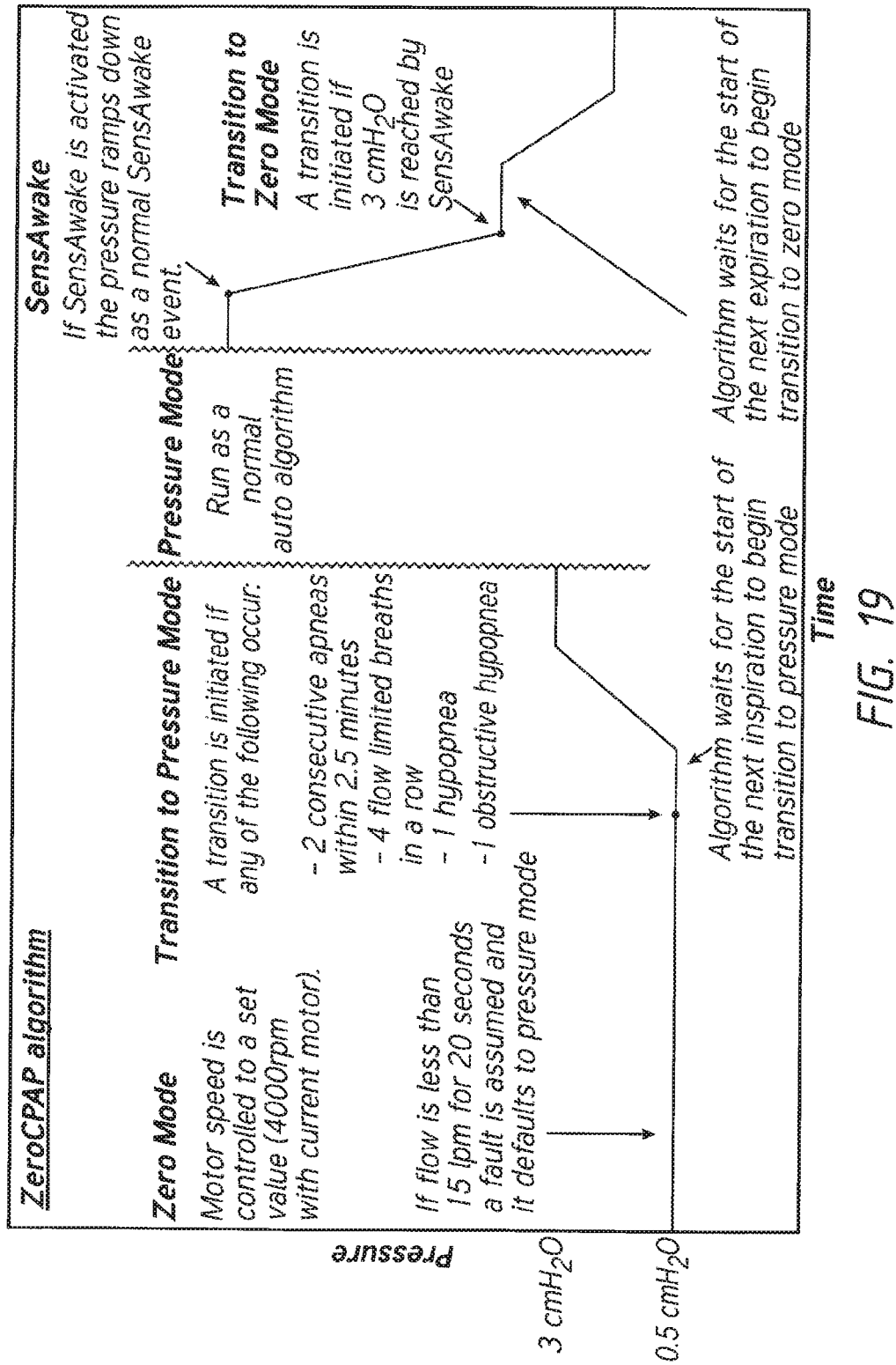
FIG. 19 is a graphical representation of a system control implementation.

FIG. 19 graphically illustrates an implementation that involves a zero mode and a pressure mode. As illustrated, the implementation can operate in a zero mode, during which a sub-therapeutic pressure is supplying a base level of flow and/or a base level of pressure to a user. The implementation also can operate in a pressure mode, during which suitable therapeutic pressure or pressures can be supplied.

In the zero mode, the pressure source can supply at least sufficient flow to flush an interface (e.g., mask) of a user. In some configurations, the instantaneous flow rate can be monitored and if the instantaneous flow rate drops to a flow of less than a set value (e.g., about 15 L/min) for a set period of time (e.g., 20 seconds), then a fault can be assumed and the implementation can proceed to operate in a pressure mode, whereby sufficient flow can be provided to continuously flush the interface through a bias flow.

In some configurations, during the zero mode, the pressure source provides an average flow of at least about 15 L/min. In a configuration where the pressure source is a fan driven by a motor, the motor can be driven to supply the desired flow rate. In one configuration, the motor operates at a set value, which can be about 4000 rpm in some applications. In some configurations, during the zero mode, the pressure source provides an average low pressure of at less than or equal to about 3 cm H2O, or less than or equal to about 0.5 cm H2O. In a configuration where the pressure source is a fan driven by a motor, the motor can be driven to supply the desired low pressure.

As illustrated, at some point, the implementation transitions from zero mode to pressure mode. Preferably, the transition is after a user is detected to be sleeping or after events occur that result in an assumption that the user is sleeping. For example, in some applications, a transition occurs if the user experiences two or more apneas within a short window of time (e.g., 2.5 minutes). In some applications, a transition occurs if the user experiences four or more flow limited breaths in a row. In some applications, a transition occurs if a single hypopnea is experienced by the user. In some applications, a transition occurs if a single obstructive hypopnea is experienced by the user. In some applications, a transition occurs if a combination of apnea, hypopnea and flow limited breaths is experienced by the user. In one application, the condition or conditions of one or more of these examples can be monitored and a transition initiated when any is detected.

As discussed above, to control valve operation, the transition from zero mode to pressure mode can occur during inhalation. In some applications, the transition from zero mode to pressure mode can occur at the onset of inhalation. Preferably, the transition involves increasing the applied pressure to a point that results in the valve closing the port to ambient, as discussed above. In one configuration, zero mode involves operation of the pressure source at or around about 0.5 cm H2O and pressure mode can be initiated with an increase in pressure to about 3.0 cm H2O.

Following a transition from zero mode to pressure mode, the implementation can apply pressure in accordance with any suitable technique. In the arrangement illustrated in FIG. 19, the applied pressure can be reduced when the user is determined to have awakened or when the user is determined to be in the process of awakening. Any suitable technique can be used for determining when the user has awakened or is awakening. As the pressure is reduced, if the pressure reaches a minimum pressure (e.g., 3.0 cm H2O), then the implementation can await an exhalation and transition back to zero mode during an exhalation. In some applications, the pressure also can be reduced during pressure mode during exhalation.

Figure 20:
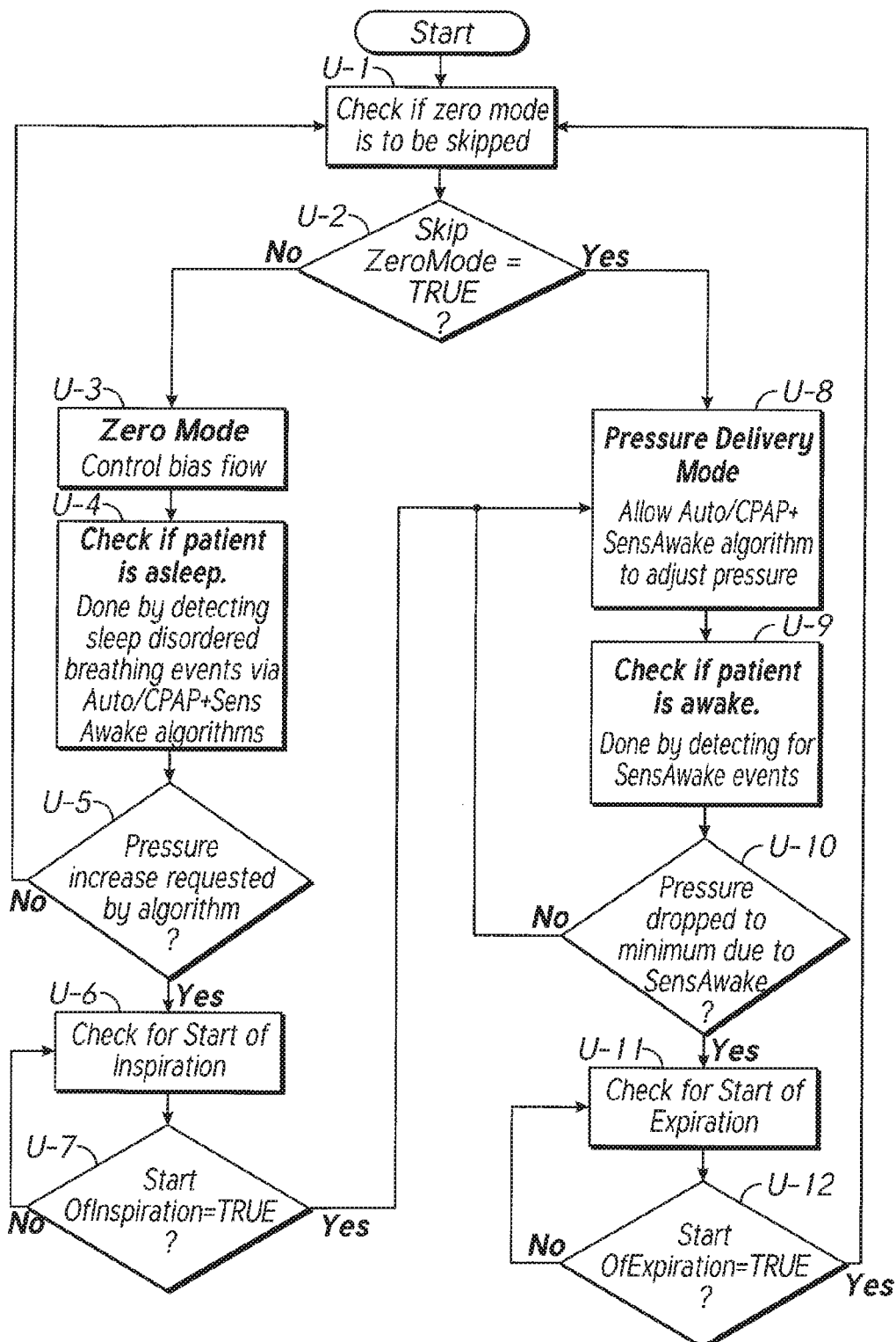
FIG. 20 is a flow routine for changing between zero mode and pressure mode.

FIG. 20 is an example of a control routine that can be used to achieve the implementation graphically depicted in FIG. 19. With reference to FIG. 20, the routine can begin, for example, when the breathing apparatus (e.g., positive pressure apparatus such as a CPAP machine) is powered up. The routine begins by determining whether there is an indication that the apparatus should not operate in the zero mode. See U-1.

In some applications, the use of a zero mode is dependent upon the presence of a valve through which a user can draw ambient air to supplement air provided at the lower pressures of the zero mode. Thus, in some applications, a changeable setting can be provided on the apparatus that indicates whether the zero mode should be skipped or used. In one or more of such applications, the user or a designee of the user can adjust that setting. In some applications, the component containing the valve can communicate with the apparatus such that the apparatus can determine whether or not the valve is present. For example, the valve can be provided with a wireless communication device, such as an RFID tag for example but without limitation, such that the presence of the valve can be conveyed to the apparatus. By way of another example, where a heated conduit is used with the apparatus or where the conduit otherwise contains one or more wires, the presence of the valve can be indicated by a wired connection.

Figure 21:
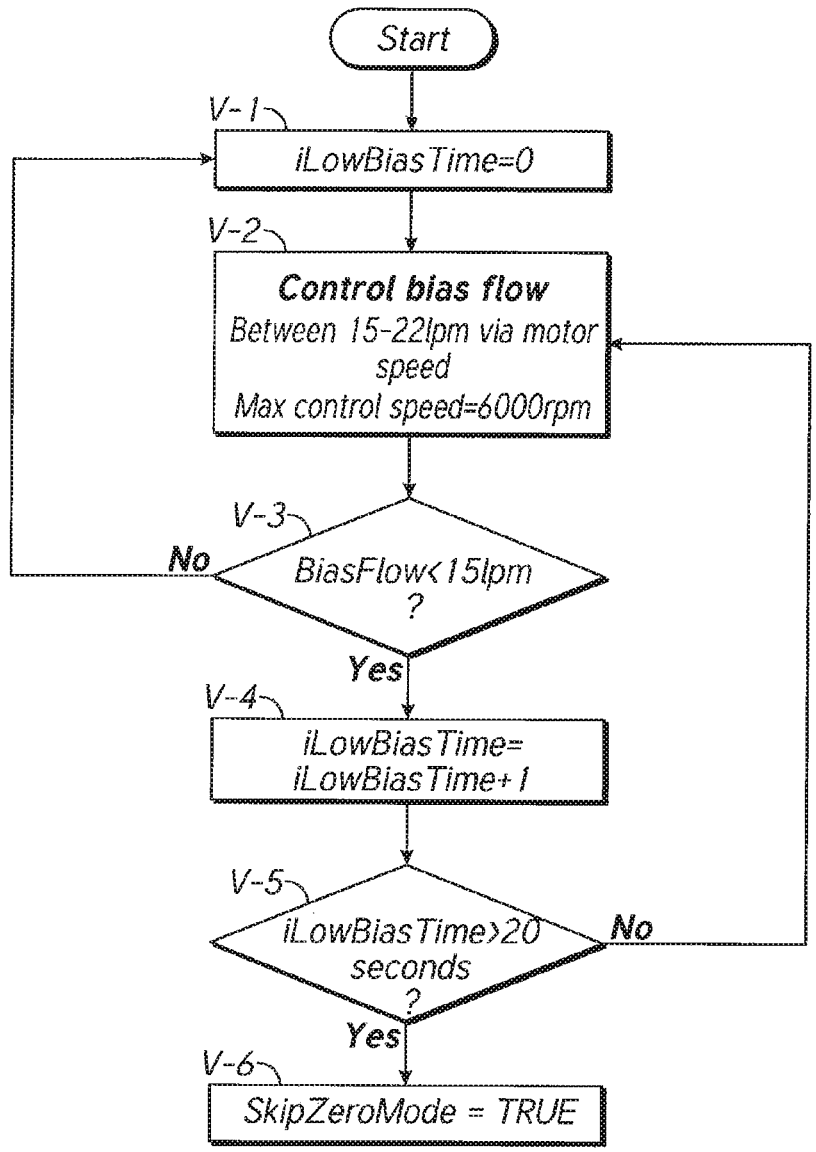
FIG. 21 is a flow routine for determining if zero mode should be skipped.

FIG. 21 illustrates a subroutine for determining whether zero mode should be used or not based upon flow characteristics. As illustrated, a variable used for timing an event is initialized. See V-1. With the timing variable initialized, the subroutine enters into a bias flow control operation. See V-2. The bias flow can be controlled, for example, by controlling the motor speed. Preferably, the bias flow is controlled to a level of between about 15 L/min and about 22 L/min. In some configurations, the motor speed has an upper limit of about 6000 rpm but other configurations are possible.

As shown, during the bias flow control, the average bias flow is monitored. Desirably, a minimum level of flow is provided. In the illustrated configuration, a level above about 15 L/min is desired. See V-3. If the level of about 15 L/min is exceeded, then the subroutine continues to monitor the bias flow level. If the bias flow level decreases below about 15 L/min, then the time below that level is incremented. See V-4. When the time below 15 L/min exceeds 20 seconds (see V-5), then a flag is set to cause the apparatus to skip zero mode. See V-6. Otherwise, the level simply continues to be monitored.

Returning to FIG. 20, the flag relating to whether or not to skip the zero mode is checked. See U-2. If the zero mode is not to be skipped, then bias flow is controlled such that the bias flow level is maintained at a desired level, which level preferably is within the range of about 15-22 L/min. See U-3. In some configurations, the zero mode control of bias flow institutes the subroutine of FIG. 21 to reduce the likelihood of the bias flow decreasing to a level that will not adequately flush the interface.

The user is monitored while the apparatus supplies the sub-therapeutic pressure. In particular, the user can be monitored to determine when the user has fallen asleep. Any suitable technique can be used. In some configurations, sleep disordered breathing events can be detected using any suitable technique. For example, techniques described in U.S. Pat. Nos. 7,882,834 and 6,988,994, each of which is hereby incorporated by reference in its entirety, can be used to detect events. See U-4. So long as no pressure increase is requested, the subroutine continues to loop. If a pressure increase is requested or if the system enters into the pressure control mode, then the system awaits the onset of inhalation.

Figure 22:
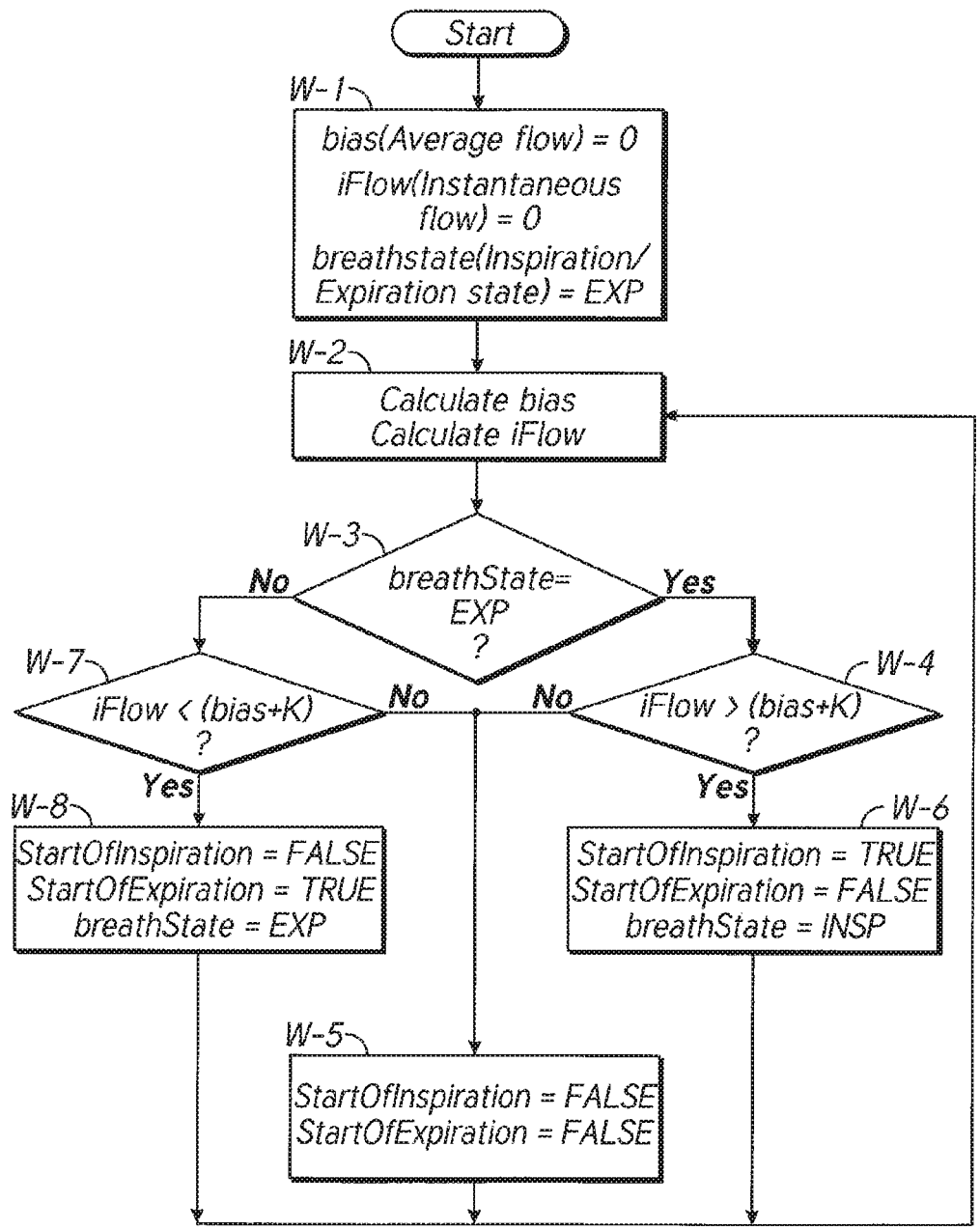
FIG. 22 is a flow routine for determining an onset of inhalation and an onset of exhalation.

FIG. 22 illustrates a subroutine for determining when a user is beginning to inhale and when a user is beginning to exhale. As illustrated in FIG. 22, when the routine starts, values can be initialized to starting values. See W-1. For example, in the illustrated configuration, a bias value, which represents an average flow rate over a period of time (e.g., 7.5 seconds) can be set to 0 as can the iFlow value, which relates to the instantaneous flow. In addition, a flag that is indicative of whether the user is inhaling or exhaling can be set to a value. While the illustrated configuration shows the breathState variable being set to EXP, which represents exhalation, other values also can be used (e.g., INSP). See W-1.

The subroutine shown in FIG. 22 calculates the bias variable (i.e., the average flow rate) based upon the sensed iFlow variable (i.e., the instantaneous flow). In some configurations, as discussed directly above, the bias variable is a rolling average taken over a set period of time. In one configuration, the period of time is about 7.5 seconds but other periods of time can be used. See W-2.

Once a set of values have been obtained for the iFlow and bias variables, the subroutine continues by checking the breathState flag to determine if the user has been determined to be inhaling or exhaling. See W-3. If the flag indicates that the most recent indication has been exhaling (i.e., breathState=EXP), then the most current instantaneous flow rate (i.e., iFlow) is compared to the sum of the average flow rate (i.e., bias) and a constant K.

Figure 23:
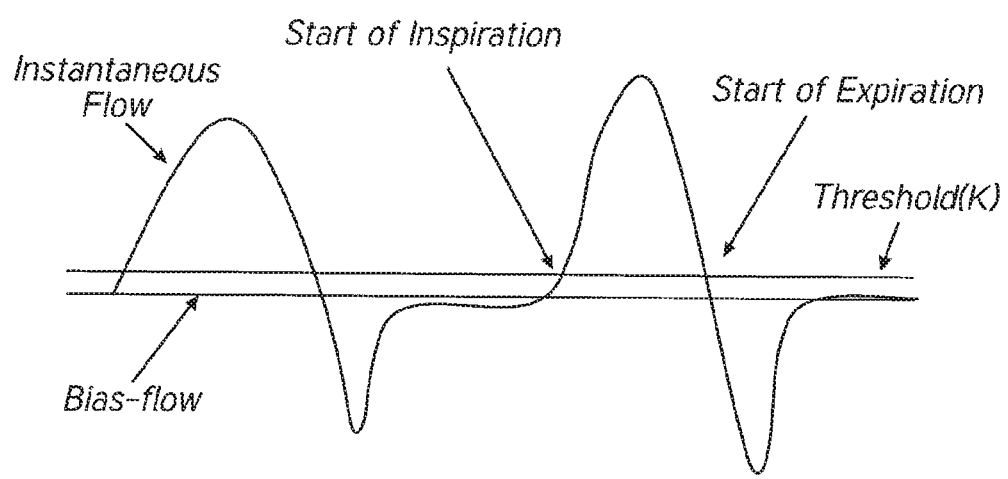
FIG. 23 is a graphical representation of a breathing pattern.

As shown in FIG. 23, it has been determined that the use of constant K allows a more consistent determination of the onset of inhalation. The dashed generally horizontal line indicates a generally steady bias flow from the pressure source. Superimposed onto this generally horizontal line is a generally sinusoidal line representing the flow from a user during breathing. Because of the dwell period during inspiration where the breathing flow rate is substantially constant and generally equal to the bias flow rate, Applicant has determined that using a constant K allows the triggering value to be higher than a level likely to be achieved by noise in the system, including the sensors. In some configurations, the constant K is about 2 L/min. In some applications, the constant K is about 400% of the bias flow rate. Other values also can be used.

With reference again to FIG. 22, if the sum of the average flow and the constant is not greater than the instantaneous flow, then a flag indicative of the start of inspiration is set to false and a flag indicative of the start of exhalation is set to false (see W-5) because the user is not initiating an inhalation nor is the user starting an exhalation (because the breathState flag indicated that exhalation already was ongoing. On the other hand, if the sum of the average flow and the constant is greater than the instantaneous flow, then the flag indicative of the start of inspiration is set to true, the flag indicative of the start of expiration is set to false and the breathState flag is changed to reflect that inspiration is occurring (e.g., the flag is set to INSP). See W-6. The routine then returns to W-2 for further evaluation of the flow rates.

With the breathState flag set to INSP instead of EXP, the subroutine then examines whether the instantaneous flow (i.e., iFlow) is less than the sum of the average flow (i.e., bias) and the constant (i.e., K). See W-7. If not, then it is determined that inspiration is ongoing and the flag indicating the start of inspiration is set to false while the flag indicative of the start of exhalation remains set to false. On the other hand, if the instantaneous flow has dropped to a flow rate below the sum of the bias flow and the constant, then it is determined that exhalation has begun. Accordingly, the flag indicating the start of inspiration is set to false, the flag indicative of the start of expiration is set to true and the flag indicative of the breathing state is set to indication exhalation (i.e., EXP). See W-8. The routine then returns to W-2.

Returning again to FIG. 20, with the determination of the onset of inspiration, the apparatus can create a change in pressure. See U-7. For example, in some configurations, the pressure can increase from about 0.5 cm H2O to about 3.0 cm H2O, which would be a sufficient increase in pressure to move the valve described above from the open position to the closed position. With the valve closed, the apparatus then can begin operating in a pressure delivery mode or pressure mode. See U-8. In some configurations, pressure increases in the pressure mode can be timed to generally correspond in time to inhalation while pressure decreases in the pressure mode can be timed to generally correspond in time to exhalation. Such timing can decrease the sensation by the user of the pressure changes. In some configurations, the pressure increase is a step change. In some configurations, the pressure increase is a gradual ramp. In some configurations, the pressure increase profile is substantially matched to the instantaneous flow profile to reduce or eliminate the sensation. Any suitable techniques can be used to adjust pressure, including those disclosed in U.S. Pat. No. 5,148,802, which is hereby incorporated by reference. While operating in the pressure mode, the user is monitored for signs of awakening. See U-9. For example, the breath waveform may change in frequency, amplitude or some other manner evidencing an irregularity that would indicate the user awakening. Any suitable techniques can be used, including but not limited to those disclosed in U.S. Pat. No. 6,988,994, which is hereby incorporated by reference in its entirety.

While operating in the pressure mode, the operating pressure may be decreased as a result of various factors. So long as the pressure is maintained above a minimum pressure, the pressure mode continues to operate as described above. See U-10. On the other hand, if the pressure drops to the minimum pressure, the system awaits a detection of the onset of expiration. See U-11 and U-12. When the user begins to exhale, the system decreases the pressure such that the valve opens and the system operates at a sub-therapeutic pressure sufficiently low to reduce the likelihood of the valve closing. In some configurations, prior to the system moving into the sub-therapeutic zone, the system ensures that the flag for skipping zero mode is not set to a value that would cause zero mode to be skipped.

Although certain features, aspects and advantages of the present invention have been described in terms of a certain embodiments, other embodiments apparent to those of ordinary skill in the art also are within the scope of this invention. Thus, various changes and modifications may be made without departing from the spirit and scope of the invention. For instance, various components may be repositioned as desired. In addition, certain features, aspects and advantages of the invention have been described with reference to breathing gases supply devices particularly for use in the treatment of obstructive sleep apnea. PAP devices also are used in the treatment of other conditions, such as COPD, and may be used for the supply of mixed gases other than air, for example, a mixture of air and oxygen, or a mixture of nitrogen and oxygen or the like. The method and apparatus of the present invention may be equally applied to gas supply apparatus for use in these other treatments. Moreover, not all of the features, aspects and advantages are necessarily required to practice the present invention. Accordingly, the scope of the present invention is intended to be defined only by the claims that follow.

What is claimed is:

1. A system configured to supply respiratory gases to a user wearing a user interface, the system comprising:
a flow generator; and
a controller controlling operation of the flow generator, the controller configured to: operate the flow generator in a first mode to create a first pressure that is below a therapeutic pressure range;
operate the flow generator in a second mode to create a second pressure that is within the therapeutic pressure range; and
transition from the first mode and the second mode in synchrony with inhalation of the user,
wherein the controller is configured to transition from the first mode to the second mode when the user is determined to be asleep, and to transition from the second mode to the first mode when the user is determined to be awake.

2. The system of claim 1, further comprising a flow diverter including a port to ambient, the port positioned between the user interface and the flow generator.

3. The system of claim 2, wherein the flow diverter further comprises a valve configured to assume a first position, where the valve substantially opens the port, and a second position where the valve substantially closes the port, and wherein the valve is configured to transition from the first position to the second position based on a transition from the first mode to the second mode.

4. The system of claim 1, wherein the controller is further configured to transition from the second mode to the first mode in synchrony with exhalation of the user.

5. The system of claim 4, wherein the valve is not actively controlled by the controller.

6. The system of claim 1, wherein the controller is further configured to monitor a flow rate while operating in the first mode, determine when the flow rate decreases below a lower threshold for a preset period of time, and transition to the second mode based on the determination.

7. The system of claim 1, wherein the second mode comprises a pressure mode.

8. The system of claim 1, wherein the controller is further configured to determine that the user is sleeping based upon a detection of sleep disordered breathing event.

9. The system of claim 1, wherein the controller is further configured to transition from the second mode to the first mode when a minimum therapeutic pressure is reached in the second mode.

10. The system of claim 1, wherein the controller is further configured to increase pressure in synchrony with inhalation of the user in the second mode.

11. The system of claim 1, wherein the controller is further configured to decrease pressure in synchrony with exhalation of the user in the second mode.

12. The system of claim 1, wherein the controller is further configured to detect an onset of inhalation of the user and transition from the first mode to the second mode based on the detected onset.

13. A method for controlling supply of respiratory gases from a flow generator to a user wearing a user interface, the method comprising:
  operating the flow generator in a first mode to create a first pressure that is below a therapeutic pressure range;
  transitioning from operating the flow generator in the first mode to operating the flow generator in a second mode to create a second pressure that is within the therapeutic pressure range when the user is determined to be asleep; and
  transitioning from operating the flow generating in the second mode to operating the flow generator in the first mode when the user is determined to be awake,
  wherein the transition from operating the flow generator from the first mode to the second mode is in synchrony with inhalation of the user.

14. The method of claim 13, wherein the transition from operating the flow generator from the second mode to the first mode is in synchrony with exhalation of the user.

15. The method of claim 13, further comprising monitoring a flow rate while operating in the first mode, determining when the flow rate decreases below a lower threshold for a preset period of time, and transitioning to the second mode based on the determination.

* * * * *